US011789012B2

(12) United States Patent
Janes et al.

(10) Patent No.: US 11,789,012 B2
(45) Date of Patent: Oct. 17, 2023

(54) CELL DEATH BIOMARKER

(71) Applicant: UCL Business PLC, London (GB)

(72) Inventors: Samuel Janes, Harpenden (GB); Krishna Kolluri, London (GB); Ultan McDermott, Hinxton (GB); Neelam Kumar, London (GB)

(73) Assignee: UCL Business Ltd, London (GB)

(*) Notice: Subject to any disclaimer, the term of this patent is extended or adjusted under 35 U.S.C. 154(b) by 279 days.

(21) Appl. No.: 16/333,590

(22) PCT Filed: Sep. 15, 2017

(86) PCT No.: PCT/GB2017/052733
§ 371 (c)(1),
(2) Date: Mar. 14, 2019

(87) PCT Pub. No.: WO2018/051110
PCT Pub. Date: Mar. 22, 2018

(65) Prior Publication Data

US 2019/0257818 A1 Aug. 22, 2019

(30) Foreign Application Priority Data

Sep. 16, 2016 (GB) .................................... 1615842

(51) Int. Cl.

| | |
|---|---|
| ***G01N 33/50*** | (2006.01) |
| ***A61P 35/00*** | (2006.01) |
| ***A61K 31/7105*** | (2006.01) |
| ***G01N 33/574*** | (2006.01) |

(52) U.S. Cl.
CPC ..... *G01N 33/5017* (2013.01); *A61K 31/7105* (2013.01); *A61P 35/00* (2018.01); *G01N 33/5023* (2013.01); *G01N 33/574* (2013.01); *G01N 2496/05* (2013.01); *G01N 2500/02* (2013.01); *G01N 2500/10* (2013.01); *G01N 2510/00* (2013.01); *G01N 2800/52* (2013.01)

(58) Field of Classification Search
CPC ........... G01N 33/5017; G01N 33/5023; G01N 33/574; G01N 2800/52; G01N 2496/05; G01N 2500/02; G01N 2500/10; G01N 2510/00; A61P 35/00; A61P 35/02; A61K 31/7105
See application file for complete search history.

(56) References Cited

U.S. PATENT DOCUMENTS

2002/0169123 A1 11/2002 El-Deiry et al.
2012/0077682 A1* 3/2012 Bowcock ......... G01N 33/57496 506/2
2016/0101071 A1* 4/2016 Cryns ................. A61K 9/0019 424/133.1

FOREIGN PATENT DOCUMENTS

EP 2044434 A2 4/2009
WO 2013/106002 7/2013

OTHER PUBLICATIONS

Battaglia (Clinical Medicine Insights 37-47, Apr. 28, 2014).*
Kolluri et al. Loss of functional BAP1 augments sensitivity to TRAIL in cancer cells. eLIFE 7: 1-23, published Jan. 18, 2018.*
Anand et al. Journal of Clinical Oncology 33 (3 suppl. abstract 420, Jan. 20, 2015.*
PCT International Search Report & Written Opinion dated Nov. 8, 2017, International Application No. PCT/GB2017/052733.
Farshi, Pershang, et al., "Deubiquitinases (DUBs) and DUB inhibitors: a patent review", Expert Opinion on Therapeutic Patents., vol. 25, No. 10, Jun. 16, 2015 (Jun. 16, 2015).
Hayes-Jordan A et al: "474 POSTER Inhibition of PDGFR-beta increases sarcoma cell sensitivity to tumor necrosis factor related apoptosis inducing ligand, TRAIL and promotes inhibition of tumor growth in dual therapy using imantanib (Gleevac) and TRAIL", European Journal of Cancer. Supplement, Pergamon, Oxford, GB, vol. 4, No. 12, Nov. 1, 2006 (Nov. 1, 2006), p. 145, XP027888933.
Ladanyi, M., et al., "New Strategies inPleural Mesothelioma: BAPI and NF2 asNovel Targets for Therapeutic Development and Risk Assessment",Clinical Cancer Research,vol. 18, No. 17, Jul. 23, 2012 (Jul. 23, 2012), pp. 4485-4490, XP055418148.
Polanski, R., et al., "Caspase-8 activation by TRAIL monotherapy predicts responses to IAPi and TRAIL combination treatment in breast cancer cell lines", Cell Death and Disease, vol. 6, No. 10, Oct. 1, 2015 (Oct. 1, 2015).
Walczak, H., "Death Receptor-Ligand Systems in Cancer, Cell Death, and Inflammation", Cold Spring Harbor Perspectives in Biology, vol. 5, No. 5, May 1, 2013 (May 1, 2013).
Yuan, Zhengqiang, et al., "Cryopreservation of human mesenchymal stromal cells expressing TRAIL for human anti-cancer therapy", Cytotherapy, vol. 18, No. 7, Jul. 2016 (Jul. 2016), pp. 860-869, XP002774967.

* cited by examiner

*Primary Examiner* — Alana Harris Dent
(74) *Attorney, Agent, or Firm* — GATES & COOPER LLP

(57) ABSTRACT

The invention relates to cell death of cancer cells, and in particular to biomarkers that may be used to identify cancer cells that are sensitive to death receptor ligand (DRL)-induced cell death. The invention also extends to prognostic methods and kits for identifying cancer cells that are sensitive to DRL-induced cell death. The invention further extends to novel compositions and therapeutic methods using such compositions for treating cancer.

5 Claims, 25 Drawing Sheets

Figure 1A:
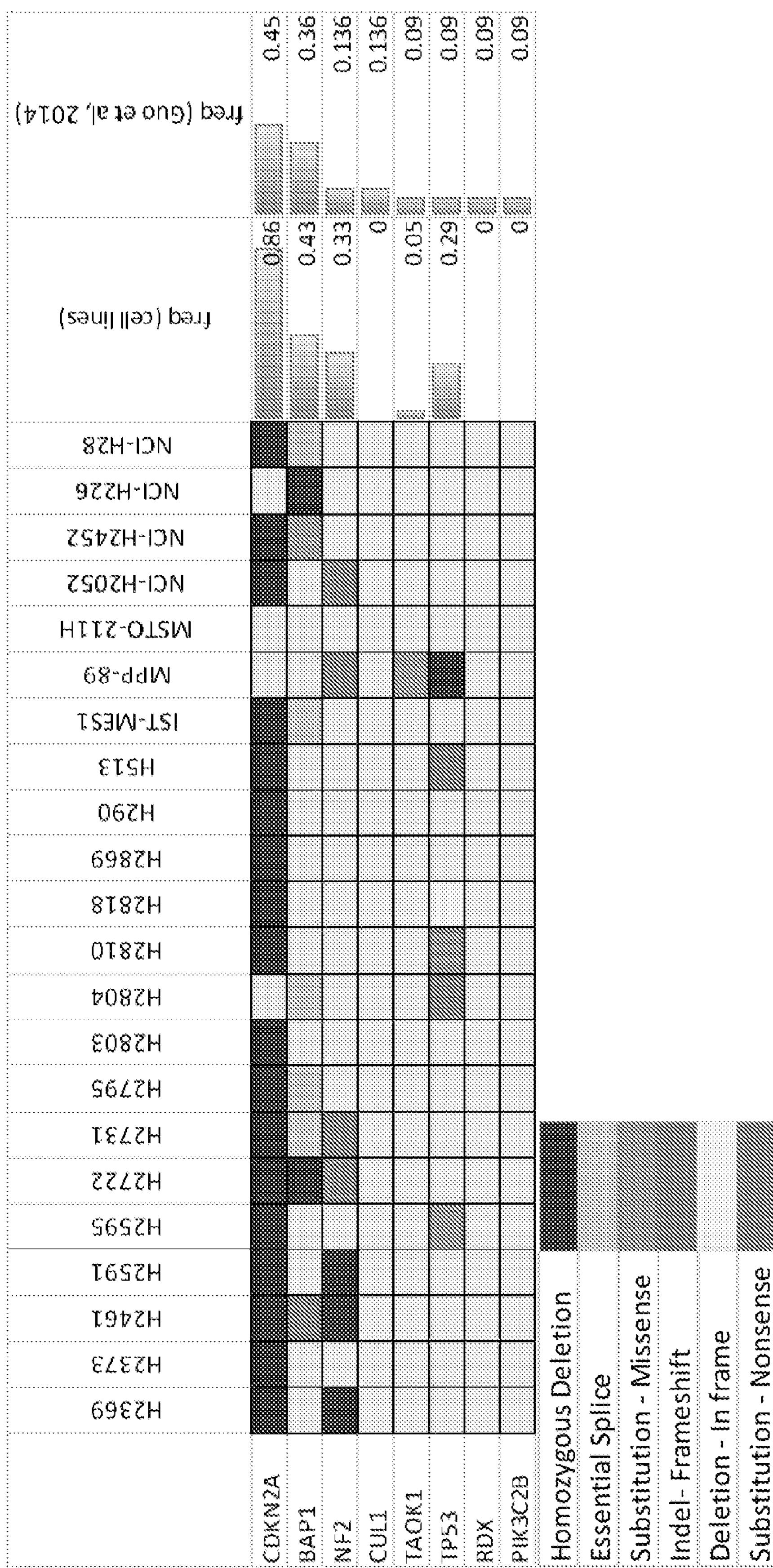

Specification includes a Sequence Listing.

SEQUENCE LISTING

```
<160> NUMBER OF SEQ ID NOS: 44

<210> SEQ ID NO 1
<211> LENGTH: 9102
<212> TYPE: DNA
<213> ORGANISM: Homo sapiens

<400> SEQUENCE: 1

gagcgcatgc ccgcatctgc tgtccgacag gcggaagacg agcccagagg cggagcaggg     60

ccgtcgcgcc ttggtgacgt ctgccgccgg cgcgggcggg tgacgcgact gggcccgttg    120

tctgtgtgtg ggactgaggg gccccggggg cggtgggggc tcccggtggg ggcagcggtg    180

gggagggagg gcctggacat ggcgctgagg ggccgccccg cgggaagatg aataagggct    240

ggctggagct ggagagcgac ccaggtgagg aggggaccgg gagggccagg ggctggggag    300

gccggatggg cccgggacgc gcctgcctga ccatcacccc ctcctcttgt cgccccaccc    360

aggcctcttc accctgctcg tggaagattt cggtaagagc cttttctccc tgccggaccg    420

gggctgtggc ggcccacccc tgcgccctca ctcatcaggg gctgtccttc cctactgctt    480

tcctttcctc atcgcaggtg tcaagggggt gcaagtggag gagatctacg accttcagag    540

caaatgtcag ggtgagtgg ctgtacacca gggctgcccc ttacacccag agtgctgggg    600

aaggtcccag agaacagggc cccttaggga agacagtgcc aggaacccta cgttgtaaaa    660

tctcacagaa agcagcagcc ttgctctctg agtgcccgct cctgatcaaa ctgatacttt    720

cttttctccc aaactttcct tagcgcttcc ctttttgtag cagccccctc cccacccta     780

agcatccttt ggttcagctg ctttcctggc cttgcagcgg gaagaccccg gtcacacaat    840

gtcttttgtg cagttgtgta atgtattaat tttagtgtgc ccatgtgtcc ttggctttaa    900

tcctgacaca aagtcatcct gtattgattg gttggggtga caaggcccct cctgggtgcc    960

cacacttaga gtcttttccc agtggtcctg cagaatagat gtgtaagaga gtagcaacag   1020

tagcaaccgt gactgaacca agaagtctac tttaatttcc tggaacaaaa gagactggtg   1080

tgggtgttca tttgctttcc tgactgcatt ggggcccaca agtgagaagg agtgcctcag   1140

ttcctcatca gagtttttgt tcttgtctta ctttgtgttc ctaccctgtc ccatccttgg   1200

ccctcagttc cagcttttct tctcttaccc agaactatag acttcataag gagactgggt   1260

ggactcctgg agcatcacag tcagaggctt atgctttgct ctgcctgtgg caggcctttg   1320

gtgtgtgagg gcacaaggcc acttcagaca cagtgttggg aagaagccag gggagagggg   1380

ggatcacagc aaggacacct gagtgatgac gcagtgcaaa ggattaatgg gagaaagaag   1440

ggaatgctga ttgtcttctc ccctttggct gatctggctc tgccccttac ttcccccagc   1500

cctgtatatg gatttatctt cctgttcaaa tggatcgaag agcgccggtc ccggcgaaag   1560

gtctctacct tggtggatga tacgtccgtg attgatgatg atattgtgaa taacatgttc   1620
```

-continued

```
tttgcccacc aggtctgctg gactctgtgc tttgtttgga gggtgggatg ctgccatgtt   1680
tttgcttggg aagtggaaat ggaggaagac aggaggagga gataggcaga ttctaggggt   1740
ggtagctaca gaaatcctct ggcagaacga actgaactct taattcatta aagggaacag   1800
ctttagagta ggagggtgtc tgagtccact ctctgtgtcc tcagatatcc agtgggtatt   1860
tggtaggtgc ttgttaaatg aataaacatt aggcaaagat gaaaggagct gagaagggga   1920
gttgtccaga tatgactgac ctgctctgga tccccattct tgatgtatat gggcttgggg   1980
cttgcagtga ggggtgctgt gtatgggtga ctattcttgg tttcacagct gatacccaac   2040
tcttgtgcaa ctcatgcctt gctgagcgtg ctcctgaact gcagcagcgt ggacctggga   2100
cccaccctga gtcgcatgaa ggacttcacc aagggtttca gccctgaggt aggctgcagt   2160
gccttcatcc tggctcacag ccaactgggc agatctgacc ctgagggcca ctgggaatgc   2220
taccacatga tattgggtac tattaggctg tttctttttc aaatgattgt ttatgttaca   2280
tttgactctt aaataaattg tgtaaggcca ttgtttttag atgcagttgc ggggaaagga   2340
cacaggccta gggagggagg agagtttcct taagtcagac catgtcagaa ccttctctgt   2400
caggactttt cctctcaggc catgttgctt cctagtgtcc actaattacc atgcaaggcc   2460
agcacagtcc atctctttgg ggctccagag ctcttttctg cccccaccag ccttttaaga   2520
aagttcgtct gtgttccttc cgattcctgg aatgcctcca ggctgctctc tgaagctttg   2580
ccttccaccc atagtcctac ctgaggagaa attattctga tacggcctta ttttcttccc   2640
cgtagagcaa aggatatgcg attggcaatg ccccggagtt ggccaaggcc cataatagcc   2700
atgccaggtg tgtgggagct gtgggagctg atgtggggtg ggagtagggg gagtatcatt   2760
ttttgggccc tgactctgtt tttccccagg cccgagccac gccacctccc tgagaagcag   2820
aatggcctta gtgcagtgcg gaccatggag gcgttccact ttgtcagcta tgtgcctatc   2880
acaggccggc tctttgagct ggatgggctg aaggtctacc ccattgacca tggtaggcac   2940
catgagctgg aggcctgttg ggtgtctctg cctacctcct agggagctgg ggctcagggc   3000
cctctggtat gtggtaccca gtggcagggg ttgtcggtac cgacacccgg ctctggctgg   3060
ggtttcaccc tacaccatat tgcccgacca gctcctgatt ccctggctca actgctcttc   3120
tctgtcttcc ttcccactcc tggcctgccc aaactcaggg tttccttctc gctgattcct   3180
tgtcttggtc tccactaggg ccctgggggg aggacgagga gtggacagac aaggcccggc   3240
gggtcatcat ggagcgtatc ggcctcgcca ctgcagggta agggccctgt gcctgccctg   3300
ttctactctc tggagctgta cctactttgg gagggacaga gagtatccag gtgatttgta   3360
aattgcaagg ccatatggtg aatctggcaa gatcaggctt agatcatggg ttctcaactt   3420
gttgtcttat ttcctgcctg ggctgcctgt ggcctgctcc tgggtgggct gggggagggg   3480
caggcctcag tggagcctta ggcagcccag gtctgctggt tcacttccag ataggcccct   3540
catacagctt gttggaaggt accagctcag gtgcctggca tgtatggcta gtcgctgcct   3600
gcctgttggg gtggggccta tacctacagc tgcaggtgtg actgcaggga gccctgccag   3660
gatatctgcc tcaacctgat ggcggggccg gggcgggagc tgctctcacg gctgcggctg   3720
tgactgcagg gagccctacc acgacatccg cttcaacctg atggcagtgg tgcccgaccg   3780
caggatcaag tatgaggcca ggctgcatgt gctgaaggtg aaccgtcaga cagtactaga   3840
ggctctgcag caggtaggtg ccctttcttc ctggcctctg cccagcccaa ccctccctgc   3900
attcctcctc ccttccccca cagcatttgt ctctgattcg tgaacatact ctcttgtaga   3960
```

-continued

```
tctgggcttc agctaaccac atcttttctt tgcccccatt gtgggaaagg tgggacttgg   4020
agtggggagg gagaatagct tctaaaagga agtttgggtt tgggtgtttt atttccctgt   4080
gagtgaatgg gtagagccaa ggccattatt cctttaggtc ctcagccctt agctatttaa   4140
ggtagaagcc cgggtctacc ctttctcctc tgagccctgg attctgttgt tagctgataa   4200
gagtaacaca gccagagctg attcagaccc acaagtctca agagtcacag ctgcctgagg   4260
agtccaagtc agccagcaac aagtccccgc tggtgctgga agcaaacagg gcccctgcag   4320
cctctgaggg caaccacaca ggtactgggg ggtttgggac ctcttgtgga cctcagagcc   4380
acccgctaat gtctgacatg ggaggcctaa acagggaaag tctttttctg ggatgtcct    4440
tgggcagtgt tcttccccg tcagaaggta gagggagagc agtccttccc taaagaaagg    4500
cacctgtaaa gggccgctgt taccacaggc ccctgggccc ttctctgtaa tgtacactcc   4560
ctttcttgtt ttctctagag gcggtttttt tttttttttt tttttttttt tttcttcctg   4620
cttctttttt cccatctcat tctttgccct gtctcattgc gggatcatga cttagagctt   4680
gctgactccc attgcaccag ctggctgggc tgttcttctc tgggaagtgc tggttcacag   4740
ggccggggag actgtgagct tttcttggag atcctactgg aggtcctgcc tgtgttcttg   4800
ccctgtctca gatggtgcag aggaggcggc tggttcatgc gcacaagccc catcccacag   4860
ccctcccaac aaacccaagc tagtggtgaa gcctccaggc agcagcctca atggggttca   4920
ccccaacccc actcccattg tccagcggct gccggccttt ctagacaatc acaattatgc   4980
caagtccccc atgcaggtaa gctgggagca cccttgcagg attctctact tgattctctt   5040
gagaggctgc aacaggcaat ttcccatgt ggttccttgg tgttcatcct tggcatggct    5100
gggtcaagct gcctgggcct gggttgctag gttcctctgc ctgatatgaa aaggccccca   5160
caacagcagg agcttaggga ggcagggaga gctcctttga atttaatcta gttacgtggc   5220
tgtgggatta aatgtttagg tcacgctcct tggtacaact tcatgggttg ggttttactg   5280
gcaaaataaa ggcatgtgtt tcagggcact ctgtttctct taaaacccct ccgtggggtt   5340
ctatccagtg taagtgggtg gcagcctccc cacaagccaa ggacaggcca tggaacagct   5400
ggaggggttc cgctgactca gtctggaaaa ccatgttggc tttctctctg gctgtgagtg   5460
tctaggctca gcctgggccg agcagcactt gtttgtaact gccctggtct ttgtcccagg   5520
aggaagaaga cctggcggca ggtgtgggcc gcagccgagt tccagtccgc ccaccccagc   5580
agtactcaga tgatgaggat gactatgagg atgacgagga ggatgacgtg cagaacacca   5640
actctgccct taggtcagcc cagctttcta aggctaccag gttctaggtg cttcggatcc   5700
catcctgaat atctcagtct gtgtctgaga atgccctgca gcagataatg ttgagcacct   5760
gcggagtttg gggccctggg ggaggctggc atgatggggc tgaccccagg tccccaggaa   5820
gtttttggtg ggctgggggg taaggctgag cacgtaagct tatatcatgt cctattggaa   5880
gtggcctttt agccaggcct tgaaggattg gttggggcag ggatggagga gatgtgggtg   5940
gtggggaggc agctttgctg gaacacaggg cattggcaaa aggccaggag tgggatggct   6000
ggaatagagg aagtgtcttt tgaggacact tggctgcagc tgtcagaact tgatgccagg   6060
cttagcatgg ctagttcaag ttgcttggac caagtataag gagttttagg gtcagcccct   6120
ggaggtcggg atgtatttaa gccattctgg gtactgctgg gtatggtcac ctggcccgtt   6180
cccttgcttc acatcttctc gggccccaca ggtataaggg gaagggaaca gggaagccag   6240
gggcattgag cggttctgct gatgggcaac tgtcagtgct gcagcccaac accatcaacg   6300
tcttggctga gaagctcaaa gagtcccaga aggacctctc aattcctctg tccatcaaga   6360
```

```
ctagcagcgg ggctgggagt ccggctgtgg cagtgcccac acactcgcag ccctcaccca   6420
cccccagcaa tgagagtaca gacacggcct ctgagatcgg cagtgctttc aactcgccac   6480
tgcgctcgcc tatccgctca gccaacccga cgcggccctc cagccctgtc acctcccaca   6540
tctccaaggt gctttttgga gaggatgaca gcctgctgcg tgttgactgc atacgctaca   6600
accgtgctgt ccgtgatctg ggtcctgtca tcagcacagg cctgctgcac ctggctgagg   6660
atggggtgct gagtcccctg gcgctgacag gtgggccttg gactggctca ctggccactt   6720
ggtgcaccca ggagggagga gggaagtggc caagtgacca caaagtgtcc tgcactctga   6780
tgattttctt gtgacctctc ttcccagagg gtgggaaggg ttcctcgccc tccatcagac   6840
caatccaagg cagccagggg tccagcagcc cagtggagaa ggaggtcgtg gaagccacgg   6900
acagcagaga gaagacgggg atggtgaggc ctggcgagcc cttgagtggg gagaaatact   6960
cacccaaggt gagcctccgt tgtggttttc tcctttaatc ctggcagagg gtaaggcctg   7020
agctcctcct gcccaggtgc caagttcttg attggaactt tggtgtgaag attggtggct   7080
ggagccatgt gccagaagac tttctgggtt gggtggtggc aggggccttg ataggcatgg   7140
actcgctgct catccttgcc tctagctgcc tattgctcgt ggggctttgt tgctggcccg   7200
ccccgatcag aggtgcaatg ctgggttttg gcaggagctg ctggcactgc tgaagtgtgt   7260
ggaggctgag attgcaaact atgaggcgtg cctcaaggag gaggtagaga agaggaagaa   7320
gttcaaggtg ggtgatttct ccagttgcct gatctggcct ctcccgaggt ccactggtgg   7380
ctgctctggc aagattggct ccagtgctct cagtcttctt ctctcctaca gattgatgac   7440
cagagaagga cccacaacta cgatgagttc atctgcacct ttatctccat gctggctcag   7500
gaaggtgagg ggatgcgctg ctgtcttaac tggaatgccc tgctgagggc cgtgtccttc   7560
agctcccctc ccctggcctc tcctgaggct tgagcagacc ttggggcaca gggagggcca   7620
tgagagcctc agctcctggc ctgaggcagc cagcacctgc tcaagggtct ctacctcttc   7680
gcaggcatgc tggccaacct agtggagcag aacatctccg tgcggcggcg ccaaggggtc   7740
agcatcggcc ggctccacaa gcagcggaag cctgaccggc ggaaacgctc tcgcccctac   7800
aaggccaagc gccagtgagg actgctggcc ctgactctgc agcccactct tgccgtgtgg   7860
ccctcaccag ggtccttccc tgccccactt cccctttcc cagtattact gaatagtccc   7920
agctggagag tccaggccct gggaatggga ggaaccaggc cacattcctt ccatcgtgcc   7980
ctgaggcctg acacggcaga tcagccccat agtgctcagg aggcagcatc tggagttggg   8040
gcacagcgag gtactgcagc ttcctccaca gccggctgtg gagcagcagg acctggccct   8100
tctgcctggg cagcagaata tatattttac ctatcagaga catctatttt tctgggctcc   8160
aacccaacat gccaccatgt tgacataagt tcctacctga ctatgctttc tctcctagga   8220
gctgtcctgg tgggcccagg tccttgtatc atgccacggt cccaactaca gggtcctagc   8280
tgggggcctg ggtgggccct gggctctggg ccctgctgct ctagccccag ccaccagcct   8340
gtccctgttg taaggaagcc aggtcttctc tcttcattcc tcttaggaga gtgccaaact   8400
cagggaccca gcactgggct gggttgggag tagggtgtcc cagtggggtt ggggtgagca   8460
ggctgctggg atcccatggc ctgagcagag catgtgggaa ctgttcagtg gcctgtgaac   8520
tgtcttcctt gttctagcca ggctgttcaa gactgctctc catagcaagg ttctagggct   8580
cttcgccttc agtgttgtgg ccctagctat gggcctaaat tgggctctag gtctctgtcc   8640
ctggcgcttg aggctcagaa gagcctctgt ccagcccctc agtattacca tgtctccctc   8700
```

```
tcaggggtag cagagacagg gttgcttata ggaagctggc accactcagc tcttcctgct   8760
actccagttt cctcagcctc tgcaaggcac tcagggtggg ggacagcagg atcaagacaa   8820
cccgttggag cccctgtgtt ccagaggacc tgatgccaag ggtaatggg cccagcagtg   8880
cctctggagc ccaggcccca acacagcccc atggcctctg ccagatggct ttgaaaaagg   8940
tgatccaagc aggccccttt atctgtacat agtgactgag tggggggtgc tggcaagtgt   9000
ggcagctgcc tctgggctga gcacagcttg acccctctag cccctgtaaa tactggatca   9060
atgaatgaat aaaactctcc taagaatctc ctgagaaatg aa                      9102
```

<210> SEQ ID NO 2
<211> LENGTH: 2190
<212> TYPE: DNA
<213> ORGANISM: Homo sapiens

<400> SEQUENCE: 2

```
atgaataagg gctggctgga gctggagagc gacccaggcc tcttcaccct gctcgtggaa     60
gatttcggtg tcaagggggt gcaagtggag gagatctacg accttcagag caaatgtcag    120
ggccctgtat atggatttat cttcctgttc aaatggatcg aagagcgccg gtcccggcga    180
aaggtctcta ccttggtgga tgatacgtcc gtgattgatg atgatattgt gaataacatg    240
ttctttgccc accagctgat acccaactct tgtgcaactc atgccttgct gagcgtgctc    300
ctgaactgca gcagcgtgga cctgggaccc accctgagtc gcatgaagga cttcaccaag    360
ggtttcagcc ctgagagcaa aggatatgcg attggcaatg ccccggagtt ggccaaggcc    420
cataatagcc atgccaggcc cgagccacgc cacctccctg agaagcagaa tggccttagt    480
gcagtgcgga ccatggaggc gttccacttt gtcagctatg tgcctatcac aggccggctc    540
tttgagctgg atgggctgaa ggtctacccc attgaccatg ggccctgggg ggaggacgag    600
gagtggacag acaaggcccg gcgggtcatc atggagcgta tcggcctcgc cactgcaggg    660
gagccctacc acgacatccg cttcaacctg atggcagtgg tgcccgaccg caggatcaag    720
tatgaggcca ggctgcatgt gctgaaggtg aaccgtcaga cagtactaga ggctctgcag    780
cagctgataa gagtaacaca gccagagctg attcagaccc acaagtctca agagtcacag    840
ctgcctgagg agtccaagtc agccagcaac aagtccccgc tggtgctgga agcaaacagg    900
gcccctgcag cctctgaggg caaccacaca gatggtgcag aggaggcggc tggttcatgc    960
gcacaagccc catcccacag ccctcccaac aaacccaagc tagtggtgaa gcctccaggc   1020
agcagcctca atggggttca ccccaacccc actcccattg tccagcggct gccggccttt   1080
ctagacaatc acaattatgc caagtccccc atgcaggagg aagaagacct ggcggcaggt   1140
gtgggccgca gccgagttcc agtccgccca ccccagcagt actcagatga tgaggatgac   1200
tatgaggatg acgaggagga tgacgtgcag aacaccaact ctgcccttag gtataagggg   1260
aagggaacag ggaagccagg ggcattgagc ggttctgctg atgggcaact gtcagtgctg   1320
cagcccaaca ccatcaacgt cttggctgag aagctcaaag agtcccagaa ggacctctca   1380
attcctctgt ccatcaagac tagcagcggg gctgggagtc cggctgtggc agtgcccaca   1440
cactcgcagc cctcacccac ccccagcaat gagagtacag acacggcctc tgagatcggc   1500
agtgctttca actcgccact gcgctcgcct atccgctcag ccaacccgac gcggccctcc   1560
agccctgtca cctcccacat ctccaaggtg ctttttggag aggatgacag cctgctgcgt   1620
gttgactgca tacgctacaa ccgtgctgtc cgtgatctgg gtcctgtcat cagcacaggc   1680
ctgctgcacc tggctgagga tggggtgctg agtcccctgg cgctgacaga gggtgggaag   1740
```

```
ggttcctcgc cctccatcag accaatccaa ggcagccagg ggtccagcag cccagtggag   1800

aaggaggtcg tggaagccac ggacagcaga gagaagacgg ggatggtgag gcctggcgag   1860

cccttgagtg gggagaaata ctcacccaag gagctgctgg cactgctgaa gtgtgtggag   1920

gctgagattg caaactatga ggcgtgcctc aaggaggagg tagagaagag gaagaagttc   1980

aagattgatg accagagaag gacccacaac tacgatgagt tcatctgcac ctttatctcc   2040

atgctggctc aggaaggcat gctggccaac ctagtggagc agaacatctc cgtgcggcgg   2100

cgccaagggg tcagcatcgg ccggctccac aagcagcgga agcctgaccg gcggaaacgc   2160

tctcgcccct acaaggccaa gcgccagtga                                    2190
```

```
<210> SEQ ID NO 3
<211> LENGTH: 729
<212> TYPE: PRT
<213> ORGANISM: Homo sapiens

<400> SEQUENCE: 3

Met Asn Lys Gly Trp Leu Glu Leu Glu Ser Asp Pro Gly Leu Phe Thr
1               5                   10                  15

Leu Leu Val Glu Asp Phe Gly Val Lys Gly Val Gln Val Glu Glu Ile
            20                  25                  30

Tyr Asp Leu Gln Ser Lys Cys Gln Gly Pro Val Tyr Gly Phe Ile Phe
        35                  40                  45

Leu Phe Lys Trp Ile Glu Glu Arg Arg Ser Arg Arg Lys Val Ser Thr
    50                  55                  60

Leu Val Asp Asp Thr Ser Val Ile Asp Asp Asp Ile Val Asn Asn Met
65                  70                  75                  80

Phe Phe Ala His Gln Leu Ile Pro Asn Ser Cys Ala Thr His Ala Leu
                85                  90                  95

Leu Ser Val Leu Leu Asn Cys Ser Ser Val Asp Leu Gly Pro Thr Leu
            100                 105                 110

Ser Arg Met Lys Asp Phe Thr Lys Gly Phe Ser Pro Glu Ser Lys Gly
        115                 120                 125

Tyr Ala Ile Gly Asn Ala Pro Glu Leu Ala Lys Ala His Asn Ser His
    130                 135                 140

Ala Arg Pro Glu Pro Arg His Leu Pro Glu Lys Gln Asn Gly Leu Ser
145                 150                 155                 160

Ala Val Arg Thr Met Glu Ala Phe His Phe Val Ser Tyr Val Pro Ile
                165                 170                 175

Thr Gly Arg Leu Phe Glu Leu Asp Gly Leu Lys Val Tyr Pro Ile Asp
            180                 185                 190

His Gly Pro Trp Gly Glu Asp Glu Glu Trp Thr Asp Lys Ala Arg Arg
        195                 200                 205

Val Ile Met Glu Arg Ile Gly Leu Ala Thr Ala Gly Glu Pro Tyr His
    210                 215                 220

Asp Ile Arg Phe Asn Leu Met Ala Val Val Pro Asp Arg Arg Ile Lys
225                 230                 235                 240

Tyr Glu Ala Arg Leu His Val Leu Lys Val Asn Arg Gln Thr Val Leu
                245                 250                 255

Glu Ala Leu Gln Gln Leu Ile Arg Val Thr Gln Pro Glu Leu Ile Gln
            260                 265                 270

Thr His Lys Ser Gln Glu Ser Gln Leu Pro Glu Glu Ser Lys Ser Ala
        275                 280                 285
```

-continued

```
Ser Asn Lys Ser Pro Leu Val Leu Glu Ala Asn Arg Ala Pro Ala Ala
    290                 295                 300

Ser Glu Gly Asn His Thr Asp Gly Ala Glu Glu Ala Ala Gly Ser Cys
305                 310                 315                 320

Ala Gln Ala Pro Ser His Ser Pro Pro Asn Lys Pro Lys Leu Val Val
                325                 330                 335

Lys Pro Pro Gly Ser Ser Leu Asn Gly Val His Pro Asn Pro Thr Pro
            340                 345                 350

Ile Val Gln Arg Leu Pro Ala Phe Leu Asp Asn His Asn Tyr Ala Lys
        355                 360                 365

Ser Pro Met Gln Glu Glu Glu Asp Leu Ala Ala Gly Val Gly Arg Ser
    370                 375                 380

Arg Val Pro Val Arg Pro Pro Gln Gln Tyr Ser Asp Asp Glu Asp Asp
385                 390                 395                 400

Tyr Glu Asp Asp Glu Glu Asp Asp Val Gln Asn Thr Asn Ser Ala Leu
                405                 410                 415

Arg Tyr Lys Gly Lys Gly Thr Gly Lys Pro Gly Ala Leu Ser Gly Ser
            420                 425                 430

Ala Asp Gly Gln Leu Ser Val Leu Gln Pro Asn Thr Ile Asn Val Leu
        435                 440                 445

Ala Glu Lys Leu Lys Glu Ser Gln Lys Asp Leu Ser Ile Pro Leu Ser
    450                 455                 460

Ile Lys Thr Ser Ser Gly Ala Gly Ser Pro Ala Val Ala Val Pro Thr
465                 470                 475                 480

His Ser Gln Pro Ser Pro Thr Pro Ser Asn Glu Ser Thr Asp Thr Ala
                485                 490                 495

Ser Glu Ile Gly Ser Ala Phe Asn Ser Pro Leu Arg Ser Pro Ile Arg
            500                 505                 510

Ser Ala Asn Pro Thr Arg Pro Ser Ser Pro Val Thr Ser His Ile Ser
        515                 520                 525

Lys Val Leu Phe Gly Glu Asp Asp Ser Leu Leu Arg Val Asp Cys Ile
    530                 535                 540

Arg Tyr Asn Arg Ala Val Arg Asp Leu Gly Pro Val Ile Ser Thr Gly
545                 550                 555                 560

Leu Leu His Leu Ala Glu Asp Gly Val Leu Ser Pro Leu Ala Leu Thr
                565                 570                 575

Glu Gly Gly Lys Gly Ser Ser Pro Ser Ile Arg Pro Ile Gln Gly Ser
            580                 585                 590

Gln Gly Ser Ser Ser Pro Val Glu Lys Glu Val Val Glu Ala Thr Asp
        595                 600                 605

Ser Arg Glu Lys Thr Gly Met Val Arg Pro Gly Glu Pro Leu Ser Gly
    610                 615                 620

Glu Lys Tyr Ser Pro Lys Glu Leu Leu Ala Leu Leu Lys Cys Val Glu
625                 630                 635                 640

Ala Glu Ile Ala Asn Tyr Glu Ala Cys Leu Lys Glu Glu Val Glu Lys
                645                 650                 655

Arg Lys Lys Phe Lys Ile Asp Asp Gln Arg Arg Thr His Asn Tyr Asp
            660                 665                 670

Glu Phe Ile Cys Thr Phe Ile Ser Met Leu Ala Gln Glu Gly Met Leu
        675                 680                 685

Ala Asn Leu Val Glu Gln Asn Ile Ser Val Arg Arg Arg Gln Gly Val
    690                 695                 700

Ser Ile Gly Arg Leu His Lys Gln Arg Lys Pro Asp Arg Arg Lys Arg
```

```
705                 710                 715                 720

Ser Arg Pro Tyr Lys Ala Lys Arg Gln
                725


<210> SEQ ID NO 4
<211> LENGTH: 729
<212> TYPE: PRT
<213> ORGANISM: Homo sapiens

<400> SEQUENCE: 4

Met Asn Lys Gly Trp Leu Glu Leu Glu Ser Asp Pro Gly Leu Phe Thr
1               5                   10                  15

Leu Leu Val Glu Asp Phe Gly Val Lys Gly Val Gln Val Glu Glu Ile
            20                  25                  30

Tyr Asp Leu Gln Ser Lys Cys Gln Gly Pro Val Tyr Gly Phe Ile Phe
        35                  40                  45

Leu Phe Lys Trp Ile Glu Glu Arg Arg Ser Arg Gln Lys Val Ser Thr
    50                  55                  60

Leu Val Asp Asp Thr Ser Val Ile Asp Asp Asp Ile Val Asn Asn Met
65                  70                  75                  80

Phe Phe Ala His Gln Leu Ile Pro Asn Ser Cys Ala Thr His Ala Leu
                85                  90                  95

Leu Ser Val Leu Leu Asn Cys Ser Ser Val Asp Leu Gly Pro Thr Leu
            100                 105                 110

Ser Arg Met Lys Asp Phe Thr Lys Gly Phe Ser Pro Glu Ser Lys Gly
        115                 120                 125

Tyr Ala Ile Gly Asn Ala Pro Glu Leu Ala Lys Ala His Asn Ser His
    130                 135                 140

Ala Arg Pro Glu Pro Arg His Leu Pro Glu Lys Gln Asn Gly Leu Ser
145                 150                 155                 160

Ala Val Arg Thr Met Glu Ala Phe His Phe Val Ser Tyr Val Pro Ile
                165                 170                 175

Thr Gly Arg Leu Phe Glu Leu Asp Gly Leu Lys Val Tyr Pro Ile Asp
            180                 185                 190

His Gly Pro Trp Gly Glu Asp Glu Glu Trp Thr Asp Lys Ala Arg Arg
        195                 200                 205

Val Ile Met Glu Arg Ile Gly Leu Ala Thr Ala Gly Glu Pro Tyr His
    210                 215                 220

Asp Ile Arg Phe Asn Leu Met Ala Val Val Pro Asp Arg Arg Ile Lys
225                 230                 235                 240

Tyr Glu Ala Arg Leu His Val Leu Lys Val Asn Arg Gln Thr Val Leu
                245                 250                 255

Glu Ala Leu Gln Gln Leu Ile Arg Val Thr Gln Pro Glu Leu Ile Gln
            260                 265                 270

Thr His Lys Ser Gln Glu Ser Gln Leu Pro Glu Glu Ser Lys Ser Ala
        275                 280                 285

Ser Asn Lys Ser Pro Leu Val Leu Glu Ala Asn Arg Ala Pro Ala Ala
    290                 295                 300

Ser Glu Gly Asn His Thr Asp Gly Ala Glu Glu Ala Ala Gly Ser Cys
305                 310                 315                 320

Ala Gln Ala Pro Ser His Ser Pro Pro Asn Lys Pro Lys Leu Val Val
                325                 330                 335

Lys Pro Pro Gly Ser Ser Leu Asn Gly Val His Pro Asn Pro Thr Pro
            340                 345                 350
```

```
Ile Val Gln Arg Leu Pro Ala Phe Leu Asp Asn His Asn Tyr Ala Lys
        355                 360                 365

Ser Pro Met Gln Glu Glu Glu Asp Leu Ala Ala Gly Val Gly Arg Ser
    370                 375                 380

Arg Val Pro Val Arg Pro Pro Gln Gln Tyr Ser Asp Asp Glu Asp Asp
385                 390                 395                 400

Tyr Glu Asp Asp Glu Glu Asp Asp Val Gln Asn Thr Asn Ser Ala Leu
                405                 410                 415

Arg Tyr Lys Gly Lys Gly Thr Gly Lys Pro Gly Ala Leu Ser Gly Ser
            420                 425                 430

Ala Asp Gly Gln Leu Ser Val Leu Gln Pro Asn Thr Ile Asn Val Leu
        435                 440                 445

Ala Glu Lys Leu Lys Glu Ser Gln Lys Asp Leu Ser Ile Pro Leu Ser
    450                 455                 460

Ile Lys Thr Ser Ser Gly Ala Gly Ser Pro Ala Val Ala Val Pro Thr
465                 470                 475                 480

His Ser Gln Pro Ser Pro Thr Pro Ser Asn Glu Ser Thr Asp Thr Ala
                485                 490                 495

Ser Glu Ile Gly Ser Ala Phe Asn Ser Pro Leu Arg Ser Pro Ile Arg
            500                 505                 510

Ser Ala Asn Pro Thr Arg Pro Ser Ser Pro Val Thr Ser His Ile Ser
        515                 520                 525

Lys Val Leu Phe Gly Glu Asp Asp Ser Leu Leu Arg Val Asp Cys Ile
    530                 535                 540

Arg Tyr Asn Arg Ala Val Arg Asp Leu Gly Pro Val Ile Ser Thr Gly
545                 550                 555                 560

Leu Leu His Leu Ala Glu Asp Gly Val Leu Ser Pro Leu Ala Leu Thr
                565                 570                 575

Glu Gly Gly Lys Gly Ser Ser Pro Ser Ile Arg Pro Ile Gln Gly Ser
            580                 585                 590

Gln Gly Ser Ser Ser Pro Val Glu Lys Glu Val Val Glu Ala Thr Asp
        595                 600                 605

Ser Arg Glu Lys Thr Gly Met Val Arg Pro Gly Glu Pro Leu Ser Gly
    610                 615                 620

Glu Lys Tyr Ser Pro Lys Glu Leu Leu Ala Leu Leu Lys Cys Val Glu
625                 630                 635                 640

Ala Glu Ile Ala Asn Tyr Glu Ala Cys Leu Lys Glu Glu Val Glu Lys
                645                 650                 655

Arg Lys Lys Phe Lys Ile Asp Asp Gln Arg Arg Thr His Asn Tyr Asp
            660                 665                 670

Glu Phe Ile Cys Thr Phe Ile Ser Met Leu Ala Gln Glu Gly Met Leu
        675                 680                 685

Ala Asn Leu Val Glu Gln Asn Ile Ser Val Arg Arg Arg Gln Gly Val
    690                 695                 700

Ser Ile Gly Arg Leu His Lys Gln Arg Lys Pro Asp Arg Arg Lys Arg
705                 710                 715                 720

Ser Arg Pro Tyr Lys Ala Lys Arg Gln
                725
```

<210> SEQ ID NO 5
<211> LENGTH: 2190
<212> TYPE: DNA
<213> ORGANISM: Homo sapiens

<400> SEQUENCE: 5

```
atgaataagg gctggctgga gctggagagc gacccaggcc tcttcaccct gctcgtggaa      60
gatttcggtg tcaagggggt gcaagtggag gagatctacg accttcagag caaatgtcag     120
ggccctgtat atggatttat cttcctgttc aaatggatcg aagagcgccg gtcccggcaa     180
aaggtctcta ccttggtgga tgatacgtcc gtgattgatg atgatattgt gaataacatg     240
ttctttgccc accagctgat acccaactct tgtgcaactc atgccttgct gagcgtgctc     300
ctgaactgca gcagcgtgga cctgggaccc accctgagtc gcatgaagga cttcaccaag     360
ggtttcagcc ctgagagcaa aggatatgcg attggcaatg ccccggagtt ggccaaggcc     420
cataatagcc atgccaggcc cgagccacgc cacctccctg agaagcagaa tggccttagt     480
gcagtgcgga ccatggaggc gttccacttt gtcagctatg tgcctatcac aggccggctc     540
tttgagctgg atgggctgaa ggtctacccc attgaccatg ggccctgggg ggaggacgag     600
gagtggacag acaaggcccg gcgggtcatc atggagcgta tcggcctcgc cactgcaggg     660
gagccctacc acgacatccg cttcaacctg atggcagtgg tgcccgaccg caggatcaag     720
tatgaggcca ggctgcatgt gctgaaggtg aaccgtcaga cagtactaga ggctctgcag     780
cagctgataa gagtaacaca gccagagctg attcagaccc acaagtctca agagtcacag     840
ctgcctgagg agtccaagtc agccagcaac aagtccccgc tggtgctgga agcaaacagg     900
gcccctgcag cctctgaggg caaccacaca gatggtgcag aggaggcggc tggttcatgc     960
gcacaagccc catcccacag ccctcccaac aaacccaagc tagtggtgaa gcctccaggc    1020
agcagcctca atggggttca ccccaacccc actcccattg tccagcggct gccggccttt    1080
ctagacaatc acaattatgc caagtccccc atgcaggagg aagaagacct ggcggcaggt    1140
gtgggccgca gccgagttcc agtccgccca ccccagcagt actcagatga tgaggatgac    1200
tatgaggatg acgaggagga tgacgtgcag aacaccaact ctgcccttag gtataagggg    1260
aagggaacag ggaagccagg ggcattgagc ggttctgctg atgggcaact gtcagtgctg    1320
cagcccaaca ccatcaacgt cttggctgag aagctcaaag agtcccagaa ggacctctca    1380
attcctctgt ccatcaagac tagcagcggg gctgggagtc cggctgtggc agtgcccaca    1440
cactcgcagc cctcacccac ccccagcaat gagagtacag acacggcctc tgagatcggc    1500
agtgctttca actcgccact gcgctcgcct atccgctcag ccaacccgac gcggccctcc    1560
agccctgtca cctcccacat ctccaaggtg ctttttggag aggatgacag cctgctgcgt    1620
gttgactgca tacgctacaa ccgtgctgtc cgtgatctgg gtcctgtcat cagcacaggc    1680
ctgctgcacc tggctgagga tggggtgctg agtcccctgg cgctgacaga gggtgggaag    1740
ggttcctcgc cctccatcag accaatccaa ggcagccagg ggtccagcag cccagtggag    1800
aaggaggtcg tggaagccac ggacagcaga gagaagacgg ggatggtgag gcctggcgag    1860
cccttgagtg gggagaaata ctcacccaag gagctgctgg cactgctgaa gtgtgtggag    1920
gctgagattg caaactatga ggcgtgcctc aaggaggagg tagagaagag gaagaagttc    1980
aagattgatg accagagaag gacccacaac tacgatgagt tcatctgcac ctttatctcc    2040
atgctggctc aggaaggcat gctggccaac ctagtggagc agaacatctc cgtgcggcgg    2100
cgccaagggg tcagcatcgg ccggctccac aagcagcgga agcctgaccg gcggaaacgc    2160
tctcgcccct acaaggccaa gcgccagtga                                     2190
```

<210> SEQ ID NO 6
<211> LENGTH: 22
<212> TYPE: DNA

<213> ORGANISM: Artificial Sequence
<220> FEATURE:
<223> OTHER INFORMATION: Synthetic Primer

<400> SEQUENCE: 6
acctagaacc tggtagcctt ag 22

<210> SEQ ID NO 7
<211> LENGTH: 22
<212> TYPE: DNA
<213> ORGANISM: Artificial Sequence
<220> FEATURE:
<223> OTHER INFORMATION: Synthetic Primer

<400> SEQUENCE: 7
gtacagctcc agagagtaga ac 22

<210> SEQ ID NO 8
<211> LENGTH: 22
<212> TYPE: DNA
<213> ORGANISM: Artificial Sequence
<220> FEATURE:
<223> OTHER INFORMATION: Synthetic Primer

<400> SEQUENCE: 8
tcttaccgaa atcttccacg ag 22

<210> SEQ ID NO 9
<211> LENGTH: 22
<212> TYPE: DNA
<213> ORGANISM: Artificial Sequence
<220> FEATURE:
<223> OTHER INFORMATION: Synthetic Primer

<400> SEQUENCE: 9
ctgctgcttt ctgtgagatt tt 22

<210> SEQ ID NO 10
<211> LENGTH: 21
<212> TYPE: DNA
<213> ORGANISM: Artificial Sequence
<220> FEATURE:
<223> OTHER INFORMATION: Synthetic Primer

<400> SEQUENCE: 10
agggcattcc agttaagaca g 21

<210> SEQ ID NO 11
<211> LENGTH: 18
<212> TYPE: DNA
<213> ORGANISM: Artificial Sequence
<220> FEATURE:
<223> OTHER INFORMATION: Synthetic Primer

<400> SEQUENCE: 11
caagagtggg ctgcagag 18

<210> SEQ ID NO 12
<211> LENGTH: 21
<212> TYPE: DNA
<213> ORGANISM: Artificial Sequence
<220> FEATURE:
<223> OTHER INFORMATION: Synthetic Primer

<400> SEQUENCE: 12
actaaggcca ttctgcttct c 21

<210> SEQ ID NO 13
<211> LENGTH: 20
<212> TYPE: DNA
<213> ORGANISM: Artificial Sequence
<220> FEATURE:
<223> OTHER INFORMATION: Synthetic Primer

<400> SEQUENCE: 13
atcccaccct ccaaacaaag 20

<210> SEQ ID NO 14
<211> LENGTH: 18
<212> TYPE: DNA
<213> ORGANISM: Artificial Sequence
<220> FEATURE:
<223> OTHER INFORMATION: Synthetic Primer

<400> SEQUENCE: 14
caccaagtgg ccagtgag 18

<210> SEQ ID NO 15
<211> LENGTH: 20
<212> TYPE: DNA
<213> ORGANISM: Artificial Sequence
<220> FEATURE:
<223> OTHER INFORMATION: Synthetic Primer

<400> SEQUENCE: 15
ggctgtcatc ctctccaaaa 20

<210> SEQ ID NO 16
<211> LENGTH: 18
<212> TYPE: DNA
<213> ORGANISM: Artificial Sequence
<220> FEATURE:
<223> OTHER INFORMATION: Synthetic Primer

<400> SEQUENCE: 16
gagggctgcg agtgtgtg 18

<210> SEQ ID NO 17
<211> LENGTH: 22
<212> TYPE: DNA
<213> ORGANISM: Artificial Sequence
<220> FEATURE:
<223> OTHER INFORMATION: Synthetic Primer

<400> SEQUENCE: 17
ctctgccagg attaaaggag aa 22

<210> SEQ ID NO 18
<211> LENGTH: 18
<212> TYPE: DNA
<213> ORGANISM: Artificial Sequence
<220> FEATURE:
<223> OTHER INFORMATION: Synthetic Primer

<400> SEQUENCE: 18
gaatgcaggg agggttgg 18

<210> SEQ ID NO 19
<211> LENGTH: 22
<212> TYPE: DNA
<213> ORGANISM: Artificial Sequence
<220> FEATURE:

<223> OTHER INFORMATION: Synthetic Primer

<400> SEQUENCE: 19
acccaatatc atgtggtagc at 22

<210> SEQ ID NO 20
<211> LENGTH: 18
<212> TYPE: DNA
<213> ORGANISM: Artificial Sequence
<220> FEATURE:
<223> OTHER INFORMATION: Synthetic Primer

<400> SEQUENCE: 20
aaggacagcc cctgatga 18

<210> SEQ ID NO 21
<211> LENGTH: 19
<212> TYPE: DNA
<213> ORGANISM: Artificial Sequence
<220> FEATURE:
<223> OTHER INFORMATION: Synthetic Primer

<400> SEQUENCE: 21
gtaggcagag acacccaac 19

<210> SEQ ID NO 22
<211> LENGTH: 22
<212> TYPE: DNA
<213> ORGANISM: Artificial Sequence
<220> FEATURE:
<223> OTHER INFORMATION: Synthetic Primer

<400> SEQUENCE: 22
ccttctctgg tcatcaatct gt 22

<210> SEQ ID NO 23
<211> LENGTH: 20
<212> TYPE: DNA
<213> ORGANISM: Artificial Sequence
<220> FEATURE:
<223> OTHER INFORMATION: Synthetic Primer

<400> SEQUENCE: 23
ctctgaggtc cacaagaggt 20

<210> SEQ ID NO 24
<211> LENGTH: 22
<212> TYPE: DNA
<213> ORGANISM: Artificial Sequence
<220> FEATURE:
<223> OTHER INFORMATION: Synthetic Primer

<400> SEQUENCE: 24
tcaagtagag aatcctgcaa gg 22

<210> SEQ ID NO 25
<211> LENGTH: 22
<212> TYPE: DNA
<213> ORGANISM: Artificial Sequence
<220> FEATURE:
<223> OTHER INFORMATION: Synthetic Primer

<400> SEQUENCE: 25
gagcagcact tgtttgtaac tg 22

<210> SEQ ID NO 26
<211> LENGTH: 22
<212> TYPE: DNA
<213> ORGANISM: Artificial Sequence
<220> FEATURE:
<223> OTHER INFORMATION: Synthetic Primer

<400> SEQUENCE: 26
ctcaactgct cttctctgtc tt 22

<210> SEQ ID NO 27
<211> LENGTH: 18
<212> TYPE: DNA
<213> ORGANISM: Artificial Sequence
<220> FEATURE:
<223> OTHER INFORMATION: Synthetic Primer

<400> SEQUENCE: 27
gagggagggc ctggacat 18

<210> SEQ ID NO 28
<211> LENGTH: 21
<212> TYPE: DNA
<213> ORGANISM: Artificial Sequence
<220> FEATURE:
<223> OTHER INFORMATION: Synthetic Primer

<400> SEQUENCE: 28
ctgtccttcc ctactgcttt c 21

<210> SEQ ID NO 29
<211> LENGTH: 22
<212> TYPE: DNA
<213> ORGANISM: Artificial Sequence
<220> FEATURE:
<223> OTHER INFORMATION: Synthetic Primer

<400> SEQUENCE: 29
gaagttcaag gtgggtgatt tc 22

<210> SEQ ID NO 30
<211> LENGTH: 18
<212> TYPE: DNA
<213> ORGANISM: Artificial Sequence
<220> FEATURE:
<223> OTHER INFORMATION: Synthetic Primer

<400> SEQUENCE: 30
ctcagctcct ggcctgag 18

<210> SEQ ID NO 31
<211> LENGTH: 23
<212> TYPE: DNA
<213> ORGANISM: Artificial Sequence
<220> FEATURE:
<223> OTHER INFORMATION: Synthetic Primer

<400> SEQUENCE: 31
ggagaaatta ttctgatacg gcc 23

<210> SEQ ID NO 32
<211> LENGTH: 22
<212> TYPE: DNA
<213> ORGANISM: Artificial Sequence
<220> FEATURE:
<223> OTHER INFORMATION: Synthetic Primer

<400> SEQUENCE: 32
gaagggaatg ctgattgtct tc 22

<210> SEQ ID NO 33
<211> LENGTH: 18
<212> TYPE: DNA
<213> ORGANISM: Artificial Sequence
<220> FEATURE:
<223> OTHER INFORMATION: Synthetic Primer

<400> SEQUENCE: 33
ctatccgctc agccaacc 18

<210> SEQ ID NO 34
<211> LENGTH: 22
<212> TYPE: DNA
<213> ORGANISM: Artificial Sequence
<220> FEATURE:
<223> OTHER INFORMATION: Synthetic Primer

<400> SEQUENCE: 34
ctctcaattc ctctgtccat ca 22

<210> SEQ ID NO 35
<211> LENGTH: 20
<212> TYPE: DNA
<213> ORGANISM: Artificial Sequence
<220> FEATURE:
<223> OTHER INFORMATION: Synthetic Primer

<400> SEQUENCE: 35
cgttcccttg cttcacatct 20

<210> SEQ ID NO 36
<211> LENGTH: 22
<212> TYPE: DNA
<213> ORGANISM: Artificial Sequence
<220> FEATURE:
<223> OTHER INFORMATION: Synthetic Primer

<400> SEQUENCE: 36
tcctgcactc tgatgatttt ct 22

<210> SEQ ID NO 37
<211> LENGTH: 22
<212> TYPE: DNA
<213> ORGANISM: Artificial Sequence
<220> FEATURE:
<223> OTHER INFORMATION: Synthetic Primer

<400> SEQUENCE: 37
gatatctgcc tcaacctgat gg 22

<210> SEQ ID NO 38
<211> LENGTH: 20
<212> TYPE: DNA
<213> ORGANISM: Artificial Sequence
<220> FEATURE:
<223> OTHER INFORMATION: Synthetic Primer

<400> SEQUENCE: 38
gtgctgtgta tgggtgacta 20

<210> SEQ ID NO 39
<211> LENGTH: 21

<212> TYPE: DNA
<213> ORGANISM: Artificial Sequence
<220> FEATURE:
<223> OTHER INFORMATION: Synthetic Primer

<400> SEQUENCE: 39
gaagatgaat aagggctggc t 21

<210> SEQ ID NO 40
<211> LENGTH: 19
<212> TYPE: DNA
<213> ORGANISM: Artificial Sequence
<220> FEATURE:
<223> OTHER INFORMATION: Synthetic Primer

<400> SEQUENCE: 40
tgatgtgggg tgggagtag 19

<210> SEQ ID NO 41
<211> LENGTH: 18
<212> TYPE: DNA
<213> ORGANISM: Artificial Sequence
<220> FEATURE:
<223> OTHER INFORMATION: Synthetic Primer

<400> SEQUENCE: 41
cccgatcaga ggtgcaat 18

<210> SEQ ID NO 42
<211> LENGTH: 22
<212> TYPE: DNA
<213> ORGANISM: Artificial Sequence
<220> FEATURE:
<223> OTHER INFORMATION: Synthetic Primer

<400> SEQUENCE: 42
agctatttaa ggtagaagcc cg 22

<210> SEQ ID NO 43
<211> LENGTH: 22
<212> TYPE: DNA
<213> ORGANISM: Artificial Sequence
<220> FEATURE:
<223> OTHER INFORMATION: Synthetic Primer

<400> SEQUENCE: 43
actgtgagct tttcttggag at 22

<210> SEQ ID NO 44
<211> LENGTH: 19
<212> TYPE: DNA
<213> ORGANISM: Artificial Sequence
<220> FEATURE:
<223> OTHER INFORMATION: Synthetic sequence for short hairpin

<400> SEQUENCE: 44
taaaggtgca gatgaactc 19

CELL DEATH BIOMARKER

The present invention relates to cell death of cancer cells, and in particular to biomarkers that may be used to identify cancer cells that are sensitive to death receptor ligand (DRL)-induced cell death. The invention also extends to prognostic methods and kits for identifying cancer cells that are sensitive to DRL-induced cell death. The invention further extends to novel compositions and therapeutic methods using such compositions for treating cancer.

Malignant pleural mesothelioma (MPM) is a rare but invariably fatal malignancy that occurs most frequently in the pleura and is almost always associated with asbestos exposure (1, 2). Although asbestos mining and usage has been the subject of legislation in many nations, there remains evidence of increased use and production of asbestos as the trend towards global industrialisation increases (3). Given a cancer latency period of anywhere from 10-40 years, it is therefore likely that in such countries asbestos-related cancers will increase over the next five decades. Current treatment options for patients diagnosed with MPM are limited. Radical surgery, for example, offers limited benefit and the cancer is refractory to most chemotherapeutic agents (a). Indeed, the current gold standard chemotherapy regimen of pemetrexed plus cisplatin offers a median overall survival of 12.1 months and a time to progression of 5.7 months (5).

Tumour necrosis factor (TNF)-related apoptosis-inducing ligand (TRAIL/Apo2L) is a member of the TNF ligand family that induces cell death in tumour cells in vitro and in vivo but not in most normal cells. Numerous chemotherapeutic drugs have also been shown to sensitize tumour cells to TRAIL-mediated cell death. While some mesothelioma cells are sensitive to TRAIL induced cell death others are resistant to the induction of cell death in vitro and this disruption of core-cell death machinery has been implicated in the general resistance to conventional cytotoxic agents observed clinically (ii).

Certain cancers are sensitive to the pro-cell death effects of known death receptor ligands, while others are not. Without knowledge of which cancers are sensitive to DRL-induced cell death, individuals with cancer must rely on treatment with non-specific cytotoxic therapies, such as chemotherapy, with the toxicities and problems described (5). Furthermore, with no clear indication pre-treatment of whether a patient will respond or not, the benefit of such treatment is uncertain at the outset.

There is thus a compelling need for more effective therapeutic interventions for the treatment of cancers that are sensitive to cell death caused by death receptor ligand (DRL)-induced cell death. There is also a need to provide a biomarker that can be used to identify cancerous cells that are sensitive to cell death caused by death receptor ligands when bound to death receptors, such as TRAIL-receptor 1 & 2 (Death Receptors 4& 5), TNF receptor and FAS receptor Hence, in a first aspect of the invention, there is provided a method of determining if an individual's cancer cell is sensitive to death receptor ligand (DRL)-induced cell death, the method comprising detecting, in a biological sample taken from the individual, for:

(i) the presence of a mutant BAP1 gene or mutant BAP1 protein;

(ii) a reduced level of expression of a wild-type BAP1 gene or a lower wild-type BAP1 protein concentration compared to the level of expression or protein concentration in a reference cell that is a BAP1 wildtype cell, which is resistant to DRL-induced cell death; or (iii) reduced or non-binding of an ASXL protein to a wild-type BAP1 protein compared to the level of binding in a reference cell that is a BAP1 wild-type cell, which is resistant to DRL-induced cell death;

wherein the presence, in the sample, of the mutant BAP1 gene or the mutant BAP1 protein, or of a reduced level expression of the wild-type BAP1 gene or a lower protein concentration, or reduced or non-binding of an ASXL protein to a wild-type BAP1 protein, is indicative of the individual's cancer cell being sensitive to DRL-induced cell death.

Previous genetic analyses have identified several key recurrent alterations, including inactivation of CDKN2A, NF2 and BAP1, as well as frequent losses and gains of a number of chromosomal arms. More recently, the first whole exome sequence analysis of 22 malignant mesothelioma patients confirmed the importance of these three genes as probable driver events in tumour development as well as identifying recurrent non-synonymous mutations in CUL1, an essential component of the SCF E3 ubiquitin ligase complex (6).

BAP1 is a tumour suppressor gene that is somatically mutated in a variety of cancer types including mesothelioma (7), uveal melanoma (8), renal cell carcinoma (9) and cholangiocarcinomas (10). The inventors have discovered that the expression of BAP1 mutants in cancer cells causes increased sensitivity to cell death induced by death receptor ligands, which exhibit fewer off-target effects. Tumour necrosis factor (TNF)-related apoptosis-inducing ligand (TRAIL), for example, induces cell death in tumour cells in vitro and in vivo but not in most normal cells. Advantageously, the invention therefore increases the likelihood that an individual with a cancer, which is associated with expression of a mutant BAP1 gene or synthesis of a mutant BAP1 protein, or a reduced level of expression of a wild-type BAP1 gene or a lower wild-type BAP1 protein concentration, will exhibit a positive outcome when treated with death receptor ligand therapy. Accordingly, the method of the invention provides a prognosis. Thus, such individuals are less likely to be treated with non-specific therapies and suffer the associated undesirable side-effects.

BAP1 is a deubiquitinating enzyme encoded by the BAP1 gene. It is an 80.4 kDa protein, which comprises a nuclear-localising sequence and a ubiquitin carboxy-terminal hydrolase (UCH) domain, which provides BAP1 with deubiquitinase activity. The BAP1 gene may be mutated in the germline or somatically in a variety of forms of cancer. The nucleotide sequence encoding one embodiment of the human wild-type BAP1 gene (BAP1 Whole gene sequence>gi|568815595: c52410105-52401004 *Homo sapiens* chromosome 3) is provided herein as SEQ ID No. 1, as follows:

```
                                         [SEQ ID No. 1]
GAGCGCATGCCCGCATCTGCTGTCCGACAGGCGGAAGACGAGCCCAGAGG

CGGAGCAGGGCCGTCGCGCCTTGGTGACGTCTGCCGCCGGCGCGGGCGGG

TGACGCGACTGGGCCCGTTGTCTGTGTGTGGGACTGAGGGGCCCCGGGGG

CGGTGGGGGCTCCCGGTGGGGGCAGCGGTGGGGAGGGAGGGCCTGGACAT

GGCGCTGAGGGGCCGCCCCGCGGGAAGATGAATAAGGGCTGGCTGGAGCT

GGAGAGCGACCCAGGTGAGGAGGGGACCGGGAGGGCCAGGGGCTGGGGAG

GCCGGATGGGCCCGGGACGCGCCTGCCTGACCATCACCCCCTCCTCTTGT
```

-continued

CGCCCCACCCAGGCCTCTTCACCCTGCTCGTGGAAGATTTCGGTAAGAGC

CTTTTCTCCCTGCCGGACCGGGGCTGTGGCGGCCCACCCCTGCGCCCTCA

CTCATCAGGGGCTGTCCTTCCCTACTGCTTTCCTTTCCTCATCGCAGGTG

TCAAGGGGGTGCAAGTGGAGGAGATCTACGACCTTCAGAGCAAATGTCAG

GGGTGAGTGGCTGTACACCAGGGCTGCCCCTTACACCCAGAGTGCTGGGG

AAGGTCCCAGAGAACAGGGCCCCTTAGGGAAGACAGTGCCAGGAACCCTA

CGTTGTAAAATCTCACAGAAAGCAGCAGCCTTGCTCTCTGAGTGCCCGCT

CCTGATCAAACTGATACTTTCTTTTCTCCCAAACTTTCCTTAGCGCTTCC

CTTTTTGTAGCAGCCCCCTCCCCACCCCTAAGCATCCTTTGGTTCAGCTG

CTTTCCTGGCCTTGCAGCGGGAAGACCCCGGTCACACAATGTCTTTTGTG

CAGTTGTGTAATGTATTAATTTTAGTGTGCCCATGTGTCCTTGGCTTTAA

TCCTGACACAAAGTCATCCTGTATTGATTGGTTGGGGTGACAAGGCCCCT

CCTGGGTGCCCACACTTAGAGTCTTTTCCCAGTGGTCCTGCAGAATAGAT

GTGTAAGAGAGTAGCAACAGTAGCAACCGTGACTGAACCAAGAAGTCTAC

TTTAATTTCCTGGAACAAAAGAGACTGGTGTGGGTGTTCATTTGCTTTCC

TGACTGCATTGGGGCCCACAAGTGAGAAGGAGTGCCTCAGTTCCTCATCA

GAGTTTTTGTTCTTGTCTTACTTTGTGTTCCTACCCTGTCCCATCCTTGG

CCCTCAGTTCCAGCTTTTCTTCTCTTACCCAGAACTATAGACTTCATAAG

GAGACTGGGTGGACTCCTGGAGCATCACAGTCAGAGGCTTATGCTTTGCT

CTGCCTGTGGCAGGCCTTTGGTGTGTGAGGGCACAAGGCCACTTCAGACA

CAGTGTTGGGAAGAAGCCAGGGGAGAGGGGGGATCACAGCAAGGACACCT

GAGTGATGACGCAGTGCAAAGGATTAATGGGAGAAAGAAGGGAATGCTGA

TTGTCTTCTCCCCTTTGGCTGATCTGGCTCTGCCCCTTACTTCCCCCAGC

CCTGTATATGGATTTATCTTCCTGTTCAAATGGATCGAAGAGCGCCGGTC

CCGGCGAAAGGTCTCTACCTTGGTGGATGATACGTCCGTGATTGATGATG

ATATTGTGAATAACATGTTCTTTGCCCACCAGGTCTGCTGGACTCTGTGC

TTTGTTTGGAGGGTGGGATGCTGCCATGTTTTTGCTTGGGAAGTGGAAAT

GGAGGAAGACAGGAGGAGGAGATAGGCAGATTCTAGGGGTGGTAGCTACA

GAAATCCTCTGGCAGAACGAACTGAACTCTTAATTCATTAAAGGGAACAG

CTTTAGAGTAGGAGGGTGTCTGAGTCCACTCTCTGTGTCCTCAGATATCC

AGTGGGTATTTGGTAGGTGCTTGTTAAATGAATAAACATTAGGCAAAGAT

GAAAGGAGCTGAGAAGGGGAGTTGTCCAGATATGACTGACCTGCTCTGGA

TCCCCATTCTTGATGTATATGGGCTTGGGGCTTGCAGTGAGGGGTGCTGT

GTATGGGTGACTATTCTTGGTTTCACAGCTGATACCCAACTCTTGTGCAA

CTCATGCCTTGCTGAGCGTGCTCCTGAACTGCAGCAGCGTGGACCTGGGA

CCCACCCTGAGTCGCATGAAGGACTTCACCAAGGGTTTCAGCCCTGAGGT

AGGCTGCAGTGCCTTCATCCTGGCTCACAGCCAACTGGGCAGATCTGACC

CTGAGGGCCACTGGGAATGCTACCACATGATATTGGGTACTATTAGGCTG

TTTCTTTTTCAAATGATTGTTTATGTTACATTTGACTCTTAAATAAATTG

TGTAAGGCCATTGTTTTTAGATGCAGTTGCGGGGAAAGGACACAGGCCTA

GGGAGGGAGGAGAGTTTCCTTAAGTCAGACCATGTCAGAACCTTCTCTGT

-continued

CAGGACTTTTCCTCTCAGGCCATGTTGCTTCCTAGTGTCCACTAATTACC

ATGCAAGGCCAGCACAGTCCATCTCTTTGGGGCTCCAGAGCTCTTTTCTG

CCCCCACCAGCCTTTTAAGAAAGTTCGTCTGTGTTCCTTCCGATTCCTGG

AATGCCTCCAGGCTGCTCTCTGAAGCTTTGCCTTCCACCCATAGTCCTAC

CTGAGGAGAAATTATTCTGATACGGCCTTATTTTCTTCCCCGTAGAGCAA

AGGATATGCGATTGGCAATGCCCCGGAGTTGGCCAAGGCCCATAATAGCC

ATGCCAGGTGTGTGGGAGCTGTGGAGCTGATGTGGGGTGGGAGTAGGGG

GAGTATCATTTTTTGGGCCCTGACTCTGTTTTTCCCCAGGCCCGAGCCAC

GCCACCTCCCTGAGAAGCAGAATGGCCTTAGTGCAGTGCGGACCATGGAG

GCGTTCCACTTTGTCAGCTATGTGCCTATCACAGGCCGGCTCTTTGAGCT

GGATGGGCTGAAGGTCTACCCCATTGACCATGGTAGGCACCATGAGCTGG

AGGCCTGTTGGGTGTCTCTGCCTACCTCCTAGGGAGCTGGGGCTCAGGGC

CCTCTGGTATGTGGTACCCAGTGGCAGGGGTTGTCGGTACCGACACCCGG

CTCTGGCTGGGGTTTCACCCTACACCATATTGCCCGACCAGCTCCTGATT

CCCTGGCTCAACTGCTCTTCTCTGTCTTCCTTCCCACTCCTGGCCTGCCC

AAACTCAGGGTTTCCTTCTCGCTGATTCCTTGTCTTGGTCTCCACTAGGG

CCCTGGGGGGAGGACGAGGAGTGGACAGACAAGGCCCGGCGGGTCATCAT

GGAGCGTATCGGCCTCGCCACTGCAGGGTAAGGGCCCTGTGCCTGCCCTG

TTCTACTCTCTGGAGCTGTACCTACTTTGGGAGGGACAGAGAGTATCCAG

GTGATTTGTAAATTGCAAGGCCATATGGTGAATCTGGCAAGATCAGGCTT

AGATCATGGGTTCTCAACTTGTTGTCTTATTTCCTGCCTGGGCTGCCTGT

GGCCTGCTCCTGGGTGGGCTGGGGGAGGGGCAGGCCTCAGTGGAGCCTTA

GGCAGCCCAGGTCTGCTGGTTCACTTCCAGATAGGCCCCTCATACAGCTT

GTTGGAAGGTACCAGCTCAGGTGCCTGGCATGTATGGCTAGTCGCTGCCT

GCCTGTTGGGGTGGGGCCTATACCTACAGCTGCAGGTGTGACTGCAGGGA

GCCCTGCCAGGATATCTGCCTCAACCTGATGGCGGGGCCGGGGCGGGAGC

TGCTCTCACGGCTGCGGCTGTGACTGCAGGGAGCCCTACCACGACATCCG

CTTCAACCTGATGGCAGTGGTGCCCGACCGCAGGATCAAGTATGAGGCCA

GGCTGCATGTGCTGAAGGTGAACCGTCAGACAGTACTAGAGGCTCTGCAG

CAGGTAGGTGCCCTTTCTTCCTGGCCTCTGCCCAGCCCAACCCTCCCTGC

ATTCCTCCTCCCTTCCCCCACAGCATTTGTCTCTGATTCGTGAACATACT

CTCTTGTAGATCTGGGCTTCAGCTAACCACATCTTTTCTTTGCCCCCATT

GTGGGAAAGGTGGGACTTGGAGTGGGGAGGGAGAATAGCTTCTAAAAGGA

AGTTTGGGTTTGGGTGTTTTATTTCCCTGTGAGTGAATGGGTAGAGCCAA

GGCCATTATTCCTTTAGGTCCTCAGCCCTTAGCTATTTAAGGTAGAAGCC

CGGGTCTACCCTTTCTCCTCTGAGCCCTGGATTCTGTTGTTAGCTGATAA

GAGTAACACAGCCAGAGCTGATTCAGACCCACAAGTCTCAAGAGTCACAG

CTGCCTGAGGAGTCCAAGTCAGCCAGCAACAAGTCCCCGCTGGTGCTGGA

AGCAAACAGGGCCCCTGCAGCCTCTGAGGGCAACCACACAGGTACTGGGG

GGTTTGGGACCTCTTGTGGACCTCAGAGCCACCCGCTAATGTCTGACATG

-continued

```
GGAGGCCTAAACAGGGAAAGTCTTTTTCTGGGGATGTCCTTGGGCAGTGT
TCTTCCCCCGTCAGAAGGTAGAGGGAGAGCAGTCCTTCCCTAAAGAAAGG
CACCTGTAAAGGGCCGCTGTTACCACAGGCCCCTGGGCCCTTCTCTGTAA
TGTACACTCCCTTTCTTGTTTTCTCTAGAGGCGGTTTTTTTTTTTTTTTT
TTTTTTTTTTTTTCTTCCTGCTTCTTTTTTCCCATCTCATTCTTTGCCCT
GTCTCATTGCGGGATCATGACTTAGAGCTTGCTGACTCCCATTGCACCAG
CTGGCTGGGCTGTTCTTCTCTGGGAAGTGCTGGTTCACAGGGCCGGGGAG
ACTGTGAGCTTTTCTTGGAGATCCTACTGGAGGTCCTGCCTGTGTTCTTG
CCCTGTCTCAGATGGTGCAGAGGAGGCGGCTGGTTCATGCGCACAAGCCC
CATCCCACAGCCCTCCCAACAAACCCAAGCTAGTGGTGAAGCCTCCAGGC
AGCAGCCTCAATGGGGTTCACCCCAACCCCACTCCCATTGTCCAGCGGCT
GCCGGCCTTTCTAGACAATCACAATTATGCCAAGTCCCCCATGCAGGTAA
GCTGGGAGCACCCTTGCAGGATTCTCTACTTGATTCTCTTGAGAGGCTGC
AACAGGCAATTTTCCCATGTGGTTCCTTGGTGTTCATCCTTGGCATGGCT
GGGTCAAGCTGCCTGGGCCTGGGTTGCTAGGTTCCTCTGCCTGATATGAA
AAGGCCCCCACAACAGCAGGAGCTTAGGGAGGCAGGGAGAGCTCCTTTGA
ATTTAATCTAGTTACGTGGCTGTGGGATTAAATGTTTAGGTCACGCTCCT
TGGTACAACTTCATGGGTTGGGTTTTACTGGCAAAATAAAGGCATGTGTT
TCAGGGCACTCTGTTTCTCTTAAAACCCCTCCGTGGGGTTCTATCCAGTG
TAAGTGGGTGGCAGCCTCCCCACAAGCCAAGGACAGGCCATGGAACAGCT
GGAGGGGTTCCGCTGACTCAGTCTGGAAAACCATGTTGGCTTTCTCTCTG
GCTGTGAGTGTCTAGGCTCAGCCTGGGCCGAGCAGCACTTGTTTGTAACT
GCCCTGGTCTTTGTCCCAGGAGGAAGAAGACCTGGCGGCAGGTGTGGGCC
GCAGCCGAGTTCCAGTCCGCCCACCCCAGCAGTACTCAGATGATGAGGAT
GACTATGAGGATGACGAGGAGGATGACGTGCAGAACACCAACTCTGCCCT
TAGGTCAGCCCAGCTTTCTAAGGCTACCAGGTTCTAGGTGCTTCGGATCC
CATCCTGAATATCTCAGTCTGTGTCTGAGAATGCCCTGCAGCAGATAATG
TTGAGCACCTGCGGAGTTTGGGGCCCTGGGGGAGGCTGGCATGATGGGGC
TGACCCCAGGTCCCCAGGAAGTTTTTGGTGGGCTGGGGGGTAAGGCTGAG
CACGTAAGCTTATATCATGTCCTATTGGAAGTGGCCTTTTAGCCAGGCCT
TGAAGGATTGGTTGGGGCAGGGATGGAGGAGATGTGGGTGGTGGGGAGGC
AGCTTTGCTGGAACACAGGGCATTGGCAAAAGGCCAGGAGTGGGATGGCT
GGAATAGAGGAAGTGTCTTTTGAGGACACTTGGCTGCAGCTGTCAGAACT
TGATGCCAGGCTTAGCATGGCTAGTTCAAGTTGCTTGGACCAAGTATAAG
GAGTTTTAGGGTCAGCCCCTGGAGGTCGGGATGTATTTAAGCCATTCTGG
GTACTGCTGGGTATGGTCACCTGGCCCGTTCCCTTGCTTCACATCTTCTC
GGGCCCCACAGGTATAAGGGGAAGGGAACAGGGAAGCCAGGGGCATTGAG
CGGTTCTGCTGATGGGCAACTGTCAGTGCTGCAGCCCAACACCATCAACG
TCTTGGCTGAGAAGCTCAAAGAGTCCCAGAAGGACCTCTCAATTCCTCTG
TCCATCAAGACTAGCAGCGGGGCTGGGAGTCCGGCTGTGGCAGTGCCCAC
ACACTCGCAGCCCTCACCCACCCCCAGCAATGAGAGTACAGACACGGCCT
```

-continued

```
CTGAGATCGGCAGTGCTTTCAACTCGCCACTGCGCTCGCCTATCCGCTCA
GCCAACCCGACGCGGCCCTCCAGCCCTGTCACCTCCCACATCTCCAAGGT
GCTTTTTGGAGAGGATGACAGCCTGCTGCGTGTTGACTGCATACGCTACA
ACCGTGCTGTCCGTGATCTGGGTCCTGTCATCAGCACAGGCCTGCTGCAC
CTGGCTGAGGATGGGGTGCTGAGTCCCCTGGCGCTGACAGGTGGGCCTTG
GACTGGCTCACTGGCCACTTGGTGCACCCAGGAGGGAGGAGGGAAGTGGC
CAAGTGACCACAAAGTGTCCTGCACTCTGATGATTTTCTTGTGACCTCTC
TTCCCAGAGGGTGGGAAGGGTTCCTCGCCCTCCATCAGACCAATCCAAGG
CAGCCAGGGGTCCAGCAGCCCAGTGGAGAAGGAGGTCGTGGAAGCCACGG
ACAGCAGAGAGAAGACGGGGATGGTGAGGCCTGGCGAGCCCTTGAGTGGG
GAGAAATACTCACCCAAGGTGAGCCTCCGTTGTGGTTTTCTCCTTTAATC
CTGGCAGAGGGTAAGGCCTGAGCTCCTCCTGCCCAGGTGCCAAGTTCTTG
ATTGGAACTTTGGTGTGAAGATTGGTGGCTGGAGCCATGTGCCAGAAGAC
TTTCTGGGTTGGGTGGTGGCAGGGGCCTTGATAGGCATGGACTCGCTGCT
CATCCTTGCCTCTAGCTGCCTATTGCTCGTGGGGCTTTGTTGCTGGCCCG
CCCCGATCAGAGGTGCAATGCTGGGTTTTGGCAGGAGCTGCTGGCACTGC
TGAAGTGTGTGGAGGCTGAGATTGCAAACTATGAGGCGTGCCTCAAGGAG
GAGGTAGAGAAGAGGAAGAAGTTCAAGGTGGGTGATTTCTCCAGTTGCCT
GATCTGGCCTCTCCCGAGGTCCACTGGTGGCTGCTCTGGCAAGATTGGCT
CCAGTGCTCTCAGTCTTCTTCTCTCCTACAGATTGATGACCAGAGAAGGA
CCCACAACTACGATGAGTTCATCTGCACCTTTATCTCCATGCTGGCTCAG
GAAGGTGAGGGGATGCGCTGCTGTCTTAACTGGAATGCCCTGCTGAGGGC
CGTGTCCTTCAGCTCCCCTCCCCTGGCCTCTCCTGAGGCTTGAGCAGACC
TTGGGGCACAGGGAGGGCCATGAGAGCCTCAGCTCCTGGCCTGAGGCAGC
CAGCACCTGCTCAAGGGTCTCTACCTCTTCGCAGGCATGCTGGCCAACCT
AGTGGAGCAGAACATCTCCGTGCGGCGGCGCCAAGGGGTCAGCATCGGCC
GGCTCCACAAGCAGCGGAAGCCTGACCGGCGGAAACGCTCTCGCCCCTAC
AAGGCCAAGCGCCAGTGAGGACTGCTGGCCCTGACTCTGCAGCCCACTCT
TGCCGTGTGGCCCTCACCAGGGTCCTTCCCTGCCCCACTTCCCCTTTTCC
CAGTATTACTGAATAGTCCCAGCTGGAGAGTCCAGGCCCTGGGAATGGGA
GGAACCAGGCCACATTCCTTCCATCGTGCCCTGAGGCCTGACACGGCAGA
TCAGCCCCATAGTGCTCAGGAGGCAGCATCTGGAGTTGGGGCACAGCGAG
GTACTGCAGCTTCCTCCACAGCCGGCTGTGGAGCAGCAGGACCTGGCCCT
TCTGCCTGGGCAGCAGAATATATATTTTACCTATCAGAGACATCTATTTT
TCTGGGCTCCAACCCAACATGCCACCATGTTGACATAAGTTCCTACCTGA
CTATGCTTTCTCTCCTAGGAGCTGTCCTGGTGGGCCCAGGTCCTTGTATC
ATGCCACGGTCCCAACTACAGGGTCCTAGCTGGGGGCCTGGGTGGGCCCT
GGGCTCTGGGCCCTGCTGCTCTAGCCCCAGCCACCAGCCTGTCCCTGTTG
TAAGGAAGCCAGGTCTTCTCTCTTCATTCCTCTTAGGAGAGTGCCAAACT
CAGGGACCCAGCACTGGGCTGGGTTGGGAGTAGGGTGTCCCAGTGGGGTT
```

-continued

```
GGGGTGAGCAGGCTGCTGGGATCCCATGGCCTGAGCAGAGCATGTGGGAA
CTGTTCAGTGGCCTGTGAACTGTCTTCCTTGTTCTAGCCAGGCTGTTCAA
GACTGCTCTCCATAGCAAGGTTCTAGGGCTCTTCGCCTTCAGTGTTGTGG
CCCTAGCTATGGGCCTAAATTGGGCTCTAGGTCTCTGTCCCTGGCGCTTG
AGGCTCAGAAGAGCCTCTGTCCAGCCCCTCAGTATTACCATGTCTCCCTC
TCAGGGGTAGCAGAGACAGGGTTGCTTATAGGAAGCTGGCACCACTCAGC
TCTTCCTGCTACTCCAGTTTCCTCAGCCTCTGCAAGGCACTCAGGGTGGG
GGACAGCAGGATCAAGACAACCCGTTGGAGCCCCTGTGTTCCAGAGGACC
TGATGCCAAGGGGTAATGGGCCCAGCAGTGCCTCTGGAGCCCAGGCCCCA
ACACAGCCCCATGGCCTCTGCCAGATGGCTTTGAAAAAGGTGATCCAAGC
AGGCCCCTTTATCTGTACATAGTGACTGAGTGGGGGGTGCTGGCAAGTGT
GGCAGCTGCCTCTGGGCTGAGCACAGCTTGACCCCTCTAGCCCCTGTAAA
TACTGGATCAATGAATGAATAAAACTCTCCTAAGAATCTCCTGAGAAATG
AA
```

The cDNA sequence encoding one embodiment of the human wild-t e BAP1 gene is provided herein as SEQ ID No. 2, as follows:

[SEQ ID No. 2]

```
ATGAATAAGGGCTGGCTGGAGCTGGAGAGCGACCCAGGCCTCTTCACCCT
GCTCGTGGAAGATTTCGGTGTCAAGGGGGTGCAAGTGGAGGAGATCTACG
ACCTTCAGAGCAAATGTCAGGGCCCTGTATATGGATTTATCTTCCTGTTC
AAATGGATCGAAGAGCGCCGGTCCCGGCGAAAGGTCTCTACCTTGGTGGA
TGATACGTCCGTGATTGATGATGATATTGTGAATAACATGTTCTTTGCCC
ACCAGCTGATACCCAACTCTTGTGCAACTCATGCCTTGCTGAGCGTGCTC
CTGAACTGCAGCAGCGTGGACCTGGGACCCACCCTGAGTCGCATGAAGGA
CTTCACCAAGGGTTTCAGCCCTGAGAGCAAAGGATATGCGATTGGCAATG
CCCCGGAGTTGGCCAAGGCCCATAATAGCCATGCCAGGCCCGAGCCACGC
CACCTCCCTGAGAAGCAGAATGGCCTTAGTGCAGTGCGGACCATGGAGGC
GTTCCACTTTGTCAGCTATGTGCCTATCACAGGCCGGCTCTTTGAGCTGG
ATGGGCTGAAGGTCTACCCCATTGACCATGGGCCCTGGGGGGAGGACGAG
GAGTGGACAGACAAGGCCCGGCGGGTCATCATGGAGCGTATCGGCCTCGC
CACTGCAGGGGAGCCCTACCACGACATCCGCTTCAACCTGATGGCAGTGG
TGCCCGACCGCAGGATCAAGTATGAGGCCAGGCTGCATGTGCTGAAGGTG
AACCGTCAGACAGTACTAGAGGCTCTGCAGCAGCTGATAAGAGTAACACA
GCCAGAGCTGATTCAGACCCACAAGTCTCAAGAGTCACAGCTGCCTGAGG
AGTCCAAGTCAGCCAGCAACAAGTCCCCGCTGGTGCTGGAAGCAAACAGG
GCCCCTGCAGCCTCTGAGGGCAACCACACAGATGGTGCAGAGGAGGCGGC
TGGTTCATGCGCACAAGCCCCATCCCACAGCCCTCCCAACAAACCCAAGC
TAGTGGTGAAGCCTCCAGGCAGCAGCCTCAATGGGGTTCACCCCAACCCC
ACTCCCATTGTCCAGCGGCTGCCGGCCTTTCTAGACAATCACAATTATGC
CAAGTCCCCCATGCAGGAGGAAGAAGACCTGGCGGCAGGTGTGGGCCGCA
```

-continued

```
GCCGAGTTCCAGTCCGCCCACCCCAGCAGTACTCAGATGATGAGGATGAC
TATGAGGATGACGAGGAGGATGACGTGCAGAACACCAACTCTGCCCTTAG
GTATAAGGGGAAGGGAACAGGGAAGCCAGGGGCATTGAGCGGTTCTGCTG
ATGGGCAACTGTCAGTGCTGCAGCCCAACACCATCAACGTCTTGGCTGAG
AAGCTCAAAGAGTCCCAGAAGGACCTCTCAATTCCTCTGTCCATCAAGAC
TAGCAGCGGGGCTGGGAGTCCGGCTGTGGCAGTGCCCACACACTCGCAGC
CCTCACCCACCCCCAGCAATGAGAGTACAGACACGGCCTCTGAGATCGGC
AGTGCTTTCAACTCGCCACTGCGCTCGCCTATCCGCTCAGCCAACCCGAC
GCGGCCCTCCAGCCCTGTCACCTCCCACATCTCCAAGGTGCTTTTTGGAG
AGGATGACAGCCTGCTGCGTGTTGACTGCATACGCTACAACCGTGCTGTC
CGTGATCTGGGTCCTGTCATCAGCACAGGCCTGCTGCACCTGGCTGAGGA
TGGGGTGCTGAGTCCCCTGGCGCTGACAGAGGGTGGGAAGGGTTCCTCGC
CCTCCATCAGACCAATCCAAGGCAGCCAGGGGTCCAGCAGCCCAGTGGAG
AAGGAGGTCGTGGAAGCCACGGACAGCAGAGAGAAGACGGGGATGGTGAG
GCCTGGCGAGCCCTTGAGTGGGGAGAAATACTCACCCAAGGAGCTGCTGG
CACTGCTGAAGTGTGTGGAGGCTGAGATTGCAAACTATGAGGCGTGCCTC
AAGGAGGAGGTAGAGAAGAGGAAGAAGTTCAAGATTGATGACCAGAGAAG
GACCCACAACTACGATGAGTTCATCTGCACCTTTATCTCCATGCTGGCTC
AGGAAGGCATGCTGGCCAACCTAGTGGAGCAGAACATCTCCGTGCGGCGG
CGCCAAGGGGTCAGCATCGGCCGGCTCCACAAGCAGCGGAAGCCTGACCG
GCGGAAACGCTCTCGCCCCTACAAGGCCAAGCGCCAGTGA
```

The amino acid sequence of one embodiment of human wild-type BAP1 is referred to herein as SEQ ID No. 3, as follows:

[SEQ ID No. 3]

```
MNKGWLELESDPGLFTLLVEDFGVKGVQVEEIYDLQSKCQGPVYGFIFLF
KWIEERRSRRKVSTLVDDTSVIDDDIVNNMFFAHQLIPNSCATHALLSVL
LNCSSVDLGPTLSRMKDFTKGFSPESKGYAIGNAPELAKAHNSHARPEPR
HLPEKQNGLSAVRTMEAFHFVSYVPITGRLFELDGLKVYPIDHGPWGEDE
EWTDKARRVIMERIGLATAGEPYHDIRFNLMAVVPDRRIKYEARLHVLKV
NRQTVLEALQQLIRVTQPELIQTHKSQESQLPEESKSASNKSPLVLEANR
APAASEGNHTDGAEEAAGSCAQAPSHSPPNKPKLVVKPPGSSLNGVHPNP
TPIVQRLPAFLDNHNYAKSPMQEEEDLAAGVGRSRVPVRPPQQYSDDEDD
YEDDEEDDVQNTNSALRYKGKGTGKPGALSGSADGQLSVLQPNTINVLAE
KLKESQKDLSIPLSIKTSSGAGSPAVAVPTHSQPSPTPSNESTDTASEIG
SAFNSPLRSPIRSANPTRPSSPVTSHISKVLFGEDDSLLRVDCIRYNRAV
RDLGPVISTGLLHLAEDGVLSPLALTEGGKGSSPSIRPIQGSQGSSSPVE
KEVVEATDSREKTGMVRPGEPLSGEKYSPKELLALLKCVEAEIANYEACL
KEEVEKRKKFKIDDQRRTHNYDEFICTFISMLAQEGMLANLVEQNISVRR
RQGVSIGRLHKQRKPDRRKRSRPYKAKRQ
```

Tumours arise due to mutations in proto-oncogenes or tumour suppressor genes. A gain-of-function mutation in a proto-oncogene converts it into an oncogene, which causes tumourigenesis. Such gain-of-function mutations are usually missense mutations in the DNA bases, which confer a change in the amino acid sequence, or a gain of copy number of the gene. A loss-of-function mutation in a tumour suppressor gene will also lead to tumourigenesis. A loss-of-function mutation in a tumour suppressor however is not restricted to the change of a few amino acids. Any change in an amino acid which impairs the function of the protein, results in a loss-of-function mutation. Hence, unlike oncogenes, it is not always possible to identify a specific mutation which results in the loss of function of a tumour suppressor gene. Loss-of-function truncating mutations of tumour suppressors are therefore typically identified throughout the coding exons of a gene.

BAP1 is a tumour suppressor gene. According to the invention, a mutant BAP1 gene is one that comprises a mutation. The mutant BAP1 gene is a gene that encodes a non-functional or enzymatically inactive BAP1 protein, or a BAP1 protein that exhibits reduced binding to an ASXL protein compared to the level of binding in a reference cell, which is resistant to DRL-induced cell death. Thus, a mutant BAP1 protein is one that is non-functional or enzymatically inactive or incapable of binding to an ASXL protein or exhibits reduced binding to an ASXL protein compared to the level of binding in a reference cell, which is resistant to DRL-induced cell death. As described in the Examples (see FIG. 7*d*), BAP1 has surprisingly been shown to form a complex with ASXL1, ASXL2 or ASXL3. These proteins will be collectively referred to herein as an ASXL protein.

A reduced level of expression of a wild-type BAP1 gene compared to the level of expression in a reference cell may result in a lower wild-type BAP1 protein concentration compared to the protein concentration in the same reference cell. The reduced level of expression of the wild-type BAP1 gene may be at least a 10%, 15%, 25%, 35%, 45%, 50%, 55%, 60%, 65%, 70%, 75%, 80%, 85%, 90%, 95% or a 100% reduction compared to the reference cell. Similarly, the lower concentration of wild-type BAP1 protein may be lower by at least 10%, 15%, 25%, 35%, 45%, 50%, 55%, 60%, 65%, 70%, 75%, 80%, 85%, 90%, 95% or 100% compared to the reference cell. The skilled person would know how to detect the extent of the reduction in BAP1 gene expression or lower BAP1 protein expression.

Lower expression of wild-type BAP1 protein may be caused by epigenetic silencing, methylation or low levels of BAP1 gene expression. The term "non-functional BAP1 protein" can refer to but is not limited to a BAP1 protein that does not exhibit deubiquitinase (enzyme) activity. The skilled person would appreciate that standard assays for measuring deubiquitinase activity include, but are not limited to, fluorescence assays using a fluorogenic substrate, such as ubiquitin-amidomethylcoumarin; and HPLC assays using ubiquitin ethyl ester or ubiquitin fusion peptides as model substrates to monitor deubiquitinating activity.

In one embodiment, the amino acid sequence of a mutant BAP1 gene (p.R60Q) is referred to herein as SEQ ID No. 4, as follows:

```
                                                      [SEQ ID No. 4]
  1 mnkgwleles dpglftllve dfgvkgvqve eiydlqskcq gpvygfiflf kwieerrsrq

 61 kvstlvddts vidddivnnm ffahqlipns cathallsvl lncssvdlgp tlsrmkdftk

121 gfspeskgya ignapelaka hnsharpepr hlpekqngls avrtmeafhf vsyvpitgrl

181 feldglkvyp idhgpwgede ewtdkarrvi meriglatag epyhdirfnl mavvpdrrik

241 yearlhvlkv nrqtvlealq qlirvtqpel iqthksqesq lpeesksasn ksplvleanr

301 apaasegnht dgaeeaagsc aqapshsppn kpklvvkppg sslngvhpnp tpivqrlpaf

361 ldnhnyaksp mqeeedlaag vgrsrvpvrp pqqysddedd yeddeeddvq ntnsalrykg

421 kgtgkpgals gsadgqlsvl qpntinvlae klkesqkdls iplsiktssg agspavavpt

481 hsqpsptpsn estdtaseig safnsplrsp irsanptrps spvtshiskv lfgeddsllr

541 vdcirynrav rdlgpvistg llhlaedgvl splalteggk gsspsirpiq gsqgssspve

601 kevveatdsr ektgmvrpge plsgekyspk ellallkcve aeianyeacl keevekrkkf

661 kiddqrrthn ydefictfis mlaqegmlan lveqnisvrr rqgvsigrlh kqrkpdrrkr

721 srpykakrq
```

BAP1-ASXL complexes have been shown to deubiquitinate Histone 2A, and other substrates. Inhibiting the formation of this complex renders BAP1 non-functional or enzymatically inactive.

The mutant BAP1 protein may be a full-length protein with mutations at specific loci. The mutant BAP1 protein may be a partial or complete deletion or mutation of the wild-type BAP1 protein. Partial deletion or mutation may occur in the nuclear localisation sequence (NLS), the active site of wild-type BAP1, the binding site of ASXL, or at any place in the gene that would result in the loss of function of BAP1. Mutation may include one or more point mutations. Point mutations may be a substitution, an insertion, a deletion or a frameshift mutation.

Therefore, the amino acid sequence of the mutant BAP1 protein may be encoded by SEQ ID NO. 4 or a fragment or variant thereof.

In one embodiment, the nucleotide sequence of a mutant BAP1 gene is referred to herein as SEQ ID No. 5, as follows:

```
                                         [SEQ ID No. 5]
ATGAATAAGGGCTGGCTGGAGCTGGAGAGCGACCCAGGCCTCTTCACCCT

GCTCGTGGAAGATTTCGGTGTCAAGGGGGTGCAAGTGGAGGAGATCTACG

ACCTTCAGAGCAAATGTCAGGGCCCTGTATATGGATTTATCTTCCTGTTC
```

-continued

```
AAATGGATCGAAGAGCGCCGGTCCCGGCAAAAGGTCTCTACCTTGGTGGA
TGATACGTCCGTGATTGATGATGATATTGTGAATAACATGTTCTTTGCCC
ACCAGCTGATACCCAACTCTTGTGCAACTCATGCCTTGCTGAGCGTGCTC
CTGAACTGCAGCAGCGTGGACCTGGGACCCACCCTGAGTCGCATGAAGGA
CTTCACCAAGGGTTTCAGCCCTGAGAGCAAAGGATATGCGATTGGCAATG
CCCCGGAGTTGGCCAAGGCCCATAATAGCCATGCCAGGCCCGAGCCACGC
CACCTCCCTGAGAAGCAGAATGGCCTTAGTGCAGTGCGGACCATGGAGGC
GTTCCACTTTGTCAGCTATGTGCCTATCACAGGCCGGCTCTTTGAGCTGG
ATGGGCTGAAGGTCTACCCCATTGACCATGGGCCCTGGGGGGAGGACGAG
GAGTGGACAGACAAGGCCCGGCGGGTCATCATGGAGCGTATCGGCCTCGC
CACTGCAGGGGAGCCCTACCACGACATCCGCTTCAACCTGATGGCAGTGG
TGCCCGACCGCAGGATCAAGTATGAGGCCAGGCTGCATGTGCTGAAGGTG
AACCGTCAGACAGTACTAGAGGCTCTGCAGCAGCTGATAAGAGTAACACA
GCCAGAGCTGATTCAGACCCACAAGTCTCAAGAGTCACAGCTGCCTGAGG
AGTCCAAGTCAGCCAGCAACAAGTCCCCGCTGGTGCTGGAAGCAAACAGG
GCCCCTGCAGCCTCTGAGGGCAACCACACAGATGGTGCAGAGGAGGCGGC
TGGTTCATGCGCACAAGCCCCATCCCACAGCCCTCCCAACAAACCCAAGC
TAGTGGTGAAGCCTCCAGGCAGCAGCCTCAATGGGGTTCACCCCAACCCC
ACTCCCATTGTCCAGCGGCTGCCGGCCTTTCTAGACAATCACAATTATGC
CAAGTCCCCCATGCAGGAGGAAGAAGACCTGGCGGCAGGTGTGGGCCGCA
GCCGAGTTCCAGTCCGCCCACCCCAGCAGTACTCAGATGATGAGGATGAC
TATGAGGATGACGAGGAGGATGACGTGCAGAACACCAACTCTGCCCTTAG
GTATAAGGGGAAGGGAACAGGGAAGCCAGGGGCATTGAGCGGTTCTGCTG
ATGGGCAACTGTCAGTGCTGCAGCCCAACACCATCAACGTCTTGGCTGAG
AAGCTCAAAGAGTCCCAGAAGGACCTCTCAATTCCTCTGTCCATCAAGAC
TAGCAGCGGGGCTGGGAGTCCGGCTGTGGCAGTGCCCACACACTCGCAGC
CCTCACCCACCCCCAGCAATGAGAGTACAGACACGGCCTCTGAGATCGGC
AGTGCTTTCAACTCGCCACTGCGCTCGCCTATCCGCTCAGCCAACCCGAC
GCGGCCCTCCAGCCCTGTCACCTCCCACATCTCCAAGGTGCTTTTTGGAG
AGGATGACAGCCTGCTGCGTGTTGACTGCATACGCTACAACCGTGCTGTC
CGTGATCTGGGTCCTGTCATCAGCACAGGCCTGCTGCACCTGGCTGAGGA
TGGGGTGCTGAGTCCCCTGGCGCTGACAGAGGGTGGGAAGGGTTCCTCGC
CCTCCATCAGACCAATCCAAGGCAGCCAGGGGTCCAGCAGCCCAGTGGAG
AAGGAGGTCGTGGAAGCCACGGACAGCAGAGAGAAGACGGGGATGGTGAG
GCCTGGCGAGCCCTTGAGTGGGGAGAAATACTCACCCAAGGAGCTGCTGG
CACTGCTGAAGTGTGTGGAGGCTGAGATTGCAAACTATGAGGCGTGCCTC
AAGGAGGAGGTAGAGAAGAGGAAGAAGTTCAAGATTGATGACCAGAGAAG
GACCCACAACTACGATGAGTTCATCTGCACCTTTATCTCCATGCTGGCTC
AGGAAGGCATGCTGGCCAACCTAGTGGAGCAGAACATCTCCGTGCGGCGG
CGCCAAGGGGTCAGCATCGGCCGGCTCCACAAGCAGCGGAAGCCTGACCG
GCGGAAACGCTCTCGCCCCTACAAGGCCAAGCGCCAGTGA
```

Therefore, the nucleotide sequence of the mutant BAP1 gene may be encoded by SEQ ID NO. 5 or a fragment or variant thereof.

Reduced or non-binding between an ASXL protein (ASXL1, ASXL2 or ASXL3) and a wild-type BAP1 protein may be at least a 10%, 15%, 25%, 35%, 45%, 50%, 55%, 60%, 65%, 70%, 75%, 80%, 85%, 90%, 95% or a 100% reduction compared to a reference cell in which binding between a wild-type BAP1 protein and an ASXL protein occurs. The skilled person would know how to detect the extent of the reduction in wild-type BAP1 protein binding to an ASXL protein. Standard assays for measuring binding between a wild-type BAP1 protein and an ASXL protein include but are not limited to protein complex immunoprecipitation or fluorescence resonance energy transfer (FRET).

The term "DRL-induced cell death" can refer to, but is not limited to, apoptosis and other types of cell death caused by a death receptor ligand (DRL), such as necroptosis and necrosis. Thus, the term "death receptor ligand" refers to any agent that binds to a cellular receptor and induces death of the cell on which the receptor is located. The term "cell death" can refer to cellular apoptosis, necrosis and necroptosis. Preferably, it refers to cellular apoptosis. Apoptosis refers to programmed cell death caused by activation of an apoptotic signal transduction pathway. This may be achieved through the binding of a DRL to a death receptor. Death receptor ligands may be TRAIL, TNFalpha, FAS ligand (FASL), recombinant TRAIL (dulanermin), antibodies to death receptors, especially antibodies to death receptors of the ligand TRAIL (such as mapatumuab, drozitumumab, conatumumab, lexatumumab, tigatuzumab, LBY-135), or a combination thereof.

The DRL may be an agonist molecule such as Medi-3039 or any agent that activates an apoptotic signal transduction pathway. An extrinsic apoptotic signal transduction pathway may be the FAS ligand pathway, the TNFalpha pathway or the TRAIL pathway.

The term "express(ed) or expression" can refer to a transcribed gene (i.e. DNA), or corresponding RNA that has been translated into a polypeptide or protein. Expression of a BAP1 mutant gene or BAP1 polypeptide may be detected in any compartment of the cell (e.g. in the nucleus, cytosol, the Endoplasmic Reticulum, the Golgi apparatus or the intracellular surface of the plasma membrane).

Detecting according to (i), (ii) or (iii) of the first aspect may comprise the use of any one of the following assays for detecting the presence of a gene or its corresponding protein in a sample: polymerase chain reaction (PCR); northern blotting; hybridisation-based detection techniques; flow cytometry; immunoassays, such as enzyme-linked immunosorbent assays (ELISAs), an enzyme immunoassay (EIAs), radioimmunoassay (RIAs), Western Blots, immunoprecipitation or immunohistochemistry; immunofluorescence; chromogenic (enzyme activity) assays; fluorometric imaging plate reader (FLIPR) assay; high performance liquid chromatography (HPLC) tandem mass spectrometry (MS/MS).

The biological sample is preferably a cancerous bodily sample taken from a test individual. Detection for the presence of a BAP1 mutant gene or mutant BAP1 protein in the sample is therefore preferably carried out in vitro. The sample may comprise tissue, blood, plasma, serum, spinal fluid, urine, sweat, saliva, sputum, tears, breast aspirate, prostate fluid, seminal fluid, vaginal fluid, stool, cervical scraping, amniotic fluid, intraocular fluid, mucous, moisture in breath, animal tissue, cell lysates, tumour tissue, hair, skin, buccal scrapings, nails, bone marrow, cartilage, prions, bone powder, ear wax, or combinations thereof. The sample may be a biopsy.

In another embodiment, the sample may be contained within the test subject, which may be an experimental animal (e.g. a mouse or rat) or a human, wherein the method is an in vivo based test. Alternatively, the sample may be an ex vivo sample or an in vitro sample. Therefore, the cells being tested may be in a tissue sample (for ex vivo based tests) or the cells may be grown in culture (an in vitro sample). Preferably, the biological sample is an ex vivo sample.

The inventors have developed a prognostic kit for determining a subject's sensitivity or otherwise to DRL-induced cell death.

According to a second aspect, there is provided a kit for determining if an individual's cancer cell is sensitive to DRL-induced cell death, the kit comprising detection means for detecting the expression of a mutant BAP1 gene or mutant BAP1 protein, or for detecting a reduced level of expression of a wild-type BAP1 gene or a lower wild-type BAP1 protein concentration compared to the level of expression or protein concentration in a reference cell that is resistant to DRL-induced cell death, or for detecting non-binding or reduced binding of an ASXL protein to a BAP1 protein compared to the level of binding in a reference cell that is a BAP1 wild-type cell that is resistant to DRL-induced cell death, wherein the presence, in the sample, of the mutant BAP1 gene or the BAP1 protein, or of a reduced level expression of the wild-type BAP1 gene or a lower wild-type BAP1 protein concentration, or reduced or non-binding of an ASXL protein to a wild-type BAP1 protein, is indicative of the individual's cancer cell being sensitive to DRL-induced cell death.

Preferably, the kit is used to provide a prognosis for an individual being treated with a death receptor ligand (DRL) or any agents activating the apoptotic pathways. A death receptor ligand may be TRAIL, TNFalpha, FAS ligand (FASL), recombinant TRAIL (dulanermin), death receptor antibodies (such as mapatumuab, drozitumumab, conatumumab, lexatumumab, tigatuzumab), death receptor agonists, such as Medi-3038 or Medi-3039, or a combination thereof.

Preferably, the kit comprises at least one control or reference sample. The kit may comprise a negative control and/or a positive control. A negative control may comprise a wild-type BAP1 protein that is resistant to DRL-induced cell death. A positive control may comprise a mutant BAP1 mRNA, or mutant BAP1 protein, or a blank sample. The skilled person will appreciate that the level of mRNA in a sample is indicative of the level of gene expression in a cell.

The detection means is preferably configured to detect the expression or the concentration of a mutant BAP1 protein or mRNA, or wild-type BAP1 mRNA or BAP1 protein in the biological sample taken from the test individual. The presence of the mutant BAP1 mRNA or mutant BAP1 protein, or reduced level of expression of wild-type BAP1 mRNA or lower protein expression to the control, in the sample, is indicative that the test sample is sensitive to DRL-induced cell death. The level of expression of the wild-type BAP1 mRNA or concentration of BAP1 protein in the biological sample may be reduced or lower compared to the concentration or level of expression of the wild-type BAP1 mRNA or protein in a negative control. The reduction in expression may be at least a 10%, 15%, 25%, 35%, 45%, 50%, 55%, 60%, 65%, 70%, 75%, 80%, 85%, 90%, 95% or 100% reduction compared to the negative control. Similarly, the concentration of the wild-type BAP1 protein in the biological sample may be lower by at least a 10%, 15%, 25%, 35%, 45%, 50%, 55%, 60%, 65%, 70%, 75%, 80%, 85%, 90%, 95% or 100%. Conversely, the absence of a mutant BAP1 gene or protein, or normal to high expression of the wild-type BAP1 gene or protein, in the sample, is indicative that the sample is insensitive to DRL-induced cell death.

Detection of a mutation in a BAP1 gene or protein can be achieved using a number of sequencing approaches. In one approach, whole exome or targeted gene sequencing is undertaken with massively parallel sequencing of tumour DNA with target genes enriched using commercially available RNA baits.

In another embodiment, a capillary sequencing approach is utilised with PCR primers designed to each of the exons in the BAP1 gene footprint. Thus, the detection means may be a primer.

In one embodiment, the nucleic acid sequence of a forward primer used to detect exon 12 (chr3:52438255-524388179 of wild-type BAP1 mRNA is referred to herein as SEQ ID No. 6 as follows:

[SEQ ID No. 6]
acctagaacctggtagccttag

In one embodiment, the nucleic acid sequence of a forward primer used to detect exon 8 (chr3:52440631-52441138F) of wild-type BAP1 mRNA is referred to herein as SEQ ID No. 7 as follows:

[SEQ ID No. 7]
gtacagctccagagagtagaac

In one embodiment, the nucleic acid sequence of a forward primer used to detect exon 1 (chr3:52443644-52444094F) of wild-type BAP1 mRNA is referred to herein as SEQ ID No. 8 as follows:

[SEQ ID No. 8]
tcttaccgaaatcttccacgag

In one embodiment, the nucleic acid sequence of a forward primer used to detect exon 3 (chr3:52443356-52443839F) of wild-type BAP1 mRNA is referred to herein as SEQ ID No. 9 as follows:

[SEQ ID No. 9]
ctgctgctttctgtgagatttt

In one embodiment, the nucleic acid sequence of a forward primer used to detect exon 6 (chr3:52436404-52436905F) of wild-type BAP1 mRNA is referred to herein as SEQ ID No. 10 as follows:

[SEQ ID No. 10]
agggcattccagttaagacag

In one embodiment, the nucleic acid sequence of a forward primer used to detect exon 17 (chr3:52436105-52436652F) of wild-type BAP1 mRNA is referred to herein as SEQ ID No. 11 as follows:

[SEQ ID No. 11]
caagagtgggctgcagag

In one embodiment, the nucleic acid sequence of a forward primer used to detect exon 6 (chr3:52441201-52441690) of wild-type BAP1 mRNA is referred to herein as SEQ ID No. 12 as follows:

```
[SEQ ID No. 12]
actaaggccattctgcttctc
```

In one embodiment, the nucleic acid sequence of a forward primer used to detect exon 4 (chr3:52442276-52442837F) of wild-type BAP1 mRNA is referred to herein as SEQ ID No. 13 as follows:

```
[SEQ ID No. 13]
atcccaccctccaaacaaag
```

In one embodiment, the nucleic acid sequence of a forward primer used to detect exon 13a (chr3:52437218-52437786F) of wild-type BAP1 mRNA is referred to herein as SEQ ID No. 14 as follows:

```
[SEQ ID No. 14]
caccaagtggccagtgag
```

In one embodiment, the nucleic acid sequence of a forward primer used to detect exon 13b (chr3:52437388-52437956F) of wild-type BAP1 mRNA is referred to herein as SEQ ID No. 15 as follows:

```
[SEQ ID No. 15]
ggctgtcatcctctccaaaa
```

In one embodiment, the nucleic acid sequence of a forward primer used to detect exon 13c (chr3:52437558-52438125F) of wild-type BAP1 mRNA is referred to herein as SEQ ID No. 16 as follows:

```
[SEQ ID No. 16]
gagggctgcgagtgtgtg
```

In one embodiment, the nucleic acid sequence of a forward primer used to detect exon 14 (chr3:52436940-52437529F) of wild-type BAP1 mRNA is referred to herein as SEQ ID No. 17 as follows:

```
[SEQ ID No. 17]
ctctgccaggattaaaggagaa
```

In one embodiment, the nucleic acid sequence of a forward primer used to detect exon 9 (chr3:52440055-52440607F) of wild-type BAP1 mRNA is referred to herein as SEQ ID No. 18 as follows:

```
[SEQ ID No. 18]
gaatgcagggagggttgg
```

In one embodiment, the nucleic acid sequence of a forward primer used to detect exon 5 (chr3:52441760-52442308F) of wild-type BAP1 mRNA is referred to herein as SEQ ID No. 19 as follows:

```
[SEQ ID No. 19]
acccaatatcatgtggtagcat
```

In one embodiment, the nucleic acid sequence of a forward primer used to detect exon 2 (chr3:52443516-52443974F) of wild-type BAP1 mRNA is referred to herein as SEQ ID No. 20 as follows:

```
[SEQ ID No. 20]
aaggacagcccctgatga
```

In one embodiment, the nucleic acid sequence of a forward primer used to detect exon 7 (chr3:52440976-52441547F) of wild-type BAP1 mRNA is referred to herein as SEQ ID No. 21 as follows:

```
[SEQ ID No. 21]
gtaggcagagacacccaac
```

In one embodiment, the nucleic acid sequence of a forward primer used to detect exon 15 (chr3:52436581-52437102F) of wild-type BAP1 mRNA is referred to herein as SEQ ID No. 22 as follows:

```
[SEQ ID No. 22]
ccttctctggtcatcaatctgt
```

In one embodiment, the nucleic acid sequence of a forward primer used to detect exon 10 (chr3:52439567-52440143F) of wild-type BAP1 mRNA is referred to herein as SEQ ID No. 23 as follows:

```
[SEQ ID No. 23]
ctctgaggtccacaagaggt
```

In one embodiment, the nucleic acid sequence of a forward primer used to detect exon 11 (chr3:52438912-52439525F) of wild-type BAP1 mRNA is referred to herein as SEQ ID No. 24 as follows:

```
[SEQ ID No. 24]
tcaagtagagaatcctgcaagg
```

In one embodiment, the nucleic acid sequence of a reverse primer used to detect exon 12 (chr3:52438255-52438817R) of wild-type BAP1 mRNA is referred to herein as SEQ ID No. 25 as follows:

```
[SEQ ID No. 25]
gagcagcacttgtttgtaactg
```

In one embodiment, the nucleic acid sequence of a reverse primer used to detect exon 8 (chr3:52440631-52441138R) of wild-type BAP1 mRNA is referred to herein as SEQ ID No. 26 as follows:

```
[SEQ ID No. 26]
ctcaactgctcttctagtctt
```

In one embodiment, the nucleic acid sequence of a reverse primer used to detect exon 1 (chr3:52443644-52444094R) of wild-type BAP1 mRNA is referred to herein as SEQ ID No. 27 as follows:

```
[SEQ ID No. 27]
gagggagggcctggacat
```

In one embodiment, the nucleic acid sequence of a reverse primer used to detect exon 3 (chr3:52443356-52443839R) of wild-type BAP1 mRNA is referred to herein as SEQ ID No. 28 as follows:

[SEQ ID No. 28]
ctgtccttccctactgctttc

In one embodiment, the nucleic acid sequence of a reverse primer used to detect exon 16 (chr3:52436404-52436905R) of wild-type BAP1 mRNA is referred to herein as SEQ ID No. 29 as follows:

[SEQ ID No. 29]
gaagttcaaggtgggtgatttc

In one embodiment, the nucleic acid sequence of a reverse primer used to detect exon 17 (chr3:52436105-52436652R) of wild-type BAP1 mRNA is referred to herein as SEQ ID No. 30 as follows:

[SEQ ID No. 30]
ctcagctcctggcctgag

In one embodiment, the nucleic acid sequence of a reverse primer used to detect exon 6 (chr3:52441201-52441691R) of wild-type BAP1 mRNA is referred to herein as SEQ ID No. 31 as follows:

[SEQ ID No. 31]
ggagaaattattctgatacggcc

In one embodiment, the nucleic acid sequence of a reverse primer used to detect exon 4 (chr3:52442276–52442837R) of wild-type BAP1 mRNA is referred to herein as SEQ ID No. 32 as follows:

[SEQ ID No. 32]
gaagggaatgctgattgtcttc

In one embodiment, the nucleic acid sequence of a reverse primer used to detect exon 13a (chr3:52437218-52437786R) of wild-type BAP1 mRNA is referred to herein as SEQ ID No. 33 as follows:

[SEQ ID No. 33]
ctatccgctcagccaacc

In one embodiment, the nucleic acid sequence of a reverse primer used to detect exon 13b (chr3:52437388-52437956R) of wild-type BAP1 mRNA is referred to herein as SEQ ID No. 34 as follows:

[SEQ ID No. 34]
ctctcaattcctctgtccatca

In one embodiment, the nucleic acid sequence of a reverse primer used to detect exon 13c (chr3:52437558-52438125R) of wild-type BAP1 mRNA is referred to herein as SEQ ID No. 35 as follows:

[SEQ ID No. 35]
cgttcccttgcttcacatct

In one embodiment, the nucleic acid sequence of a reverse primer used to detect exon 14 (chr3:52436940-52437529R) of wild-type BAP1 mRNA is referred to herein as SEQ ID No. 36 as follows:

[SEQ ID No. 36]
tcctgcactctgatgattttct

In one embodiment, the nucleic acid sequence of a reverse primer used to detect exon 9 (chr3:52440055-52440607R) of wild-type BAP1 mRNA is referred to herein as SEQ ID No. 37 as follows:

[SEQ ID No. 37]
gatatctgcctcaacctgatgg

In one embodiment, the nucleic acid sequence of a reverse primer used to detect exon 5 (chr3:52441760-52442308R) of wild-type BAP1 mRNA is referred to herein as SEQ ID No. 38 as follows:

[SEQ ID No. 38]
gtgctgtgtatgggtgacta

In one embodiment, the nucleic acid sequence of a reverse primer used to detect exon 2 (chr3:52443516-52443974R) of wild-type BAP1 mRNA is referred to herein as SEQ ID No. 39 as follows:

[SEQ ID No. 39]
gaagatgaataagggctggct

In one embodiment, the nucleic acid sequence of a reverse primer used to detect exon 7 (chr3:52440976-52441547R) of wild-type BAP1 mRNA is referred to herein as SEQ ID No. 40 as follows:

[SEQ ID No. 40]
tgatgtggggtgggagtag

In one embodiment, the nucleic acid sequence of a reverse primer used to detect exon 15 (chr3:52436581-52437102R) of wild-type BAP1 mRNA is referred to herein as SEQ ID No. 41 as follows:

[SEQ ID No. 41]
cccgatcagaggtgcaat

In one embodiment, the nucleic acid sequence of a reverse primer used to detect exon 10 (chr3:52439567-52440143R) of wild-type BAP1 mRNA is referred to herein as SEQ ID No. 42 as follows:

[SEQ ID No. 42]
agctatttaaggtagaagcccg

In one embodiment, the nucleic acid sequence of a reverse primer used to detect exon 11 (chr3:52438912-52439525R) of wild-type BAP1 mRNA is referred to herein as SEQ ID No. 43 as follows:

[SEQ ID No. 43]
actgtgagcttttcttggagat

The skilled person would appreciate that the binding of an ASXL protein to a wild-type BAP1 protein may be achieved using a variety of techniques known in the art, which include protein complex immunoprecipitation, Bimolecular Fluorescence complementation, Affinity electrophoresis, Immuno-electrophoresis, chemical cross linking, Proximity ligation assay and FRET.

The inventors believe that their findings (i.e. that cells containing a mutant BAP1 gene or a mutant BAP1 protein, or cells expressing reduced levels of a wild-type BAP1 gene or with a lower concentration of BAP1 protein, are sensitive to DRL-induced cell death) means that they have identified a robust biomarker for sensitivity to DRL-induced cell death.

Therefore, in a third aspect of the invention, there is provided a use of (i) a mutant BAP1 gene or a mutant BAP1 protein, or (ii) a cancer cell with a reduced level of expression of a wild-type BAP1 gene or a lower wild-type BAP1 protein concentration compared to the level of expression or protein concentration in a reference cell that is a BAP1 wild-type cell, as a biomarker of sensitivity to DRL-induced cell death.

The inventors have developed a method of treating subjects suffering from cancer, and especially those suffering from a cancer that is completely or partially insensitive to death receptor ligand-induced cell death.

In a fourth aspect, therefore, there is provided a method of treating an individual suffering from cancer, the method comprising:

(i) detecting for the presence of a mutant BAP1 gene or mutant BAP1 protein, or for a reduced level of expression of a wild-type BAP1 gene or a lower wild-type BAP1 protein concentration compared to the level of expression or protein concentration in a reference cell that is a BAP1 wild-type cell that is resistant to DRL-induced cell death, or for reduced or non-binding of an ASXL protein to a wild-type BAP1 protein compared to the level of binding in a reference cell that is a BAP1 wild-type cell, which is resistant to DRL-induced cell death; and (ii) administering a therapeutically effective amount of a death receptor ligand to the individual.

The death receptor ligand may be administered as a monotherapy or in combination with other agents that are capable of killing cancer cells.

The "subject" or "individual" may be a vertebrate, mammal, or domestic animal. Hence, medicaments according to the invention may be used to treat any mammal, for example livestock (e.g. a horse), pets, or may be used in other veterinary applications. Most preferably, the subject is a human being.

As mentioned above, mesothelioma cells are resistant to the induction of cell death. This disruption of core-cell death machinery has been implicated in the resistance to conventional cytotoxic agents generally observed clinically. It is believed that disruption of cell death machinery is mediated downstream through elevated expression of anti-cell death proteins such as members of the IAP (inhibitors of apoptosis) family or the BCL-2 family. The IAP family consist of 8 members (BIRC2, BIRC3, BIRC5, BIRC6, BIRC7, BIRC8, NAIP, XIAP). The defining feature of an IAP protein is the presence of a ~70-amino acid baculovirus IAP repeat (BIR) domain that mediates protein-protein interactions (12). Through these domains, IAP members act as endogenous inhibitors of caspases, the main executioners of cell death, and act through either direct caspase inhibition or ubiquitin-mediated regulation of caspase degradation (13).

The inventors have demonstrated that BAP1 gene expression can be reduced in mesothelioma cell lines using a BAP1 shRNA-expressing lentivirus and that this reduction of BAP1 gene expression results in increased sensitivity to DLR-induced cell death in these cell lines. Accordingly, the inventors have determined that it is possible to sensitise to DRL-induced cell death, an individual suffering from a cancer that is normally insensitive to DRL-induced cell death, by administering a BAP1 inhibitor.

Thus, in a fifth aspect of the invention, there is provided a method of:

sensitising, to DRL-induced cell death, an individual that is suffering from a cancer that is insensitive to DRL-induced cell death, or enhancing the sensitivity to DRL-induced cell death in an individual that is suffering from a cancer that is sensitive to DRL-induced cell death, the method comprising administering, to the individual, a BAP1 inhibitor or an agent that mimics the effect of BAP1 inhibition.

Thus, a BAP1 inhibitor is any agent that targets the BAP1 gene or protein directly, whereas an agent that mimics the effect of BAP1 inhibition is a molecule that targets a signalling molecule downstream of the BAP1 gene/protein signalling pathway.

A BAP1 inhibitor may be any molecule that inactivates BAP1 protein function, such as a deubiquitinase inhibitor or antagonist, or which silences or reduces BAP1 gene or protein expression or function (such as a small molecule inhibitor of BAP1), or which prevents or reduces binding of a wild-type BAP1 protein to an ASXL protein. The BAP1 inhibitor or agent may also be any molecule that mutates a wild-type BAP1 gene to create a mutant BAP1 gene. Thus, the BAP1 inhibitor or agent may be an RNAi molecule, including shRNA, siRNA, miRNA, ribozymes and antisense molecules; a TALEN (Transcriptional Activator Like-Effector Nuclease); or a CRISPR/CAS9 nuclease. The inventors have demonstrated in the Examples below that BAP1 gene expression can be reduced in mesothelioma cell lines using shRNA expressing lentivirus and that this reduction of BAP1 gene expression results in increased sensitivity to DLR-induced cell death in these cell lines.

In addition to a BAP1 inhibitor, an agent that mimics the effect of BAP1 inhibition is an agent that targets signalling or effector molecules downstream of BAP1, such agents may be used to induce DLR resistance in cancer cell. In one embodiment, the BAP1 inhibitor may be an IAP inhibitor (a SMAC mimetic). An IAP may be BIRC2, BIRC3, BIRC5, BIRC6, BIRC7, BIRC8, NAIP, XIAP or a fragment thereof. The inventors have found that BAP1 expression increases the expression of BIRC3 protein and that inhibition of BIRC3 protein with an IAP inhibitor, such as LCL161, results in sensitization to DRL induced cell death. An IAP inhibitor is an agent that reduces expression or translation of an IAP, or renders an IAP functionally inactive. The IAP inhibitor or agent may also be any molecule that mutates an IAP gene or protein to create a mutant IAP gene or protein. Thus, the IAP1 inhibitor or agent may be an RNAi molecule, including shRNA, siRNA, miRNA, ribozymes and antisense molecules; a TALEN (Transcriptional Activator Like-Effector Nuclease); or a CRISPR/CAS9 nuclease. An agent that mimics the effect of BAP1 inhibition may be an RNA helicase inhibitor, such as, YK-4279 or a tyrosine kinase inhibitor, such as sorafenib.

The inventors believe that their surprising observation (i.e. that BAP1 plays a role in regulating DRL-induced cell death of cancer cells) can be used to develop a novel targeted approach for treatment of any cancer comprising mutants of BAP1.

Thus, in a sixth aspect of the invention, there is provided a composition comprising (i) a BAP1 inhibitor or an agent that mimics the effect of BAP1 inhibition and (ii) a death receptor ligand.

In a seventh aspect, there is provided a composition comprising (i) a BAP1 inhibitor or an agent that mimics the effect of BAP1 inhibition and (ii) a death receptor ligand, for use in therapy or as a medicament.

In an eighth aspect, there is provided a composition comprising (i) a BAP1 inhibitor or an agent that mimics the effect of BAP1 inhibition and (ii) a death receptor ligand, for use in treating, preventing or ameliorating cancer.

In a ninth aspect, there is provided a method of treating, preventing or ameliorating an individual suffering from a cancer, the method comprising administering, to the individual, a therapeutically effective amount of the composition of the sixth aspect.

The BAP1 inhibitor or agent that mimics the effect of BAP1 inhibition and the death receptor ligand may be administered simultaneously, or the BAP1 inhibitor may be administered prior to the death receptor ligand.

It will be appreciated that administration of the BAP1 inhibitor first sensitizes the subject to DRL-induced cell death. Then, administration of the death receptor ligand can be effectively used to induce cell death in cancerous cells.

Preferably, the BAP1 inhibitor is any molecule or approach which inactivates BAP1 protein function, such as a deubiquitinase inhibitor or antagonist, or which silences or reduces BAP1 gene transcription or BAP1 protein expression, or which mutates a wild-type BAP1 gene to create a BAP1 mutant gene and protein. The BAP1 inhibitor may be WP1130, Usp9x, Usp5, Usp14, Usp24, UCH37, b-AP15, CRISPR/CAS9 or a small molecule inhibitor of BAP1.

Preferred death receptor ligands may be, but are not limited to TRAIL, TNFalpha, FAS ligand (FASL), recombinant TRAIL (dulanermin), death receptor antibodies (such as mapatumuab, drozitumumab, conatumumab, lexatumumab, tigatuzumab, LBY-135) or death receptor agonists such as Medi 3038 or Medi 3039, or a combination thereof.

Mesothelioma (or Malignant Pleural Mesothelioma) is a rare form of cancer that develops from cells of the mesothelium, the protective lining that covers many of the internal organs of the body. The most common anatomical site for mesothelioma is the pleura (the outer lining of the lungs and internal chest wall), but it can also arise in the peritoneum (the lining of the abdominal cavity), the pericardium (the sac that surrounds the heart) or the tunica vaginalis (a sac that surrounds the testis). Thus, the cancer which may be treated according to any aspect of the invention may be selected from mesothelioma, Malignant Pleural Mesothelioma, uveal melanoma, melanoma, non-melanoma skin cancer, renal cancers, cholangiocarcinomas, lung cancers, cancer of the pleura, abdominal cancer, peritoneal cancer, cancer of the pericardium, head and neck cancers, brain cancers, breast cancers, liver and biliary tract cancers, gastrointestinal cancers including upper and lower tracts, urothelial cancers, prostate cancers, testicular cancer, cancer of the tunica vaginalis, ovarian cancers, cervical cancers, sarcomas, lymphomas and leukaemia.

More preferably, the cancer which is treated is mesothelioma. Most preferably, the cancer which is treated is an asbestos-induced cancer.

The compositions according to the invention may have a number of different forms depending, in particular, on the manner in which the composition is to be used. Thus, for example, the composition may be in the form of a powder, tablet, capsule, liquid, ointment, cream, gel, hydrogel, aerosol, spray, micellar solution, transdermal patch, liposome suspension or any other suitable form that may be administered to a person or animal in need of treatment. It will be appreciated that the vehicle of medicaments according to the invention should be one which is well tolerated by the subject to whom it is given.

Compositions according to the invention may be used in a number of ways. For instance, oral administration may be required, in which case the agents may be contained within a composition that may, for example, be ingested orally in the form of a tablet, capsule or liquid. Compositions comprising agents of the invention may be administered by inhalation (e.g. intranasally). Compositions may also be formulated for topical use. For instance, creams or ointments may be applied to the skin.

Agents or compositions according to the invention may also be incorporated within a slow- or delayed-release device. Such devices may, for example, be inserted on or under the skin, and the medicament may be released over weeks or even months. The device may be located at least adjacent to the treatment site. Such devices may be particularly advantageous when long-term treatment with agents used according to the invention is required and which would normally require frequent administration (e.g. at least daily injection).

In a preferred embodiment, compositions and agents according to the invention may be administered to a subject by injection into the blood stream or directly into a site requiring treatment. For example, the medicament may be injected at least adjacent to a sensitive cell, or within a tumour. Injections may be intravenous (bolus or infusion) or subcutaneous (bolus or infusion), or intradermal (bolus or infusion), or intrapleural.

It will be appreciated that the amount of the composition and agent that is required is determined by its biological activity and bioavailability, which in turn depends on the mode of administration, the physicochemical properties of the modulator and whether it is being used as a monotherapy or in a combined therapy. The frequency of administration will also be influenced by the half-life of the BAP1 inhibitors and DRLs within the subject being treated. Optimal dosages to be administered may be determined by those skilled in the art, and will vary with the particular agent in use, the strength of the pharmaceutical composition, the mode of administration, and the advancement of the cancer. Additional factors depending on the particular subject being treated will result in a need to adjust dosages, including subject age, weight, gender, diet, and time of administration.

Generally, a daily dose of between 0.01 μg/kg of body weight and 500 mg/kg of body weight of the agents (e.g. the inhibitor or the DRL) according to the invention may be used for treating, ameliorating, or preventing cancer, depending upon which agent is used. More preferably, the daily dose is between 0.01 mg/kg of body weight and 400 mg/kg of body weight, more preferably between 0.1 mg/kg and 200 mg/kg body weight, and most preferably between approximately 1 mg/kg and 100 mg/kg body weight.

The composition or agent(s) may be administered before, during or after onset of the cancer. Daily doses may be given as a single administration (e.g. a single daily injection). Alternatively, the agent may require administration twice or more times during a day. As an example, agents may be administered as two (or more depending upon the severity of the disease being treated) daily doses of between 25 mg and 7000 mg (i.e. assuming a body weight of 70 kg). A subject receiving treatment may take a first dose upon waking and then a second dose in the evening (if on a two dose regime) or at 3- or 4-hourly intervals thereafter. Alternatively, a slow release device may be used to provide optimal doses of agents according to the invention to a patient without the need to administer repeated doses.

Known procedures, such as those conventionally employed by the pharmaceutical industry (e.g. in vivo experimentation, clinical trials, etc.), may be used to form specific formulations comprising the agents according to the invention and precise therapeutic regimes (such as daily doses of the agents and the frequency of administration). The inventors believe that they are the first to describe a pharmaceutical composition for treating cancer, based on the use of a BAP1 inhibitor to sensitise the subject to death receptor-induced cell death, and a death receptor ligand, which induces cell death of the cells that express death receptors and previously insensitive to death receptor-induced cell death.

According to a tenth aspect, there is provided a pharmaceutical composition comprising the composition according to the sixth aspect, and a pharmaceutically acceptable vehicle.

According to an eleventh aspect, there is provided a method for preparing the pharmaceutical composition according to the tenth aspect, the method comprising contacting a therapeutically effective amount of a BAP1 inhibitor or agent that mimics the effect of BAP1 inhibition and a death receptor ligand, and a pharmaceutically acceptable vehicle.

A "therapeutically effective amount" of BAP1 inhibitor is any amount which, when administered to a subject, is the amount needed to sensitise an individual's cells to death receptor-induced cell death. A "therapeutically effective amount" of death receptor ligand is any amount which, when administered to a subject, is the amount needed to treat the cancer, or produce the desired effect.

For example, the therapeutically effective amount of active agent (i.e. BAP1 inhibitor and a death receptor ligand) used may be from about 0.01 mg/kg body weight to about 800 mg/kg body weight, and preferably from about 0.01 mg to about 500 mg. It is preferred that the amount of agent is an amount from about 0.1 mg to about 250 mg, and most preferably from about 0.1 mg/kg body weight to about 20 mg/kg body weight.

A "pharmaceutically acceptable vehicle" as referred to herein, is any known compound or combination of known compounds that are known to those skilled in the art to be useful in formulating pharmaceutical compositions.

In one embodiment, the pharmaceutically acceptable vehicle may be a solid, and the composition may be in the form of a powder or tablet. A solid pharmaceutically acceptable vehicle may include one or more substances which may also act as flavouring agents, lubricants, solubilisers, suspending agents, dyes, fillers, glidants, compression aids, inert binders, sweeteners, preservatives, dyes, coatings, or tablet-disintegrating agents. The vehicle may also be an encapsulating material. In powders, the vehicle is a finely divided solid that is in admixture with the finely divided active agents according to the invention. In tablets, the active agent (e.g. the peptide, antibody, DRL or BAP1 inhibitor) may be mixed with a vehicle having the necessary compression properties in suitable proportions and compacted in the shape and size desired. The powders and tablets preferably contain up to 99% of the active agents. Suitable solid vehicles include, for example calcium phosphate, magnesium stearate, talc, sugars, lactose, dextrin, starch, gelatin, cellulose, polyvinylpyrrolidone, low melting waxes and ion exchange resins. In another embodiment, the pharmaceutical vehicle may be a gel and the composition may be in the form of a cream or the like.

However, the pharmaceutical vehicle may be a liquid, and the pharmaceutical composition is in the form of a solution. Liquid vehicles are used in preparing solutions, suspensions, emulsions, syrups, elixirs and pressurized compositions. The active agent according to the invention may be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilizers or osmo-regulators. Suitable examples of liquid vehicles for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the vehicle can also be an oily ester such as ethyl oleate and isopropyl myristate. Sterile liquid vehicles are useful in sterile liquid form compositions for parenteral administration. The liquid vehicle for pressurized compositions can be a halogenated hydrocarbon or other pharmaceutically acceptable propellant.

Liquid pharmaceutical compositions, which are sterile solutions or suspensions, can be utilised by, for example, intramuscular, intrathecal, epidural, intraperitoneal, intravenous and particularly subcutaneous injection. The composition or antibody may be prepared as a sterile solid composition that may be dissolved or suspended at the time of administration using sterile water, saline, or other appropriate sterile injectable medium.

The agents and compositions of the invention may be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. The agent or composition according to the invention can also be administered orally either in liquid or solid composition form. Compositions and agents suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

It will be appreciated that the invention extends to any nucleic acid or peptide or variant, derivative or analogue thereof, which comprises substantially the amino acid or nucleic acid sequences of any of the sequences referred to herein, including variants or fragments thereof. The terms "substantially the amino acid/nucleotide/peptide sequence", "variant" and "fragment", can be a sequence that has at least 40% sequence identity with the amino acid/nucleotide/peptide sequences of any one of the sequences referred to herein, for example 40% identity with the polypeptide identified as SEQ ID Nos. 3 or 4, and so on.

Amino acid/polynucleotide/polypeptide sequences with a sequence identity which is greater than 50%, more preferably greater than 65%, 70%, 75%, and still more preferably greater than 80% sequence identity to any of the sequences referred to are also envisaged. Preferably, the amino acid/polynucleotide/polypeptide sequence has at least 85% identity with any of the sequences referred to, more preferably at least 90%, 92%, 95%, 97%, 98%, and most preferably at least 99% identity with any of the sequences referred to herein.

The skilled technician will appreciate how to calculate the percentage identity between two amino acid/polynucleotide/polypeptide sequences. In order to calculate the percentage identity between two amino acid/polynucleotide/polypeptide sequences, an alignment of the two sequences must first be prepared, followed by calculation of the sequence identity value. The percentage identity for two sequences may take different values depending on:—(i) the method used to align the sequences, for example, ClustalW, BLAST, PASTA, Smith-Waterman (implemented in different programs), or structural alignment from 3D comparison; and (ii) the parameters used by the alignment method, for example, local vs global alignment, the pair-score matrix used (e.g. BLOSUM62, PAM250, Gonnet etc.), and gap-penalty, e.g. functional form and constants.

Having made the alignment, there are many different ways of calculating percentage identity between the two sequences. For example, one may divide the number of identities by: (i) the length of shortest sequence; (ii) the length of alignment; (iii) the mean length of sequence; (iv) the number of non-gap positions; or (iv) the number of equivalenced positions excluding overhangs. Furthermore, it will be appreciated that percentage identity is also strongly length dependent. Therefore, the shorter a pair of sequences is, the higher the sequence identity one may expect to occur by chance. Hence, it will be appreciated that the accurate alignment of protein or DNA sequences is a complex process. The popular multiple alignment program ClustalW (Thompson et al., 1994, Nucleic Acids Research, 22, 4673-4680; Thompson et al., 1997, Nucleic Acids Research, 24, 4876-4882) is a preferred way for generating multiple alignments of proteins or DNA in accordance with the invention. Suitable parameters for ClustalW may be as follows: For DNA alignments: Gap Open Penalty=15.0, Gap Extension Penalty=6.66, and Matrix=Identity. For protein alignments: Gap Open Penalty=10.0, Gap Extension Penalty=0.2, and Matrix=Gonnet. For DNA and Protein alignments: ENDGAP=−1, and GAPDIST=4. Those skilled in the art will be aware that it may be necessary to vary these and other parameters for optimal sequence alignment. Preferably, calculation of percentage identities between two amino acid/polynucleotide/polypeptide sequences may then be calculated from such an alignment as (N/T)*100, where N is the number of positions at which the sequences share an identical residue, and T is the total number of positions compared including gaps but excluding overhangs. Hence, a most preferred method for calculating percentage identity between two sequences comprises (i) preparing a sequence alignment using the ClustalW program using a suitable set of parameters, for example, as set out above; and (ii) inserting the values of N and T into the following formula:—

$$\text{Sequence Identity}=(N/T)*100.$$

Alternative methods for identifying similar sequences will be known to those skilled in the art. For example, a substantially similar nucleotide sequence will be encoded by a sequence which hybridizes to any sequences referred to herein or their complements under stringent conditions. By stringent conditions, we mean the nucleotide hybridises to filter-bound DNA or RNA in 3× sodium chloride/sodium citrate (SSC) at approximately 45° C. followed by at least one wash in 0.2×SSC/0.1% SDS at approximately 20-65° C. Alternatively, a substantially similar polypeptide may differ by at least 1, but less than 5, 10, 20, 50 or 100 amino acids from the sequences shown in SEQ ID Nos. 3 or 4.

Due to the degeneracy of the genetic code, it is clear that any nucleic acid sequence described herein could be varied or changed without substantially affecting the sequence of the protein encoded thereby, to provide a variant thereof. Suitable nucleotide variants are those having a sequence altered by the substitution of different codons that encode the same amino acid within the sequence, thus producing a silent change. Other suitable variants are those having homologous nucleotide sequences but comprising all, or portions of, sequence, which are altered by the substitution of different codons that encode an amino acid with a side chain of similar biophysical properties to the amino acid it substitutes, to produce a conservative change. For example small non-polar, hydrophobic amino acids include glycine, alanine, leucine, isoleucine, valine, proline, and methionine. Large non-polar, hydrophobic amino acids include phenylalanine, tryptophan and tyrosine. The polar neutral amino acids include serine, threonine, cysteine, asparagine and glutamine. The positively charged (basic) amino acids include lysine, arginine and histidine. The negatively charged (acidic) amino acids include aspartic acid and glutamic acid. It will therefore be appreciated which amino acids may be replaced with an amino acid having similar biophysical properties, and the skilled technician will know the nucleotide sequences encoding these amino acids.

All of the features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying diagrammatic drawings, in which:—

Figure 1B:
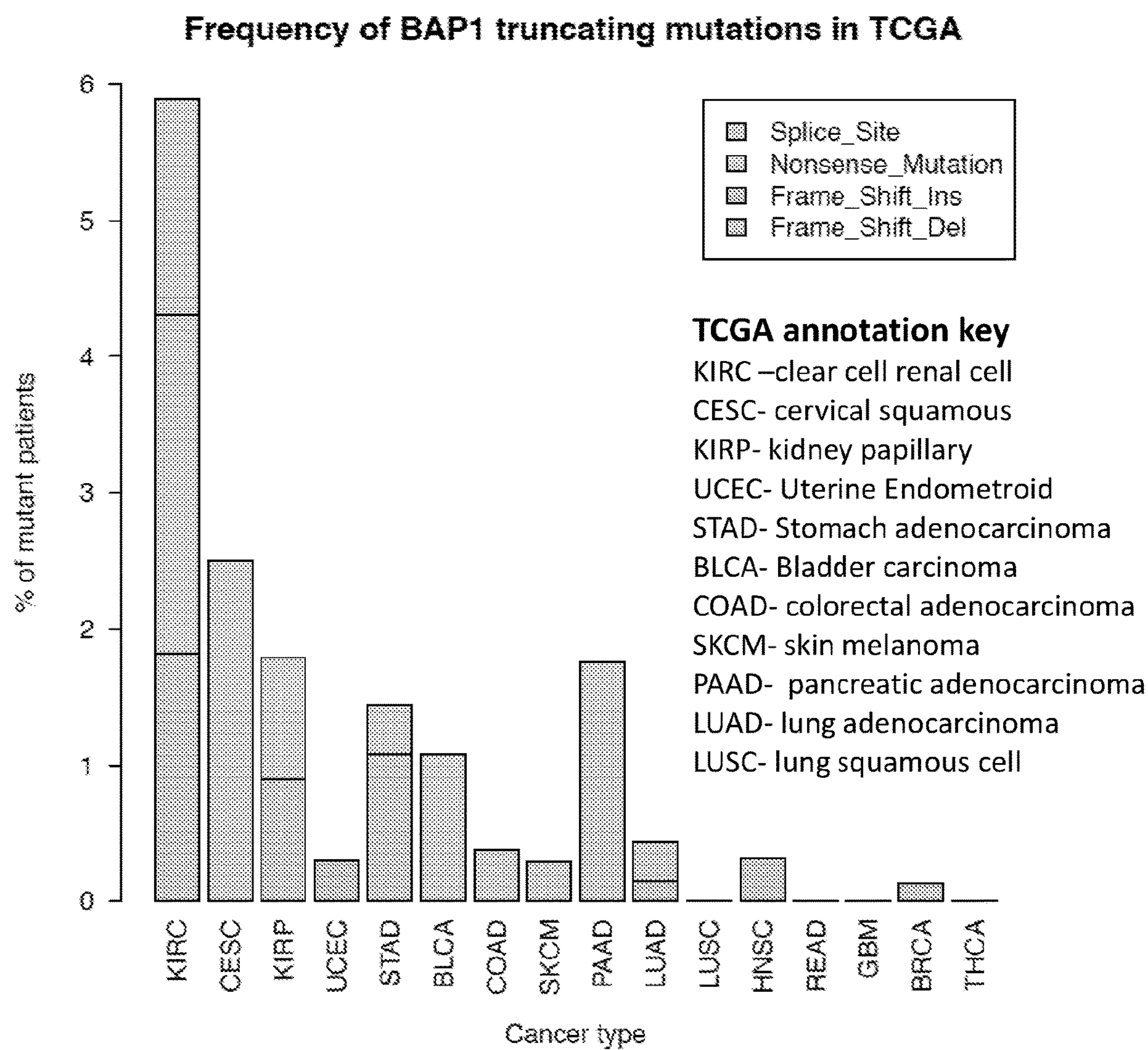
Figure 1C:
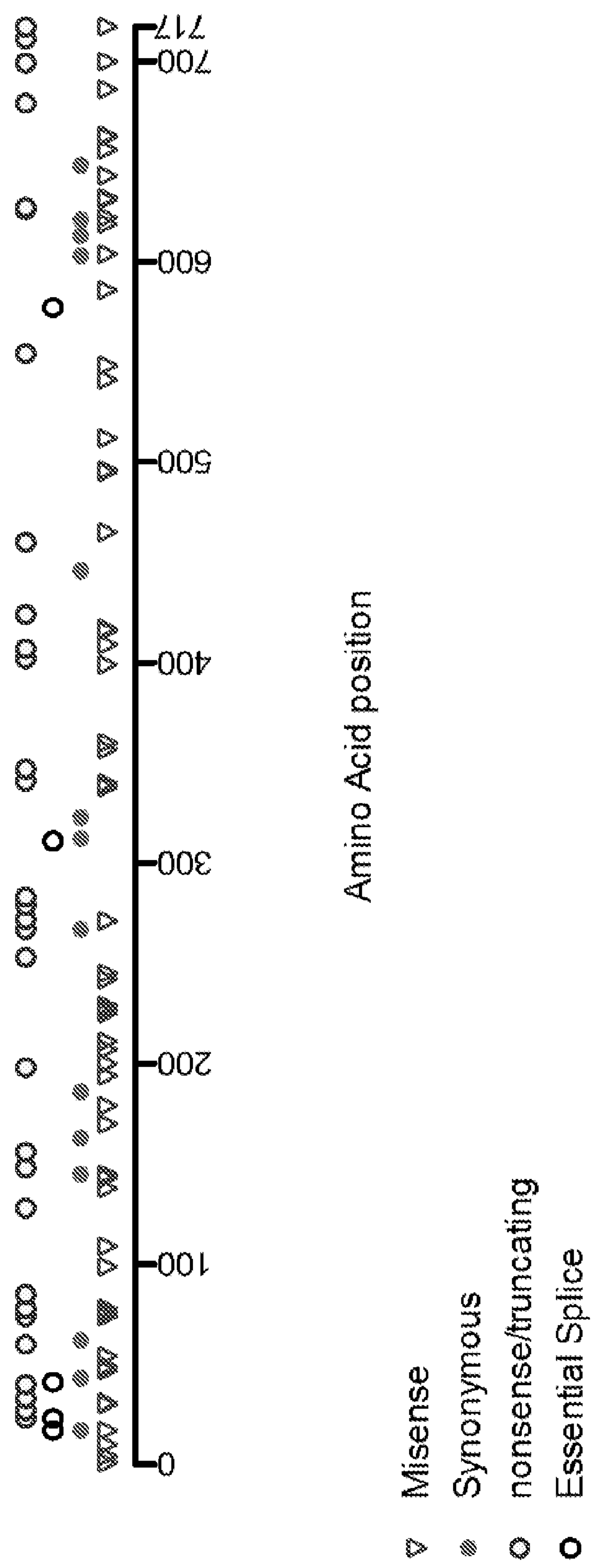

FIG. 1A shows various types of mutations in different malignant pleural mesothelioma (MPM) cell lines. FIG. 1B is an analysis of TCGA exomes for enrichment of BAP1 loss of function mutations. FIG. 1*s* is a schematic of BAP1 gene exons with Mutations annotated from 5180 TCGA exomes.

Figure 2A:
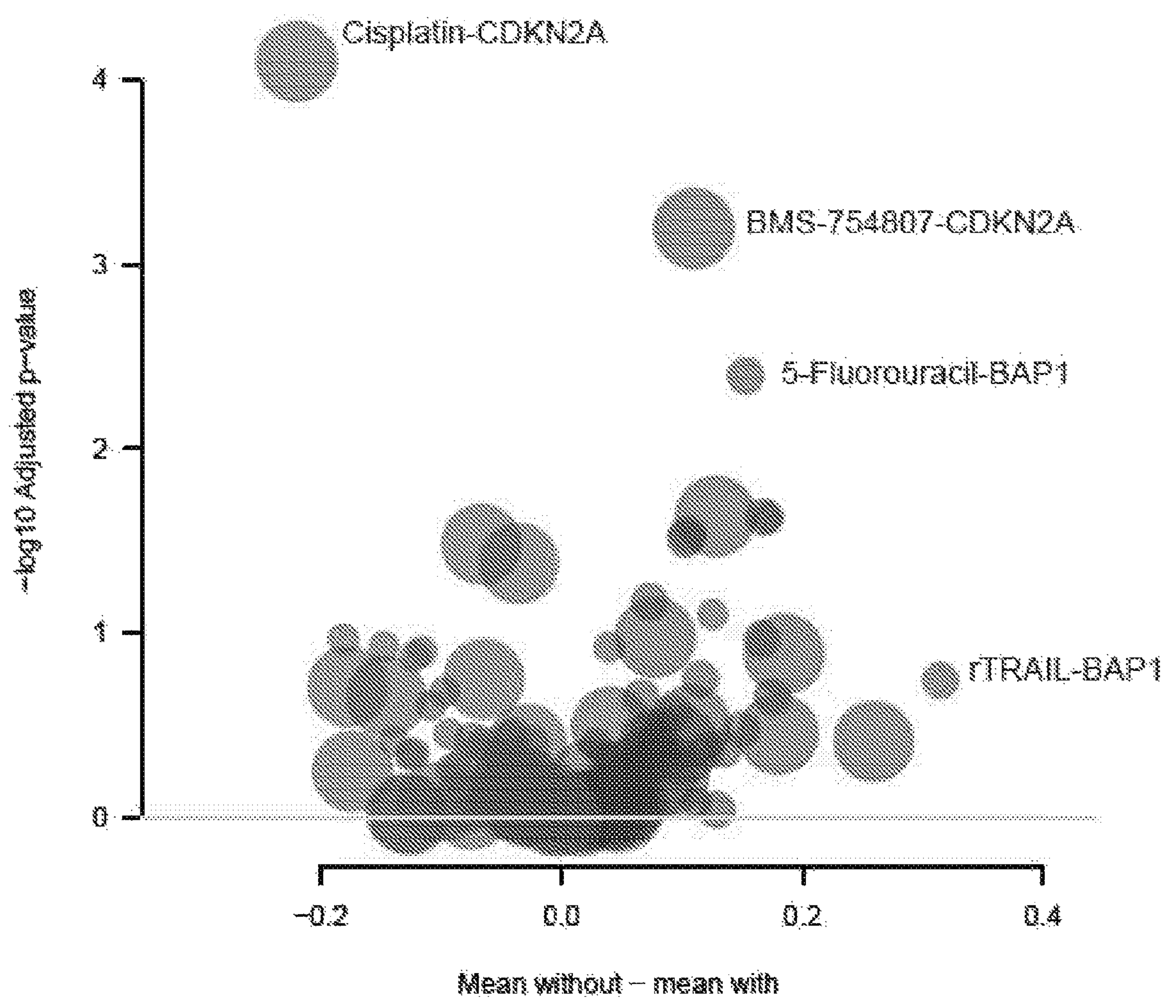
Figure 2B:
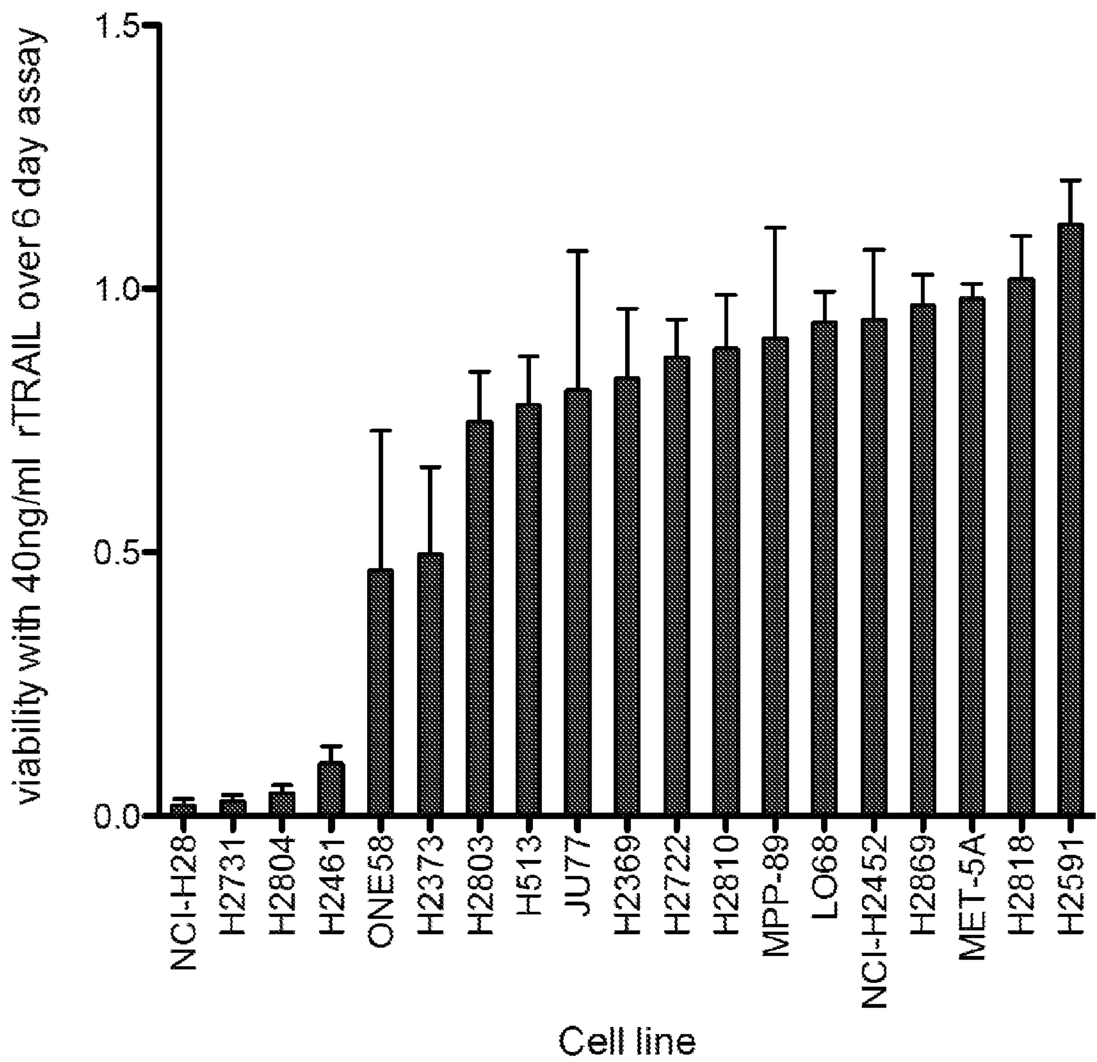
Figure 2C:
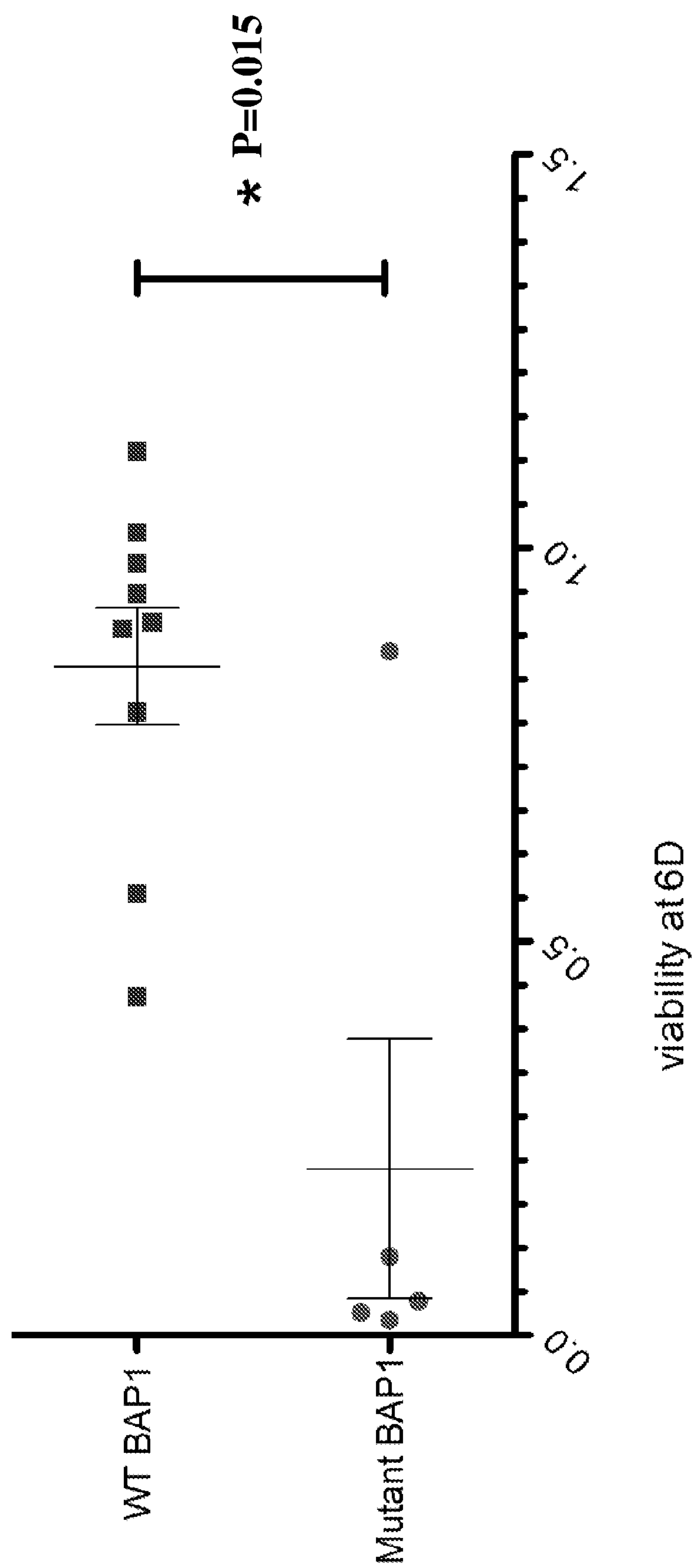

FIG. 2A is a volcano plot showing drug-genome interactions in MPM. The volcano plot displays the mean delta AUC by genotype for 92 library compounds. The Y-axis denotes adjusted p-Value, X-axis denotes effect size. Size of circle indicates number of mutant lines in cohort tested. FIG. 2B is a histogram which shows the results of a 6-day viability assay for multiple mesothelioma cell lines (n=19). rTRAIL (40 ng/ml). Met 5a is a mesothelial normal control line. FIG. 2C is a scatter plot showing AUC following 6 day viability assay in response to 40 ng/ml rTRAIL (normalised to DMSO treated control) in cell lines discretized by BAP1 mutation status. BAP1 mutation status significantly correlates with response to rTRAIL. Two-tailed t-test, p=0.015.

Figure 3A:
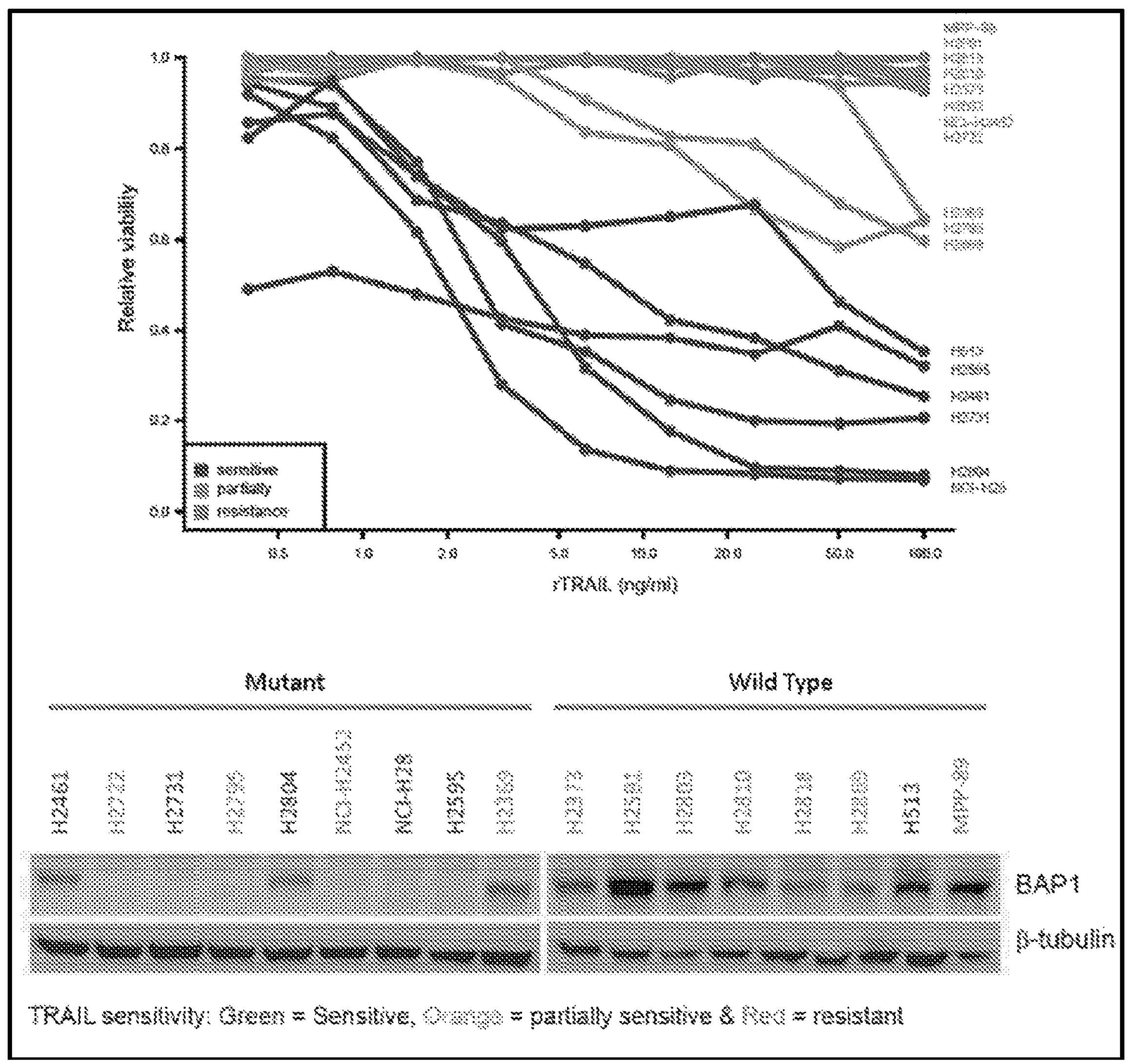
Figure 3B:
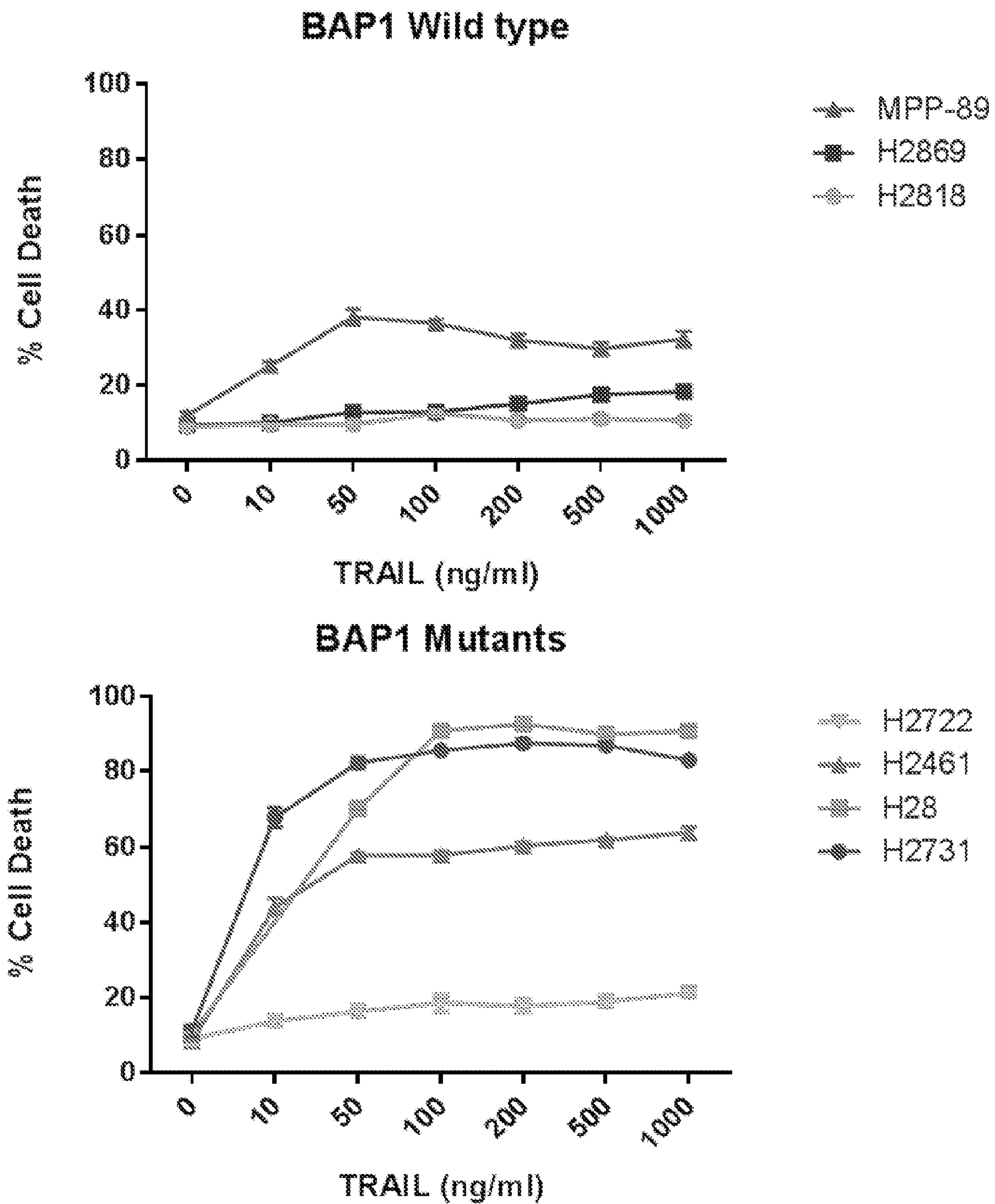

FIG. 3A shows the results of a viability assay in which various MPM cells lines are treated with rTRAIL. MPM cell lines were treated with a dose range from 0.5 ng/ml to 100 ng/ml and cell viability was measured using Syto-60 assay. Based on their cell viability, the cell lines were classified into resistant (red), partially sensitive (orange) and sensitive (green). Cell lines were western blotted to probe the expression of BAP1 protein expression. FIG. 3B shows the results of a viability assay in which various MPM cells lines are treated with rTRAIL. Three BAP1 wild-type cell lines (MPP-89, H2869 & H2818) and four BAP1 mutant cell lines (H2722, H2461, H28 and H2731) were treated with TRAIL (0-1000 ng/ml) for 24 hours and cell death quantified using an Annexin V/DAPI cell death assay.

Figure 4:
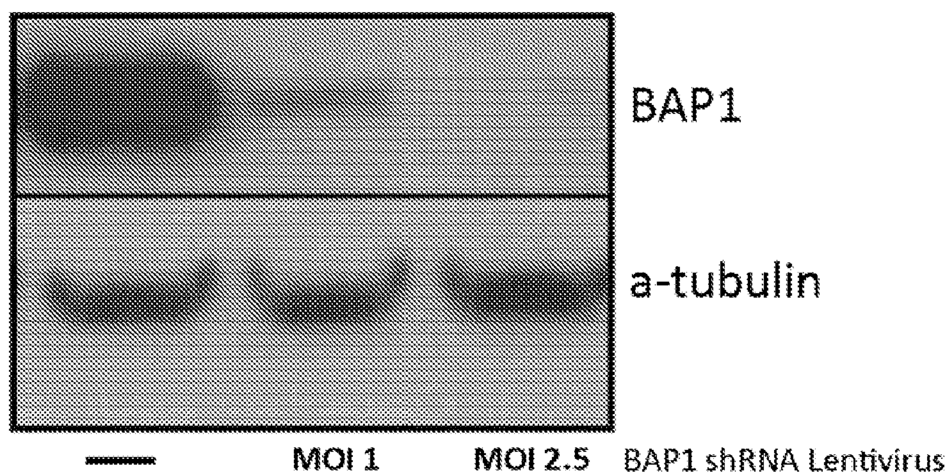
Figure 4:
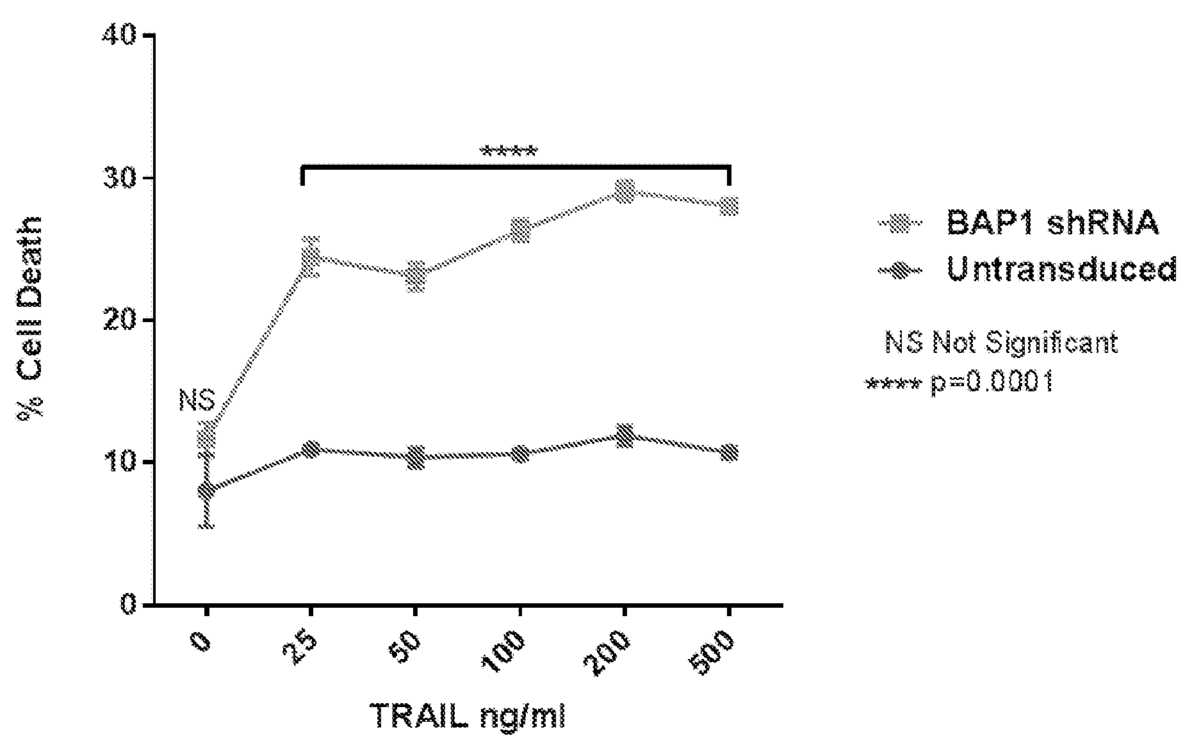

FIG. 4 is a graph (and Western blot), which shows that knocking down BAP1 in a BAP1 wild-type mesothelioma cell line H2818 confers increased cell death response to rTRAIL.

Figure 5A:
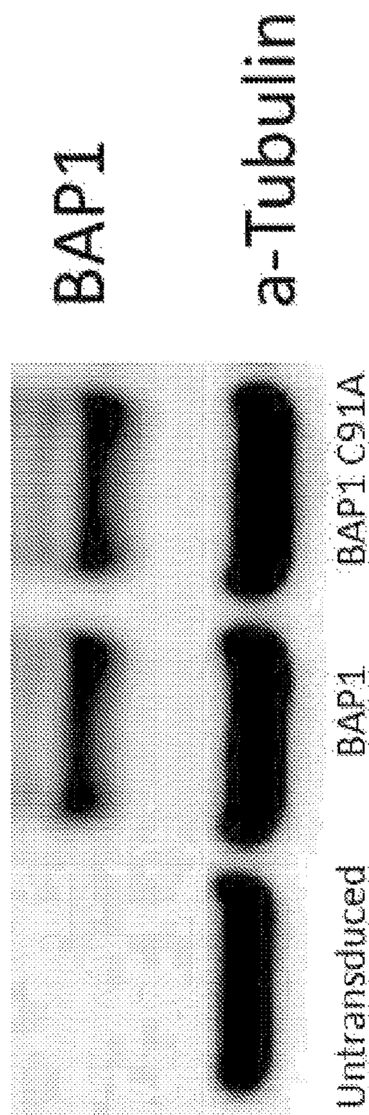
Figure 5B:
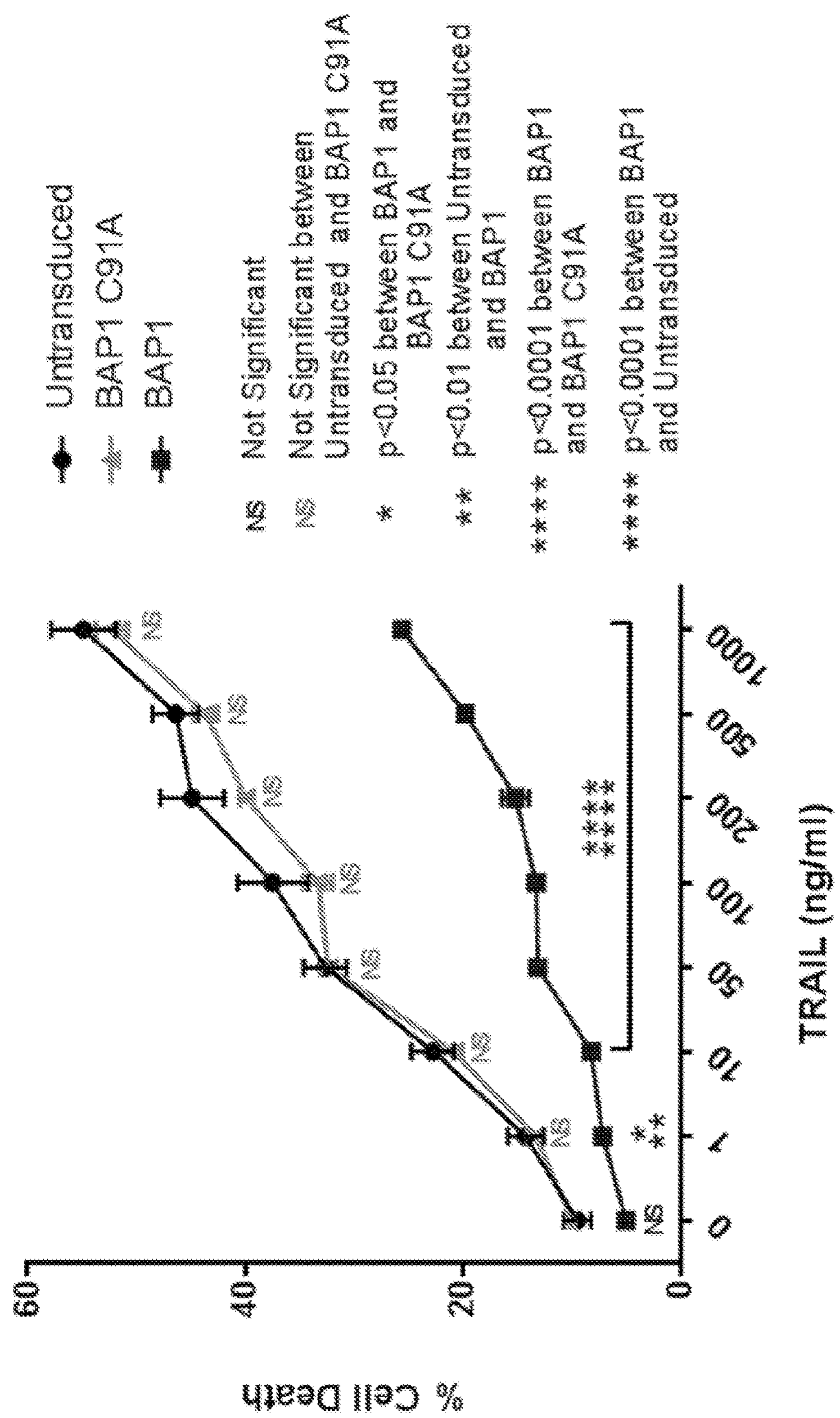
Figure 5C:
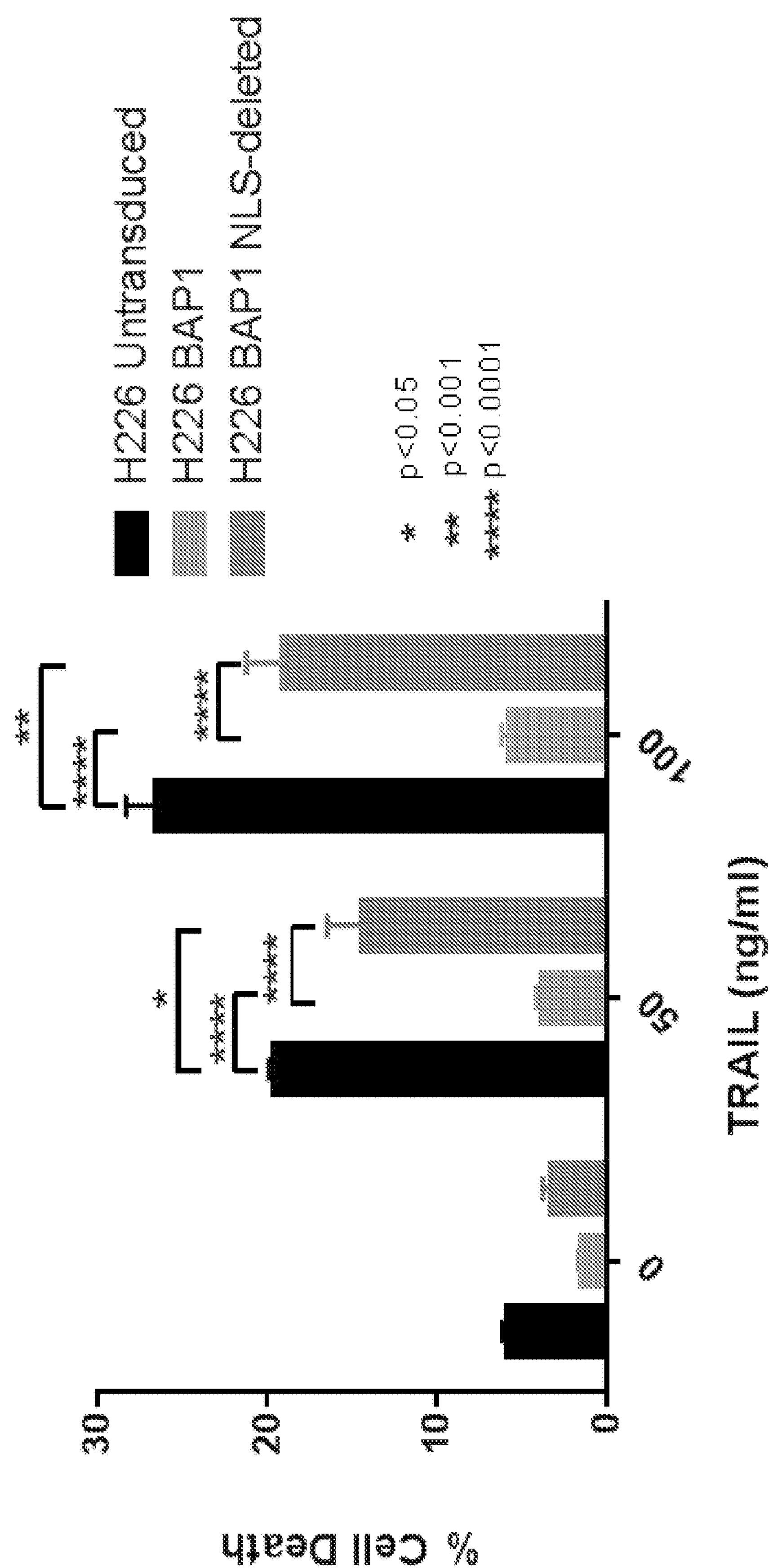

FIG. 5A is an immunoblot for BAP1 protein in BAP1 null mesothelioma lines following transfection with empty vector and BAP1 expression vector. FIG. 5B is a dose-response curve for an Annexin V/DAPI cell death assay performed with rTRAIL on the BAP1 null H226 parental line, a BAP1 wt overexpressing stable line, and BAP1 c91 hydrolase inactive stable cell line. FIG. 5C is a graph showing the effect of rTRAIL on cell viability of an untransduced H226 cell line, a BAP1 (transduced) cell line, and a H226 cell line with the NLS deleted.

Figure 6A:
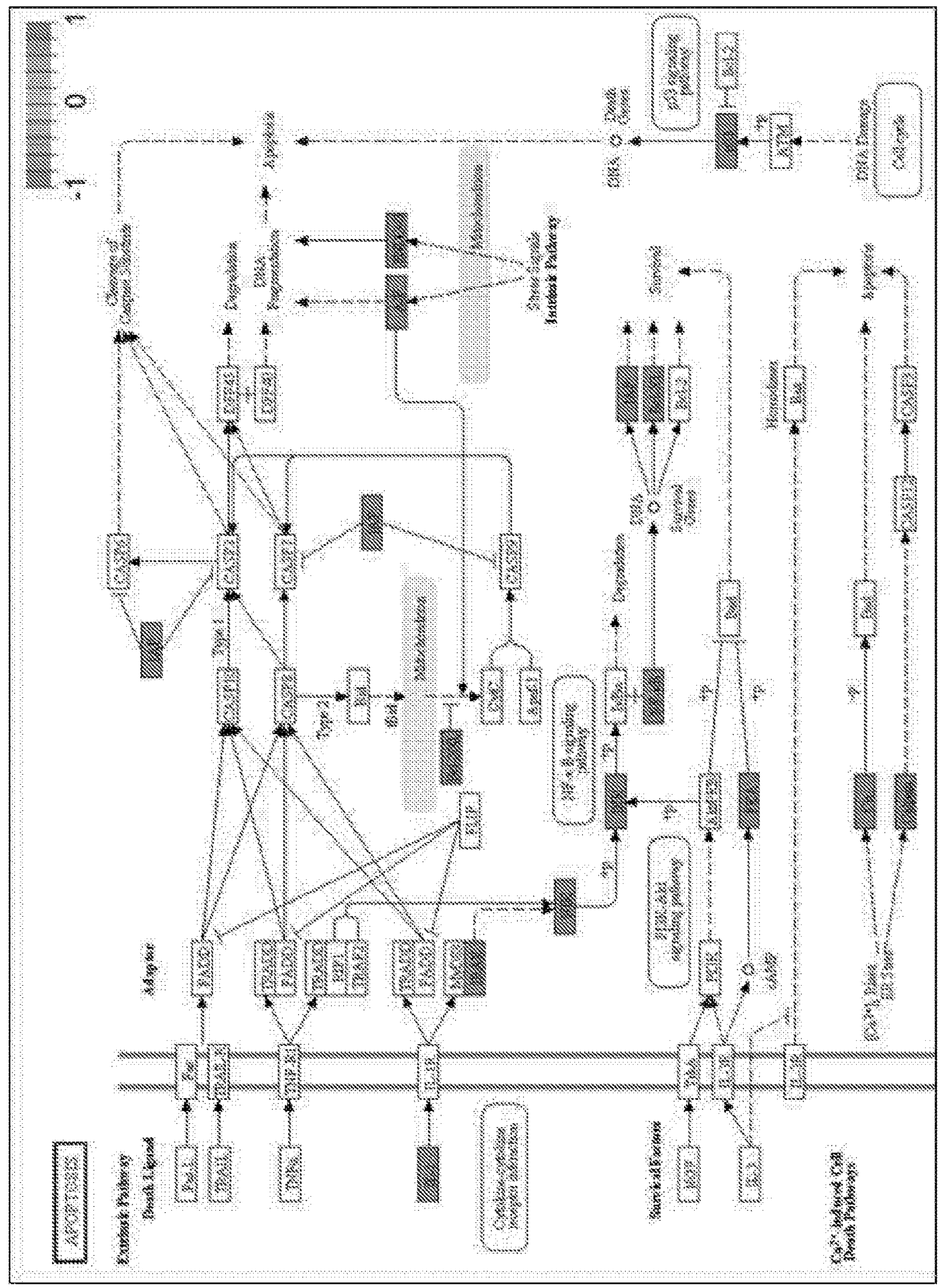
Figure 6B:
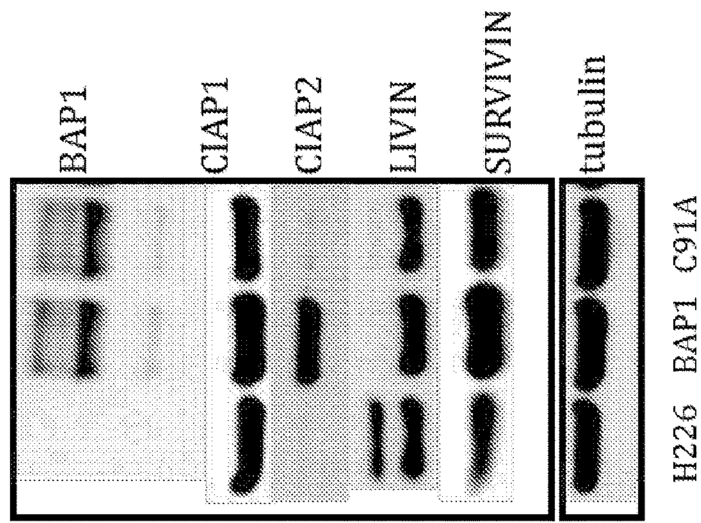
Figure 6B:
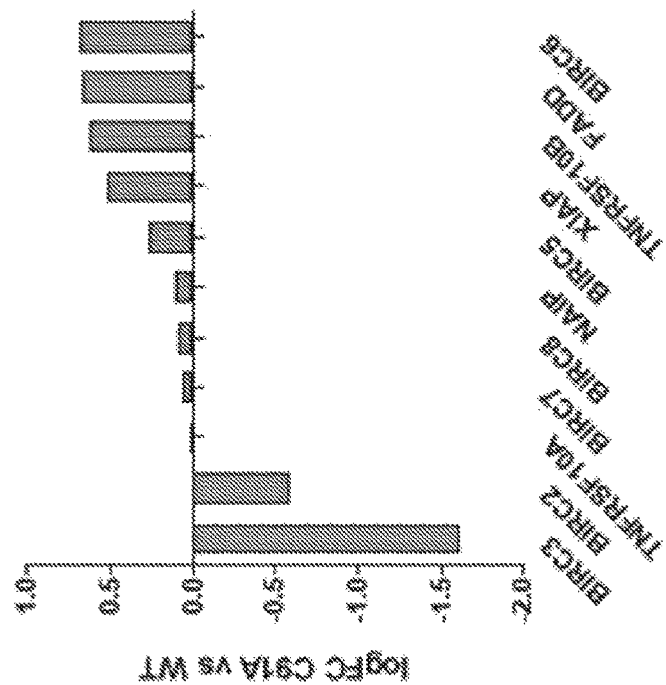

FIG. 6A shows that cell death is significantly dysregulated with the loss of the BAP1 catalytic ubiquitin hydrolation domain. Comparing GEX profile of C91 variant (catalytically inactive) BAP1 transduced H226 with H226 BAP1 wild-type transduced H226 Kegg pathway analysis on significantly dysregulated genes analysis with adj $p<0.05$ and FDR <20%. FIG. 6B is a graph showing RMA normalised gene centered mRNA expression of IAP genes BIRC2 and BIRC3 in c91 mutant BAP1 vs wild-type BAP1 expressing H226 cell line. The Western blot shows dysregulation of IAP family proteins in H226 cell line expressing catalytically inactivated C91 mutant BAP1.

Figure 7A:
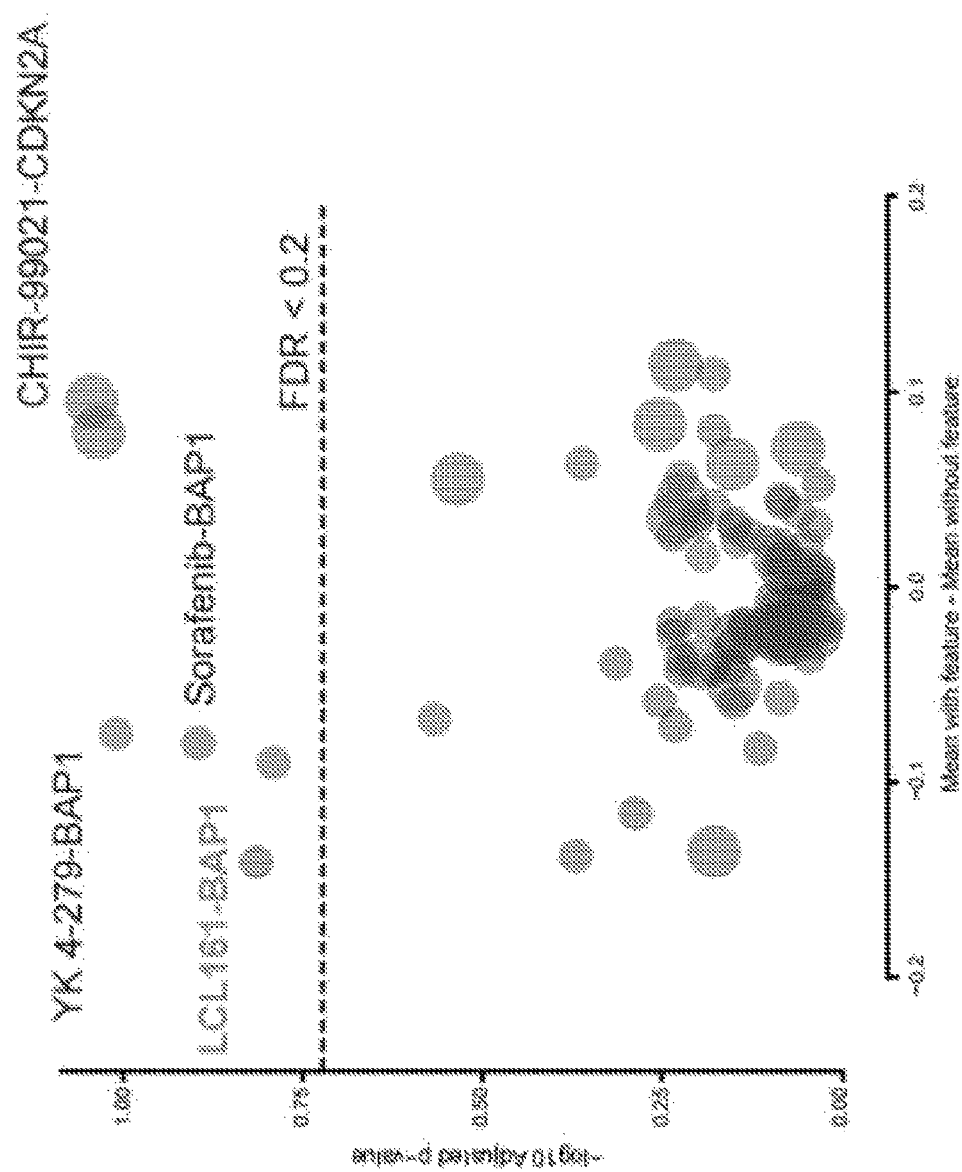
Figure 7B:
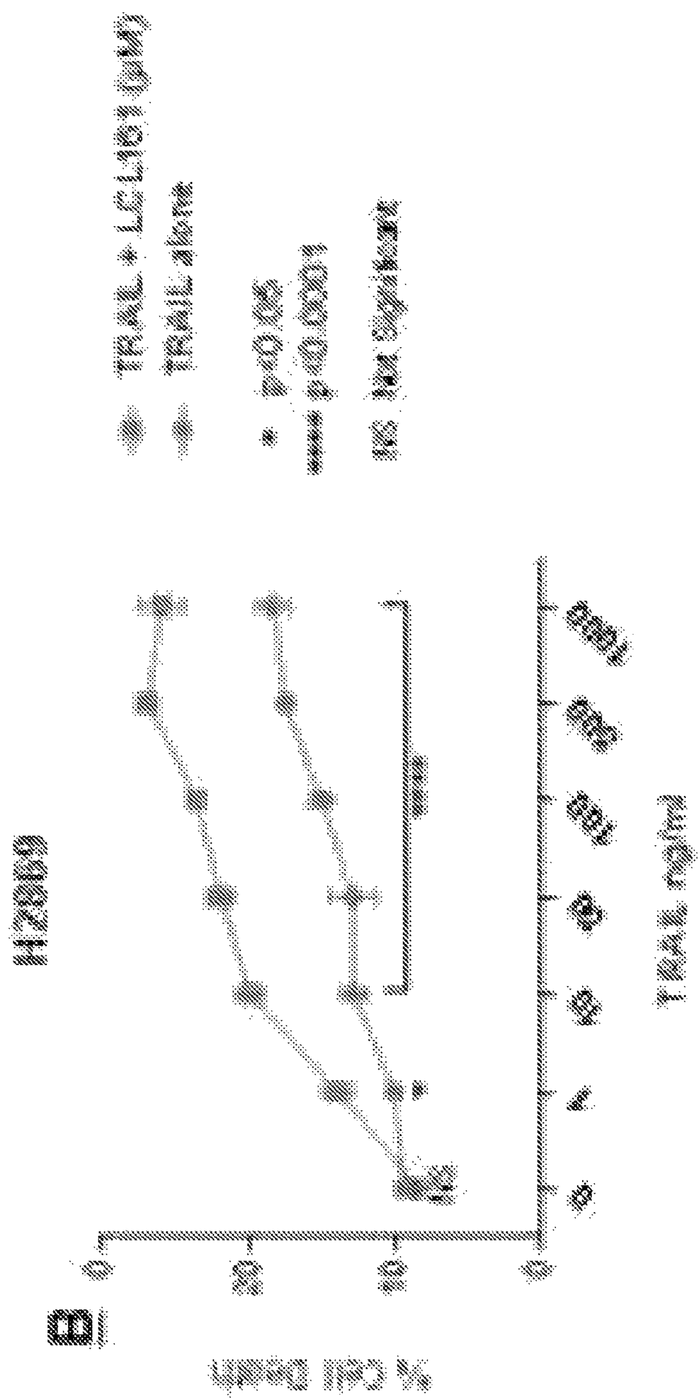
Figure 7C:
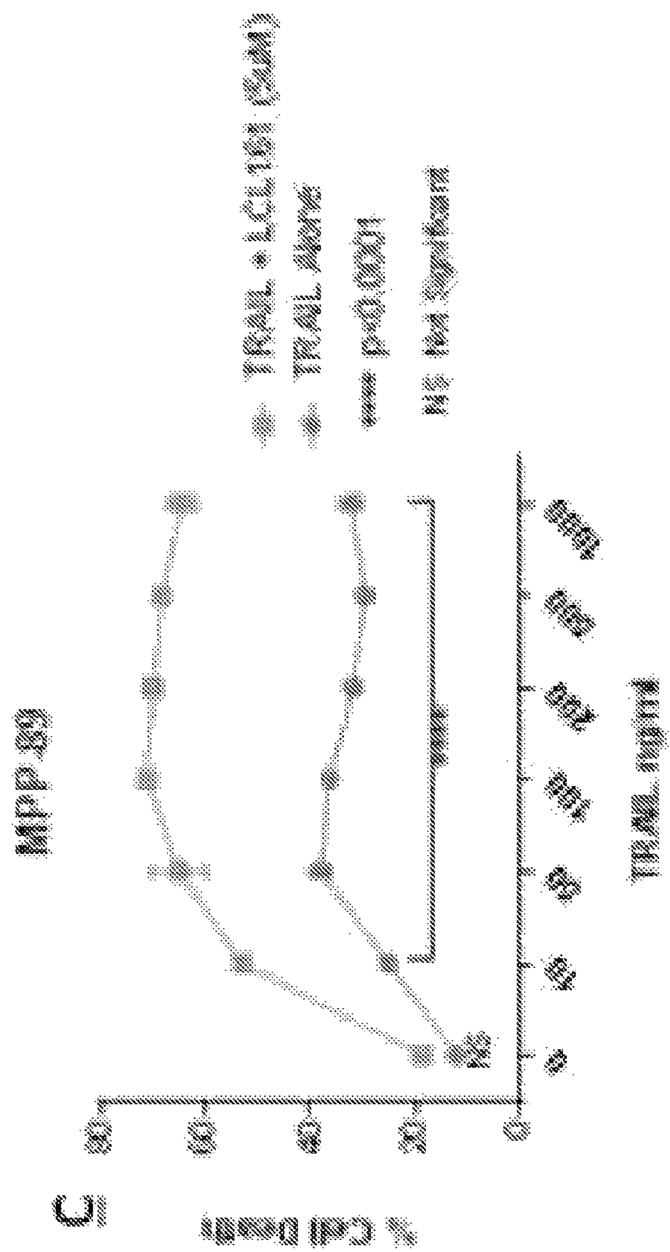
Figure 7D:
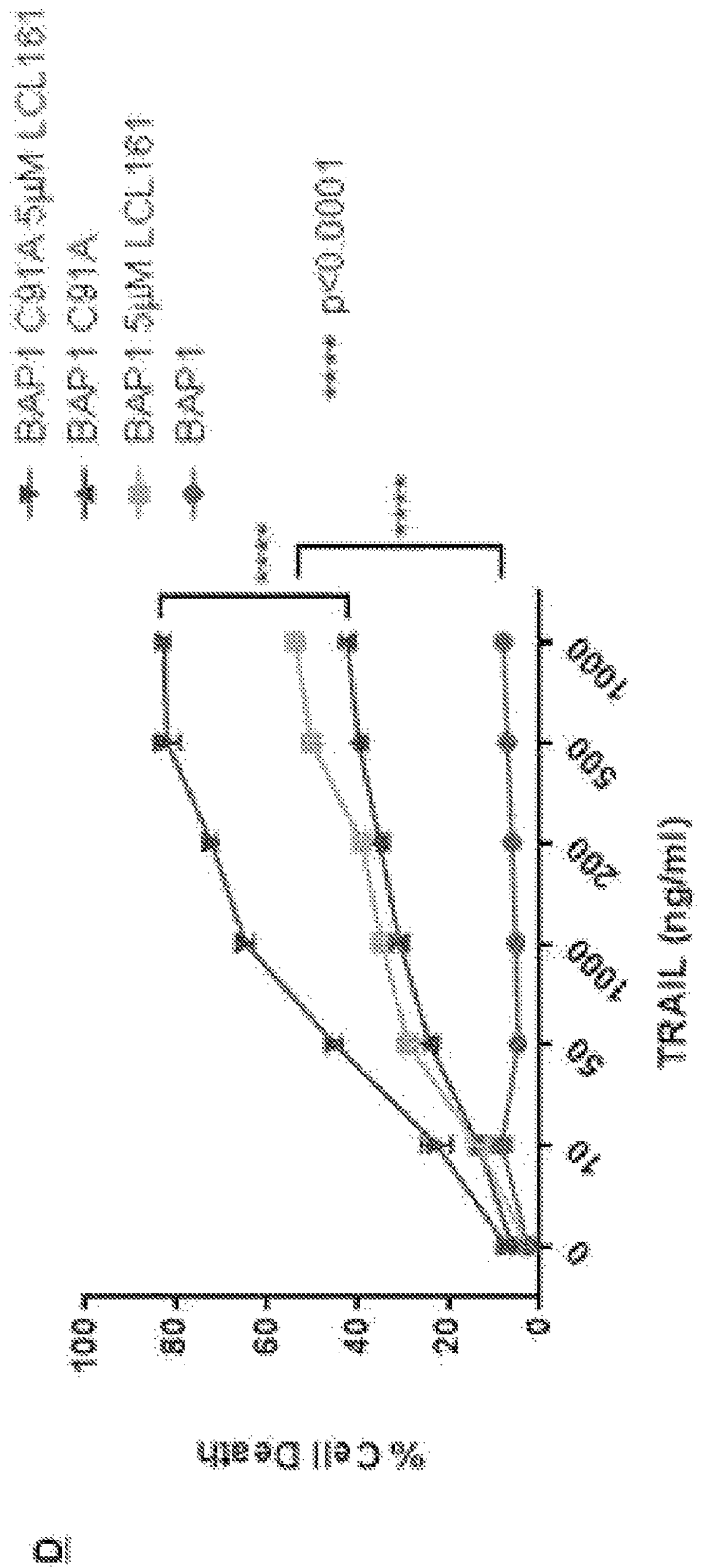

FIG. 7A is a volcano plot showing drug-genome interactions when rTRAIL was used as an anchor drug in combination with the library of 94 single agent compounds. Synergy was described using delta AUC metric. FIGS. 7B & 7C are graphs showing the effect of rTRAIL on cell viability of MPM cells in the presence of LCL161. TRAIL resistant MPM cells were treated with either 0-1000 ng/ml of TRAIL alone or a combination of 5 μM LCL161 and 0-1000 ng/ml of TRAIL for 24 hours and cell death was quantified by Annexin V/DAPI assay. FIG. 7D is a graph showing the effect of rTRAIL on cell viability of cells in the presence of the IAP inhibitor, LCL161. BAP1-transduced or BAP1 C91A-transduced H226 cells were treated either with 0-1000 ng/ml of TRAIL alone or combination of 5 μM LCL161 and 0-1000 ng/ml of TRAIL for 24 hours and cell death was quantified by Annexin V/DAPI assay.

Figure 8A:
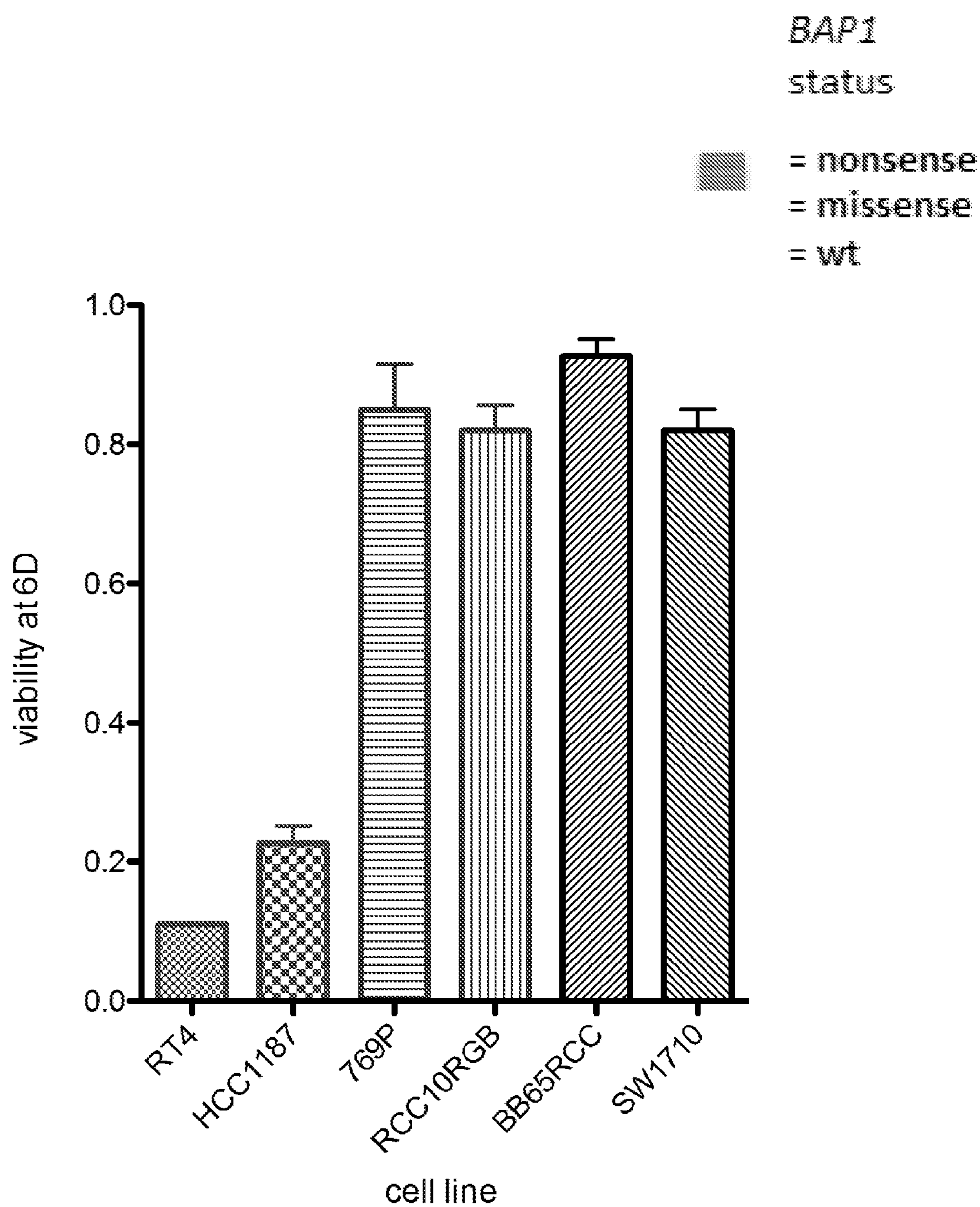
Figure 8B:
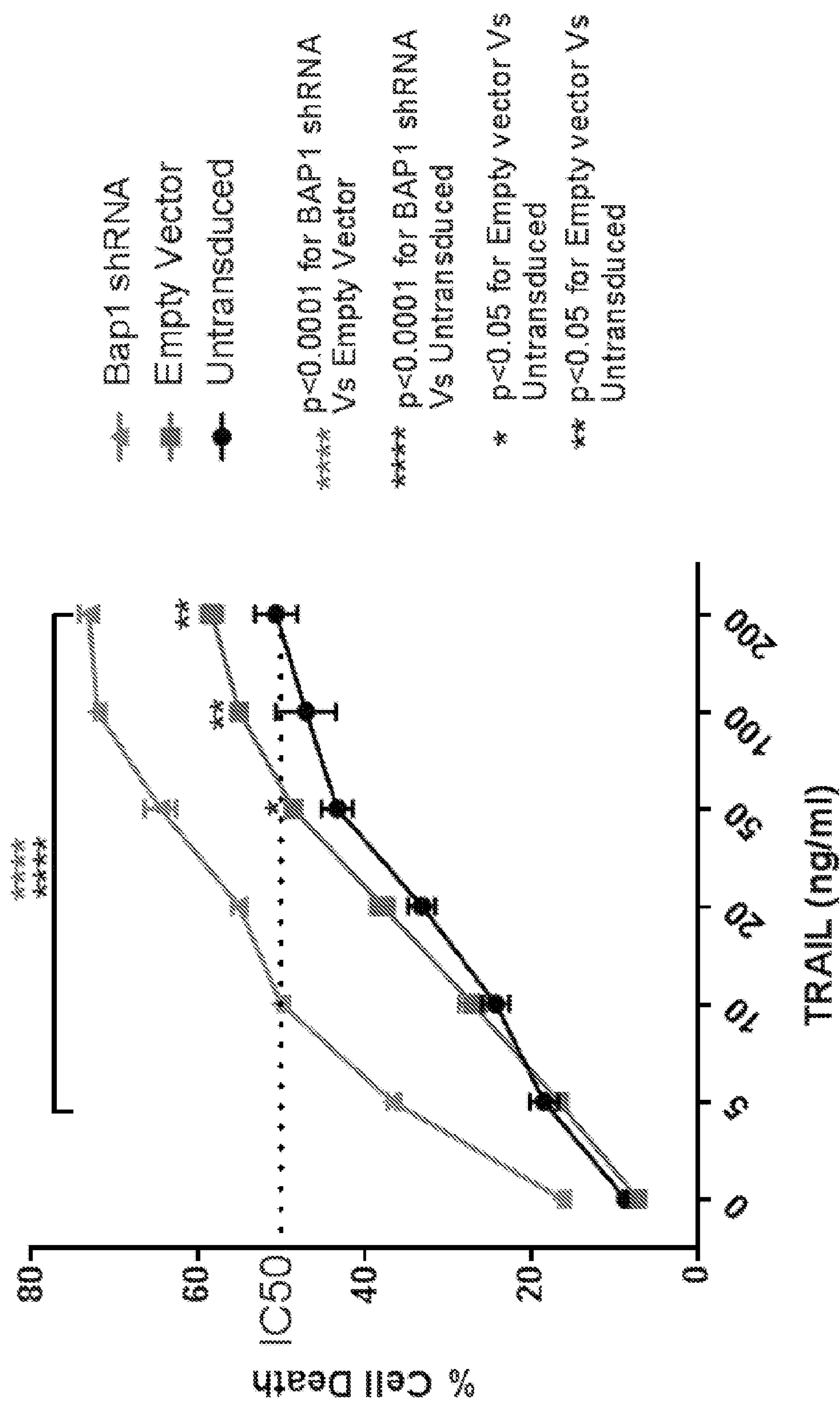

FIG. 8A is a graph showing the effect of rTRAIL on the viability of various cancer cell lines. Bladder (RT4) and Breast (HCC1187) cancer cell lines with nonsense mutations in BAP1 show sensitivity to rTRAIL while renal cell cancer cell lines (769P & RCC10RGB) with missense mutation and wild-type renal (BB65RCC) and bladder cancer (SW1710) cell lines are resistant to TRAIL. FIG. 8B shows that knockdown of BAP1 in Breast cancer cell line MDA MB-231 increases sensitivity to rTRAIL.

Figure 9A:
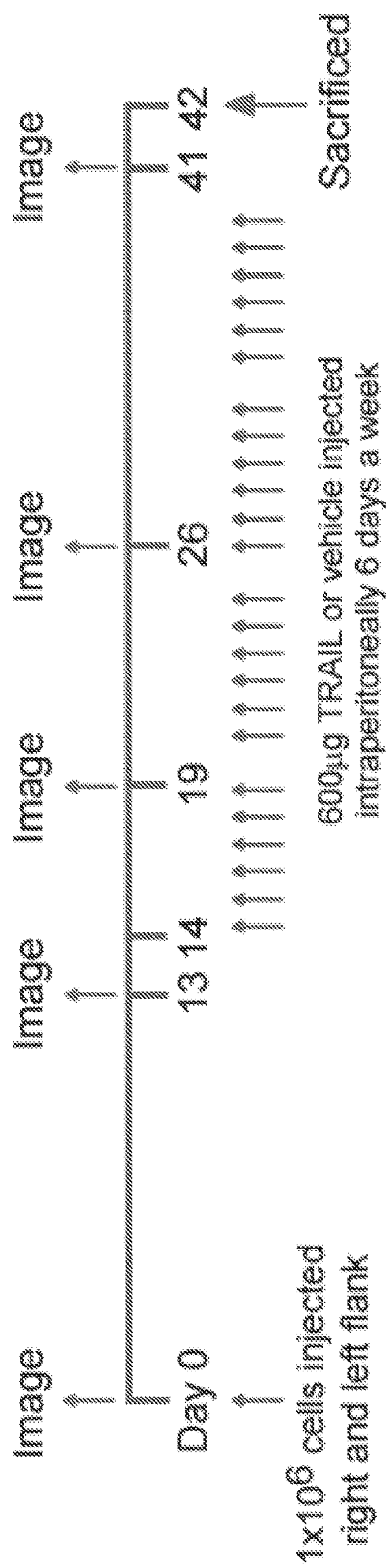
Figure 9B:
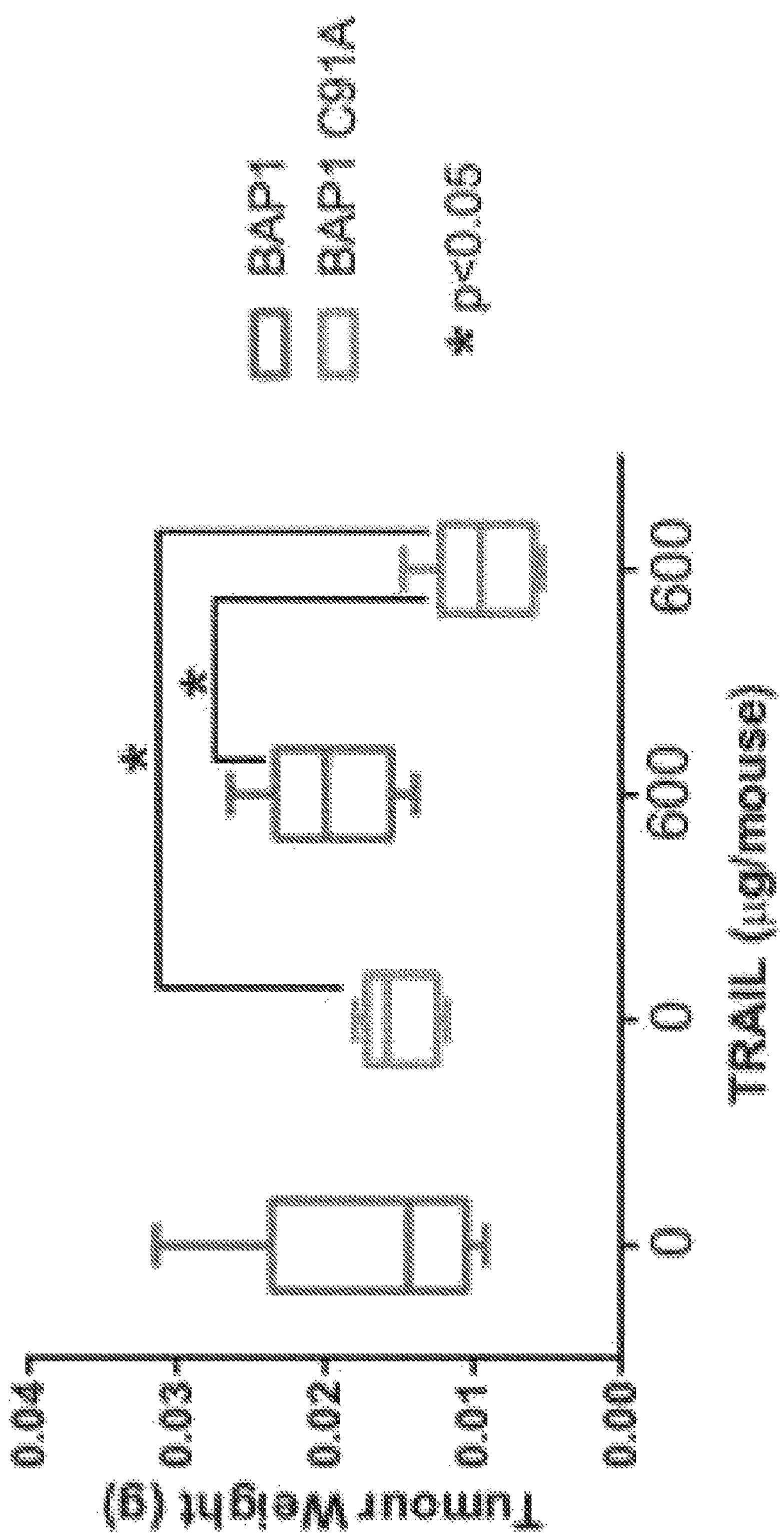
Figure 9C:
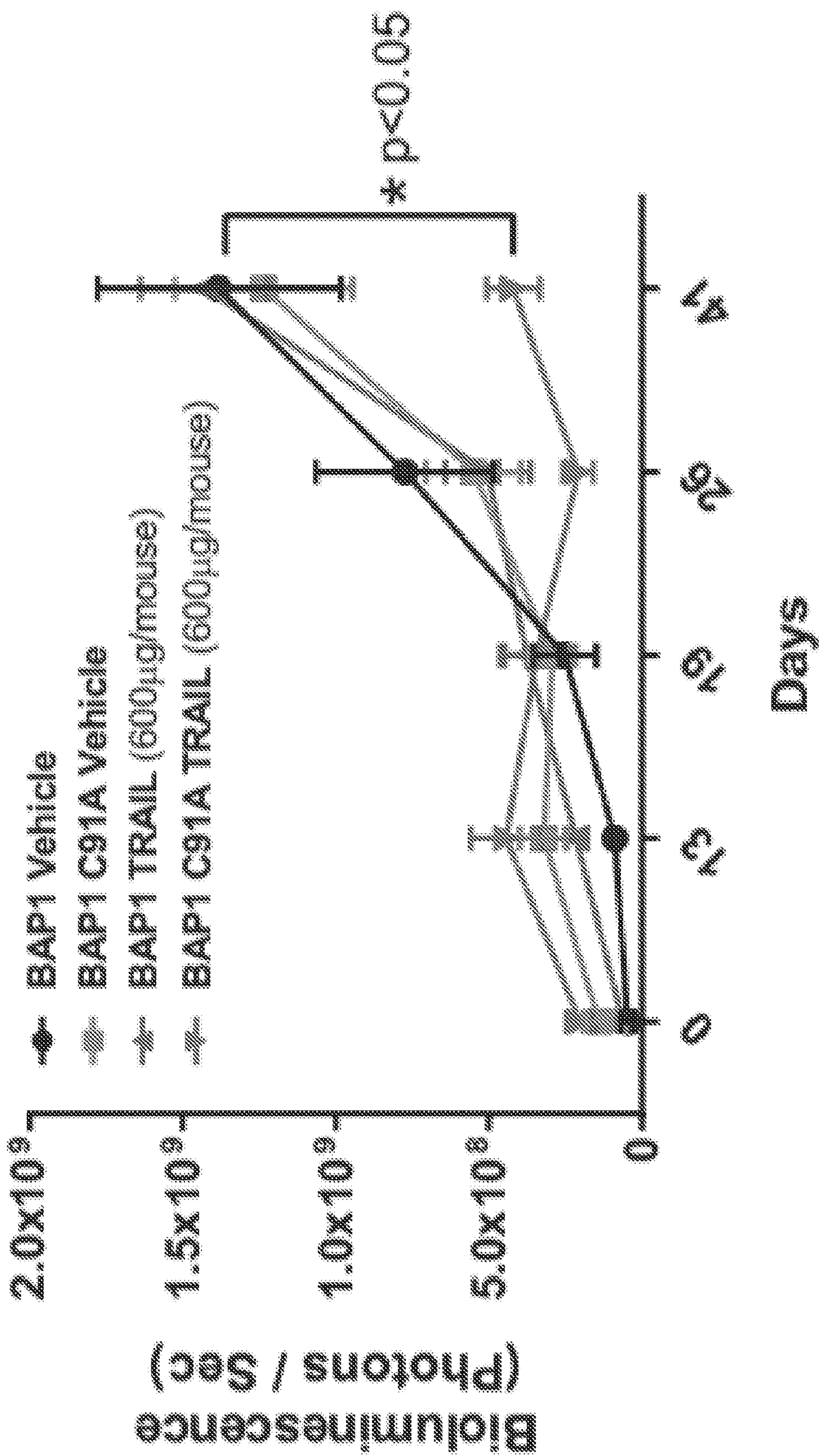

FIG. 9A is a protocol of an in vivo experiment. FIG. 9B is a box plot showing the weight of tumours extracted from mice injected with mutant or wild-type BAP1-expressing cells after treatment with rTRAIL. Tumour weights of mutated BAP1 xenografts are significantly smaller than wild-type BAP1 xenografts after TRAIL treatment. FIG. 9C is a graph showing that TRAIL treatment reduces the tumour burden (measured by bioluminescence) of mutated BAP1 xenografts when compared to TRAIL treated wild-type BAP1 xenografts or untreated BAP1 mutated and BAP1 wild-type xenografts.

Figure 10:
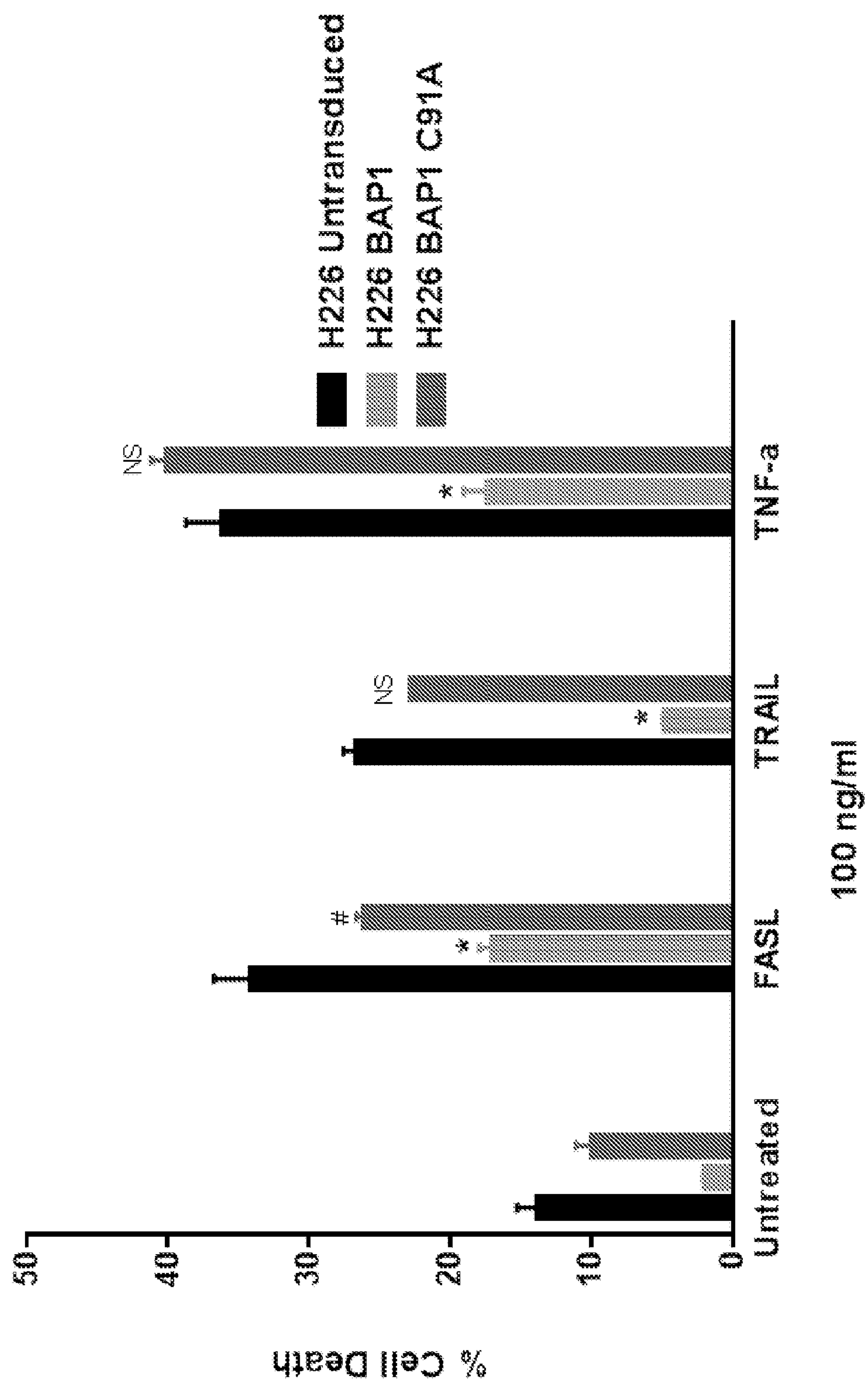

FIG. 10 is a graph, which shows that BAP1 the that catalytic domain of BAP1 also regulates the sensitivity of H226 cells to the cell death-inducing ligands, TRAIL, FASL and TNFα. Untransduced BAP1-negative H226 cells, BAP1-expressing and catalytically dead BAP1-expressing H226 cells were treated with 100 ng/ml of FASL, TRAIL and TNF-alpha for 24 hours and cell death was quantified by Annexin V/DAPI assay. *$p<0.05$ indicating significant difference between untransduced H226 cells H226 BAP1 expressing cells. NS no significant difference between untransduced H226 cells and BAP1 C91A transduced cells. #$p<0.05$ indicating significant difference between untransduced H226 cells and BAP1 C91A transduced cells.

Figure 11:
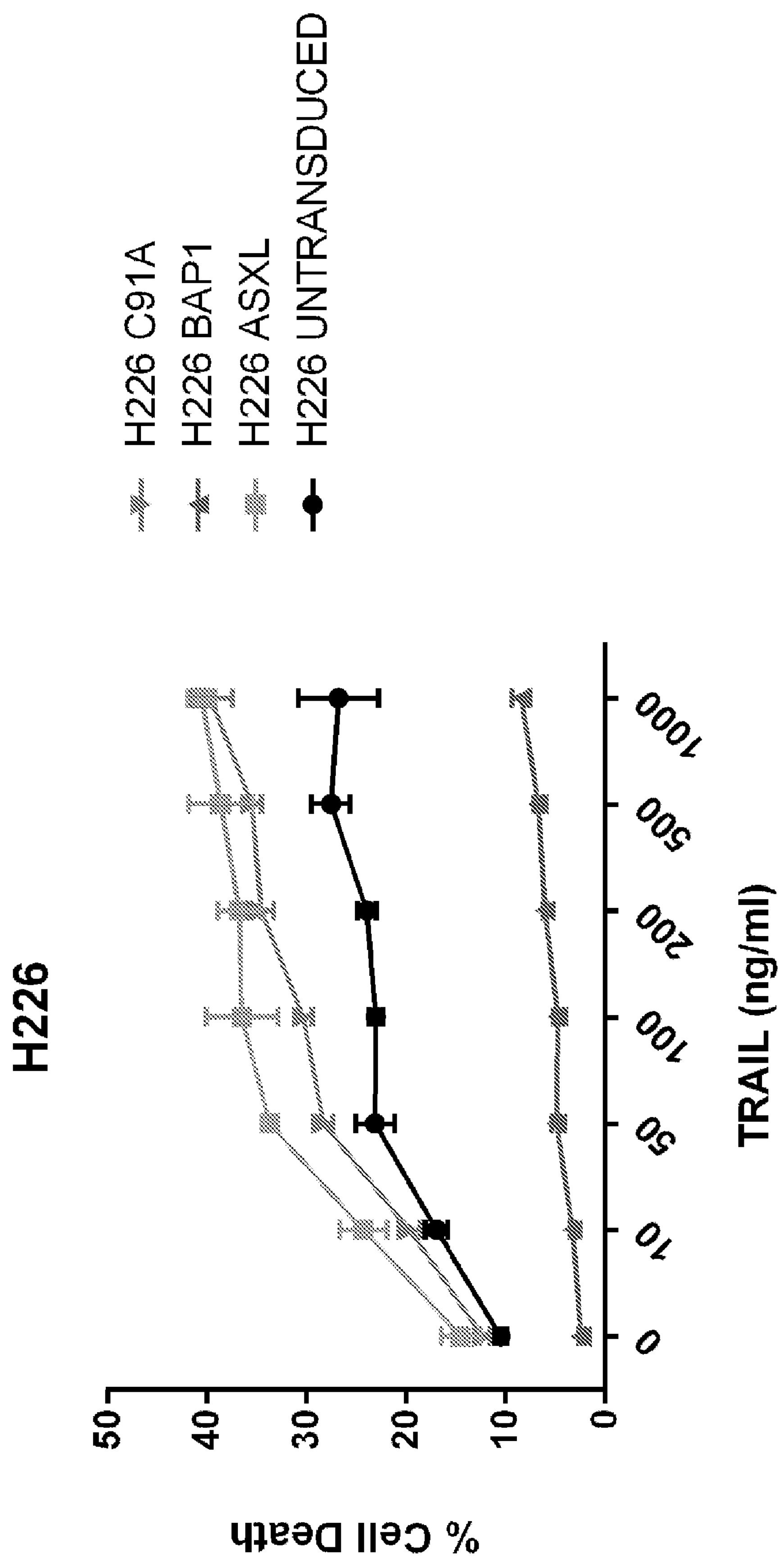

FIG. 11 is a graph, which shows that BAP1 that catalytic domain of BAP1 also regulates the sensitivity of H226 cells to the cell death inducing ligands, TRAIL, FASL and TNFα. Untransduced BAP1-negative H226 cells, BAP1-expressing, ASXL binding site deleted BAP1-expressing H226 cells and catalytically dead BAP1-expressing H226 cells were treated with 100 ng/ml of FASL, TRAIL and TNF-alpha for 24 hours and cell death was quantified by Annexin V/DAPI assay.

EXAMPLES

The inventors have discovered that mutation of the BAP1 tumour suppressor gene confers sensitivity to therapeutic modulation of the apoptotic pathway in human cancers. They have explored and validated this association in malignant pleural mesothelioma, bladder carcinoma and breast carcinoma and have evidence that it can be extended to between 1-36% human cancers, including renal cell carcinoma, and cervical cancer and uveal melanoma. Although the data described herein focuses on rTRAIL, a recombinant protein that activates the TRAIL pathway by binding to TRAIL receptor 1 (TRAIL-R1, also known as death receptor 4; DR 4) and TRAIL-R2 (also known as DR 5), BAP1 is also found to modulate other pro-apoptotic pathways, such as the FAS ligand pathway or the TNF pathway or intrinsic apoptotic pathway (see Example 6).

Materials and Methods

Whole Exome Sequencing

DNA was extracted using the column extraction technique as per manufacturer's instructions (QIAGEN). Genomic libraries were prepared using the Illumina paired end sample prep kit following the manufacturer's instructions. Exome enrichment was performed using the Agilent SureSelect Human All Exon 50 Mb kit following the manufacturer's recommended protocol. Each exome was sequenced using the 75-bp paired end protocol on an Illumina HiSeq 2000 DNA Analyser to produce approximately 5-10 Gb of sequence per exome. Sequencing reads were aligned to the human genome (NCBI build GrCh 37) using the Burrows-Wheeler aligner (BWA) algorithm with default settings (17). Unmapped reads and PCR duplicates were excluded from the analysis. Average coverage of the cell line exomes at lox or higher was 80%.

Copy Number Annotation

DNA was extracted as above. DNA was outsourced to AROS for SNP 6.0 array. Copy number annotation was derived from the PICNIC algorithm [18].

Variant Detection

The CaVEMan algorithm was used to call single nucleotide substitutions [19]. The algorithm uses a naïve Bayesian classifier to estimate the posterior probability of each possible genotype (wild-type, germline or somatic mutation) at each base. To call insertions and deletions, split read mapping was implemented as a modification of the Pindel Algorithm [19]. Pindel searches for one read anchored on the genome with the other read mapped in two portions, spanning a putative insertion/deletion. For both algorithms, an identical putative normal from the CGP panel of tumours was nominated that has been used in all cell lines studied without available matched normal tissue. Significant post processing filtering against various panels of normal was subsequently undertaken to eliminate as many germline single nucleotide polymorphisms as possible. These include the 1000 genomes database, DB SNP, and an internal panel of CGP normal. Following these steps missense variants were annotated using the FATHM algorithm (Cancer Genome Project) as to potential functional consequence of the variant.

Combination (Genome-Drug) Therapeutic Screen Approaches

Manual "single dose" combination screening was undertaken using 96 well formats. Cells were plated on day 1 in previously optimized seeding densities in 180 μl if media. On day 2 20 μl of a 10× concentration of media from a stock of drugs was added. Cells were then allowed to grow for 72 hrs or 6 days and fixed at the end of the assay. Drug wells were compared to DMSO treated control wells.

Single agent high throughput 5 point viability screening was undertaken in 384 well formats [18] using robotic liquid handling with fixing with 4% paraformaldehyde and staining for viability with Syto60 nucleic acid dye (Invitrogen) (see below). Single agent dose response curves were derived for each library of 85-95 drugs according to the experiment used, and log IC50 or area under the curve (AUC) metrics were derived for each library compound in each cell line according to a previously derived formula [18]. Using this data various 2-drug synergy was measured with a Delta AUC metric.

A binary event matrix was compiled for the cell lines in the mesothelioma screen by aggregating copy number and exome data and this was used as input classifiers for genomic correlation. Data from this therapeutic screen was then analysed using a Multivariate Analysis of Variance (MANOVA) [18] to annotate the sensitizing effect of genotype on dose response. The results are presented as a volcano plot demonstrating significance of the interaction (above a Benjamin Hochberg false discovery threshold) and magnitude of effect size.

Analyses of TCGA Data

Frequency of BAP1 truncating mutations in various cancer types is based upon data generated by The Cancer Genome Atlas (TCGA) Research Network.

Cell Culture 293T cells were cultured in Dulbecco's modified Eagle's medium (DMEM) supplemented with 10% fetal bovine serum (FBS), nonessential amino acids, 50 U/mL penicillin, 50 μg/mL streptomycin, and 1% sodium pyruvate. Human mesothelioma cell lines were cultured in RPMI-1640 medium supplemented with 10% FBS, 1% penicillin-streptomycin and 1% sodium pyruvate (H2369, H2373, H2461, H2591, H2595, H2722, H2731, H2795, H2803, H2804, H2869, H290, H513, IST-MES1, MPP-89, MSTO-211H, NCI-H2052, NCI-H2452, NCI-H226, NCI-H28) or Dulbecco's Modified Eagle Medium/Nutrient Mixture F-12 (DMEM/F-12) supplemented with 10% FBS, nonessential amino acids, 50 U/mL penicillin, 50 μg/mL streptomycin, and 1% sodium pyruvate (H2818, H2810). Cells were maintained at 37° C. at 5% $CO_2$.

Western Blotting

Cell monolayers were washed in phosphate buffered saline (PBS) and lysed in radioimmunoprecipitation assay (RIPA) buffer (Sigma-Aldrich) and protease inhibitors (Complete-mini; Roche) on ice. Lysates were centrifuged at 14000 rpm for ten minutes and the supernatant aspirated. Protein concentration was calculated from a standard curve of bovine serum albumin using the BCA assay (Calbiotech) according to the manufacturer's instructions. Lysates were prepared to the appropriate concentration and 4× Laemelli buffer and 10× reducing agent added prior to the sample being heated at 70° C. for ten minutes. Lysates were subjected to SDS-PAGE on pre-cast 4-12% Bis-Tris gels (Invitrogen) at 200V for 1 hr. Protein was transferred onto a nitrocellulose membrane using an iBlot gel transfer device (Invitrogen) as per manufacturer's instructions. Membranes were blocked in 5% milk in tris-buffered saline with Tween 20 (TBS-T) before the addition of primary antibody (at 1:1000 in TBS-T unless otherwise stated) overnight at 4° C. The following day the membrane was washed three times in TBS-T and secondary antibody added (at 1:2500 in TBS-T) Antibodies used include BAP1 (C-4; Santa Cruz sc-28383), alpha tubulin (Cell Signalling #2125), c-IAP1 (Cell signaling #7065), cIAP2 (Cell signaling, #3130), Livin (Cell Signalling #5471), Survivin (Cell signaling, #2803), Alexa Fluor® 488 (Invitrogen A-21202). Immunoblots were imaged using an ImageQuant™ LAS 4000 biomolecular imager.

Cell Viability Assays

Adherent cell lines were seeded 24 hours before drugging. Cells were trypsinised and counted before seeding at the optimal density for the size of well (96 or 384) and duration of assay. 72 hr after drug treatment cells were fixed with 4% paraformaldehyde for 30 minutes. Following two washes of $dH_2O$ 100 μl Syto60 nucleic acid stain (Invitrogen) was added at a final concentration of 1 μM and plates fixed for 1 hr at room temperature. Quantification of fluorescent signal was achieved using excitation/emission wavelength of 630/695 nM.

Cell Death Assays

Adherent mesothelioma cell lines were plated in a 96 well plate at approximately 10000 cells per well. Cells were plated and given 1 day to adhere at which time drug was added. After 48 hrs media, including floating cells, was collected from each well. The remaining adherent cells were washed with PBS and mobilised with 0.05% trypsin in EDTA. All cells were collected into tubes containing the previously removed media and pelleted by centrifugation (300 g, 5 minutes). Cells were then re-suspended in 1× Annexin V binding buffer with 10 μl/1 ml concentration of Annexin V-647 antibody (Invitrogen) and incubated for 15 minutes at room temperature. DAPI (41 g/ml) was then added to each sample before flow cytometry analysis as below. Annexin V−/DAPI− cells were judged to be viable, AnnexinV+/DAPI− cells were considered to be undergoing apoptosis (early apoptotic phase), and Annexin V+/DAPI+ cells were considered late apoptotic or necrotic, and recorded as dead.

Flow Cytometry Analyses

Cells were washed with phosphate buffered saline and fixed by incubation in 4% paraformaldehyde for 20 minutes at room temperature. For intracellular BAP1 staining, fixed cells were permeabilised in 0.1% triton X-100 in PBS for 20 minutes on ice, washed twice with PBS, incubated with primary antibody (C-4; Santa Cruz sc-28383, 1:100) for 20 minutes on ice, washed twice again and incubated with a fluorescent secondary antibody (Alexa Fluor® 488, 1:200

(Invitrogen A-21202)). Cells were washed twice with PBS and suspended in PBS for flow cytometry analysis. Cells analysed as part of the cell death assays were prepared as above.

Flow cytometry analysis was conducted on an LSR-Fortessa cell analyser (BD Biosciences) and data analysed with FlowJo software.

mRNA Microarray

The mRNA from catalytically inactive BAP1 expressing H226 cells (H226 C91A) and WT BAP1 expressing H226 cells (H226 BAP1) was extracted and run on an Illumina HT12 array.

Pathway Analysis

The significantly differentially expressed genes identified from the mRNA microarray were analysed using KEGG pathway analysis.

Plasmids

The cDNA full-length clone of human BAP1 was obtained in a pCMV6-AC backbone (Origene, SC117256), which was cloned into a PCCL.CMV lentiviral backbone for all further experiments. BAP1 mutant constructs were generated using site directed mutagenesis kits (NEB) and confirmed by full length DNA sequencing. Short hairpin RNAs were obtained through UCL RNAi library in a GIPZ shRNAmir lentiviral vector (Dharmacon V2LHS41473). The sequence (SEQ ID NO. 44) for the short hairpin is as follows:

```
                                    [SEQ ID NO. 44]
TAAAGGTGCAGATGAACTC
```

Lentivirus Production and Concentration

Lentiviruses were generated by transfection of 293T cells with the lentivirus vector plasmids together with the packaging plasmid pCMVdR8.2 and envelope plasmid pMDG.2 using jetPEI (Polyplus Transfection) as the transfection reagent. The 293T cells were incubated at 37° C. and the medium containing the lentiviruses harvested at 24 and 48 hrs. The lentivirus was concentrated by ultracentrifugation at 18000 rpm for 2 hours at 4° C. (SW28 rotor, Optima LE80K Ultracentrifuge, Beckman) and stored at −80° C. before use.

Lentivirus titration was performed by transducing 293T cells with serial dilutions of virus in the presence of 4 μg/ml polybrene. After 4 days cells were analyzed for the percentage of BAP1 positive cells using flow cytometry. Viral was calculated as follows:

Titre (transduction units (TU)/ml)=Proportion of BAP1 positive cells×number of seeded cells/volume of virus (ml)

MPM cells were then transduced with a range of multiplicity of infections (MOIs) in the presence of 4 μg/ml polybrene and transduction efficacy assessed by flow cytometry analysis. The optimal population (lowest MOI at which >90% transduction achieved) was selected for further experiments.

shRNA Experiments

Lentivirus encoding shRNA targeting BAP1 was generated as per the lentivirus production protocol above. MPM cells (H2818) were transduced and treated with puromycin 200 μg/mL until a pure population was achieved. Immunoblotting was performed to assess efficacy of the shRNA knockdown.

Animals

All animal studies were approved by the University College London Biological Services Ethical Review Committee and licensed under the UK Home Office regulations and the Evidence for the Operation of Animals (Scientific Procedures) Act 1986 (Home Office, London, UK). Mice were purchased from Charles River, kept in individually ventilated cages under specific pathogen-free conditions and had access to sterile-irradiated food and autoclaved water ad libitum.

Xenograft Mouse Models

Groups of 8 week old NOD.CB17-Prkdcscid/NcrCrl (NOD SCID) mice (Charles River) were injected on each flank with 1 million cells of luciferase transduced mesothelioma cell lines (H226 BAP and H226 C91A) in a 1:1 mixture of matrigel and media. When tumours were established, as assessed by bioluminescent imaging (IVIS), at 14 days following injection of tumour cells, treatment was began with either vehicle or isoleucine zipper TRAIL (izTRAIL) [20]. Either vehicle or izTRAIL were given intraperitoneally once daily at a dose of 600 mcg for the duration of the experiment. Tumour size was assessed at days 0, 13, 19, 26 and 41 using bioluminescent imaging (IVIS). Mice were culled at 42 days and tumours removed and weighed. Six mice per group were treated. Researchers were not blinded in these experiments.

Statistical Analyses

Statistical analysis was performed using GraphPad Prism V. 4 (GraphPad Software). In vivo experiments with multiple groups were analysed using repeated measures ANOVA, and single-group data were assessed using Student t test. All in vitro experiments were performed in triplicate unless specified otherwise.

Example 1—TRAIL Targets BAP1 Mutant Mesothelioma Cells

The inventors carried out a combinatorial chemical screen in 15 mesothelioma cell lines (together with the Met 5a mesothelial normal control line) using 94 small molecule inhibitors and chemotherapy agents (see Table 1) either alone or in combination with the ligand tumour necrosis factor (TNF)-related cell death inducing ligand (TRAIL). To detect examples of extreme drug sensitivity, the inventors analysed for statistical associations between response and the mutational status of these cell lines based on a set of 8 genes recently identified as being candidate cancer genes in mesothelioma (see FIG. 1A). Of note BAP1 mutations are well recognised across cancer types (see FIGS. 1B and C). The largest effect of a mutation on drug response was that of mesothelioma cells harbouring a mutation in the deubiquitinase BAP1 and treated with TRAIL (see FIG. 2A). There was no significant effect on cell viability observed in the control normal mesothelial cell line MET-5A included in the screen (see FIG. 2B). BAP1 mutant cells were significantly more sensitive to TRAIL than their wild-type counterparts (see FIGS. 2B & 2C). Furthermore, the BAP1 mutations detected in these cell lines would be predicted to be truncating (see Table 2). The inventors confirmed by immunoblot that BAP1 mutations were usually associated with loss of protein expression and the mutant cell lines are generally sensitive to TRAIL (see FIG. 3A).

TABLE 1

Compounds used in combinatorial chemical screen with 15 mesothelioma cell lines together with the Met5a mesothelial normal control line.

| compound | target | Targeted process/pathway | min conc (uM) | max conc (uM) |
|---|---|---|---|---|
| AICAR | AMPK agonist | metabolism | 7.81 | 2000 |
| Camptothecin | DNA topoisomerase I | DNA replication | 0.0004 | 0.1 |
| Vinblastine | Microtubules | cytoskeleton | 0.0004 | 0.1 |
| Cisplatin | DNA crosslinking | DNA replication | 0.0234 | 6 |
| Docetaxel | Microtubules | cytoskeleton | 0.0000 | 0.0125 |
| Gefitinib | EGFR | EGFR signalling | 0.0020 | 0.5 |
| ABT-263 | Bcl-2, Bcl-xL, and Bcl-w | apoptosis regulation | 0.0078 | 2 |
| Vorinostat | HDAC inhibitor Class I, IIa, IIb, IV | chromain histone acetylation | 0.0391 | 10 |
| Nilotinib | Bcr-Abl | ABL signalling | 0.0078 | 2 |
| AZD-2281 | PARP1/2 | Genome integrity | 0.0195 | 5 |
| Bosutinib | SRC, ABL, TEC | ABL signalling | 0.0078 | 2 |
| Lenalidomide | TNF alpha | other | 0.0195 | 5 |
| Axitinib | PDGFR, KIT, VEGFR | RTK signalling | 0.0078 | 2 |
| AZD7762 | Chk 1/2 | Genome integrity | 0.0078 | 2 |
| GW 441756 | Trk A | RTK signalling | 0.0078 | 2 |
| CEP-701 | FLT3, JAK2, NTRK1, RET | RTK signalling | 0.0078 | 2 |
| SB 216763 | GSKa/b | WNT signalling | 0.0391 | 10 |
| 17-AAG | Hsp90 | other | 0.0039 | 1 |
| AMG-706 | VEGFR, RET, c-KIT, PDGFR | RTK signalling | 0.0078 | 2 |
| KU-55933 | ATM | Genome integrity | 0.0391 | 10 |
| BIBW2992 | EGFR, HER2 | EGFR signalling | 0.0020 | 0.5 |
| GDC-0449 | SMO | other | 0.0391 | 10 |
| PLX4720 | RAF | ERK MAPK signalling | 0.0391 | 10 |
| BX-795 | TBK1, PDK1, IKK, AURKB/C | other | 0.0195 | 5 |
| NU-7441 | DNAPK | Genome integrity | 0.0078 | 2 |
| SL 0101-1 | RSK, AURKB, PIM3 | ERK MAPK signalling | 0.0391 | 10 |
| BI-D1870 | RSK1/2/3/5, PLK1, AURKB | cell cycle | 0.0195 | 5 |
| BIRB 0796 | p38, JNK2 | JNK and p38 signalling | 0.0391 | 10 |
| JNK Inhibitor VIII | JNK | JNK and p38 signalling | 0.0391 | 10 |
| 681640 | Wee1, Chk1 | cell cycle | 0.0078 | 2 |
| Nutlin-3a | p53-MDM2 interaction | p53 pathway | 0.0313 | 8 |
| mirin | MRE11-Rad50-Nbs1 complex | cell cycle | 0.3906 | 100 |
| PD-173074 | FGFR1, FGFR3 | RTK signalling | 0.0078 | 2 |
| ZM-447439 | Aurora B | mitosis | 0.0156 | 4 |
| RO-3306 | Cdk1 | cell cycle | 0.0195 | 5 |
| MK-2206 | AKT1/2 | PI3K signalling | 0.0156 | 4 |
| PD-0332991 | Cdk 4/6 | cell cycle | 0.0156 | 4 |
| PF477736 | Chk 1 (Chk2) | cell cycle | 0.0039 | 1 |
| GW843682X (AN-13) | Plk1 | mitosis | 0.0195 | 5 |
| NVP-BEZ235 | PI3K Class 1 and mTORC1/2 | PI3K signalling | 0.0010 | 0.25 |
| GDC0941 | PI3K (class 1) | PI3K signalling | 0.0156 | 4 |
| AZD8055 | mTORC1/2 | TOR signalling | 0.0078 | 2 |
| PD-0325901 | MEK 1/2 | ERK MAPK signalling | 0.0010 | 0.25 |
| AZD6482 | PI3K beta | PI3K signalling | 0.0195 | 5 |
| Obatoclax Mesylate | Bcl-2, Bxl-xl, Mcl-1 | apoptosis regulation | 0.0391 | 10 |
| EHT 1864 | Rac GTPases | cytoskeleton | 0.0391 | 10 |
| BMS-708163 | gamma-secretase complex | other | 0.0195 | 5 |
| 5-Fluorouracil | antimetabolite | mitosis | 0.0781 | 20 |
| Paclitaxel | Beta subunit of tubulin | cytoskeleton | 0.0000 | 0.01 |
| PF-02341066 | MET, ALK | RTK signalling | 0.0039 | 1 |
| Sorafenib | PDGFR, KIT, VEGFR | RTK signalling | 0.0156 | 4 |
| BI-2536 | Plk1, 2, 3 | mitosis | 0.0020 | 0.5 |
| BMS-536924 | IGF-1R | IGFR signalling | 0.0156 | 4 |
| GSK1904529A | IGF-IR and IR | IGFR signalling | 0.0195 | 5 |
| AKT inhibitor VIII | AKT1/2/3 | PI3K signalling | 0.0195 | 5 |
| PF-4708671 | p70 S6KA | TOR signalling | 0.0391 | 10 |
| JNJ-26854165 | MDM2 | p53 pathway | 0.0391 | 10 |
| LY317615 | PKC beta | other | 0.0391 | 10 |
| BMS-754807 | IGF-1R/IR | IGFR signalling | 0.0391 | 10 |
| TW 37 | BCL-2, BCL-XL | apoptosis regulation | 0.0195 | 5 |
| Embelin | XIAP | apoptosis regulation | 0.0391 | 10 |
| Erlotinib | EGFR | EGFR signalling | 0.0078 | 2 |
| AZ628 | BRAF | ERK MAPK signalling | 0.0078 | 2 |
| AG-014699 | PARP1/2 | Genome integrity | 0.0195 | 5 |
| Gemcitibine | nucleoside analog | DNA replication | 0.0391 | 10 |
| GSK269962A | ROCK1/2 | cytoskeleton | 0.0195 | 5 |

TABLE 1-continued

Compounds used in combinatorial chemical screen with 15 mesothelioma cell lines together with the Met5a mesothelial normal control line.

| compound | target | Targeted process/pathway | min conc (uM) | max conc (uM) |
|---|---|---|---|---|
| SB-505124 | TGFbetaR-I (ALK5) | other | 0.0391 | 10 |
| Tamoxifen | ER | other | 0.0195 | 5 |
| Fulvestrant | ER | other | 0.0039 | 1 |
| Anastrozole | ER | other | 0.0391 | 10 |
| JQ1 | BRD2, BRD3, BRD4 | chromatin other | 0.0039 | 1 |
| YK 4-279 | RNA helicase A | other | 0.0391 | 10 |
| CHIR-99021 | GSK3B | WNT signalling | 0.0391 | 10 |
| (5Z)-7-Oxozeaenol | TAK1 | other | 0.0391 | 10 |
| FK866 | NAMPT inhibitor | metabolism | 0.0039 | 1 |
| BMS-345541 | IKK-beta | other | 0.0391 | 10 |
| AZ960 | JAK2 | other | 0.0391 | 10 |
| BMN-673 | PARP | Genome integrity | 0.0391 | 10 |
| XAV 939 | Tankyrase (PARP5a) | WNT signalling | 0.0195 | 5 |
| GSK1120212 | MEK1, MEK2 | ERK MAPK signalling | 0.0039 | 1 |
| GSK2118436 | BRAF | ERK MAPK signalling | 0.0391 | 10 |
| Temozolomide | DNA akylating agent | DNA replication | 0.1172 | 30 |
| Olaparib + Temozolomide | DNA damage response | Genome integrity | 0.0391 | 10 |
| AZD2281 | PARP | Genome integrity | 0.0391 | 10 |
| Bicalutamide | Androgen receptor | other | 0.0391 | 10 |
| PF-562271 | FAK | cytoskeleton | 0.0391 | 10 |
| PAC-1 | Caspase 3 activator | apoptosis regulation | 0.0391 | 10 |
| INCB-18424 | JAK1, JAK2, TYK2 | other | 0.0391 | 10 |
| OSI-906 | IGFR-1 | IGFR signalling | 0.0098 | 2.5 |
| Epirubicin | DNA damage | DNA replication | 0.0391 | 10 |
| Cyclophosphamide | DNA akylating agent | DNA replication | 0.0391 | 10 |
| Carboplatin | DNA damage | DNA replication | 0.0391 | 10 |
| Everolimus | mTOR | TOR signalling | 0.0195 | 5 |
| LCL161 | SMAC mimetic | apoptosis regulation | 0.0391 | 10 |
| rTRAIL | Death receptor ligand | apoptosis regulation | 0.39 ng/ml | 100 ng/ml |
| DMSO | CONTROL | NA | | |

TABLE 2

BAP1 mutation status in selected cell lines.

| SAMPLE_NAME | COSMIC_ID | DESCRIPTION | ZYGOSITY | rTRAIL response | BAPI mRNA expression |
|---|---|---|---|---|---|
| H226 | | Deletion | Homozygous | Sensitive | |
| H2461 | 1290810 | Deletion - Frameshift | heterozygous | Sensitive | 0.32 |
| H2722 | 1290812 | HomDel | homozygous | Resistant | −2.52 |
| H2731 | 1240134 | Essential Splice | heterozygous | Sensitive | −0.41 |
| H2795 | 1290813 | Essential Splice | heterozygous | Sensitive* | −0.45 |
| H2804 | 1240136 | Essential Splice | heterozygous | Sensitive | 0.51 |
| IST-MES1 | 907173 | Essential Splice | homozygous | Unknown | −0.33 |
| NCI-H2452 | 908462 | Substitution - Missense | homozygous | Resistant | −0.04 |
| NCI-H28 | 908470 | Essential Splice | heterozygous | Sensitive | 1.27 |
| NCI-H226 | 905941 | HomDel | homozygous | Sensitive** | ND |
| H2595 | 1240132 | Wild-type | heterozygous | Unknown | −2.05 |
| H2369 | 1290808 | Wild-type | heterozygous | Resistant | −0.64 |
| H2373 | 1290809 | Wild-type | heterozygous | Resistant | 1.65 |
| H2591 | 1240131 | Wild-type | heterozygous | Resistant | 0.93 |
| H2803 | 1240135 | Wild-type | heterozygous | Resistant | 0.62 |
| H2810 | 1240137 | Wild-type | heterozygous | Resistant | 1.06 |
| H2818 | 1290814 | Wild-type | heterozygous | Resistant | 0.41 |
| H2869 | 1240138 | Wild-type | heterozygous | Resistant | −0.67 |
| H290 | 1240139 | Wild-type | heterozygous | Unknown | −0.15 |
| H513 | 1240141 | Wild-type | heterozygous | Resistant | 0.11 |
| MPP-89 | 908150 | Wild-type | heterozygous | Resistant | 0.54 |
| MSTO-211H | 908152 | Wild-type | heterozygous | Sensitive** | −0.28 |
| NCI-H2052 | 688058 | Wild-type | heterozygous | Resistant | 0.92 |

Example 2—Modulation of BAP1 Expression Determines TRAIL Sensitivity Through Activation of Cell Death TRAIL binds via two active transmembrane death receptors, DR 4 and DR 5, triggering a caspase cascade and subsequently cell death. The viability effect of TRAIL observed in BAP1 mutant cells was indeed associated with an increased fraction of cells stained with the apoptotic marker Annexin V (see FIG. 3B).

The inventors therefore next examined whether modulation of BAP1 expression in mesothelioma cells resulted in changes in TRAIL sensitivity. The ablation of BAP1 protein with the use of a lentiviral shRNA in the BAP1 wild-type cell line H2818 promoted a shift towards increased sensitivity in the BAP1 null compared to the BAP1 competent parental line (see FIG. 4). The BAP1 null cell line NCI-H226, which possesses a homozygous deletion of BAP1, was transduced with a BAP1 expression vector to restore expression of wild-type full length BAP1 (see FIG. 5A) or the catalytically dead C91A mutant. Treatment of the null NCI-H226 cell line with a dose range of TRAIL resulted in increased cell death which was significantly reduced in the BAP1 expressing H226 cell line (see FIG. 5*b*). The C91A variant however phenocopied the response of the BAP1 null parental cell line indicating a functional Ubiquitin hydrolase catalytic domain is critical for sensitivity to TRAIL. The nuclear localization signal (NLS) also plays a key role in imparting TRAIL resistance as deletion of NLS results in significant reduction in BAP1 induced TRAIL resistance (see FIG. 5*c*).

Example 3—Loss of BAP1 Expression and Function Modulates Components of the Apoptotic Machinery The H226 mesothelioma cell line harbours a homozygous deletion of BAP1, resulting in complete loss of BAP1 expression. The inventors further examined the effect of this catalytically inactive BAP1 on differential mRNA gene expression as well as carrying out a signalling pathway impact analysis (SPIA), as previously described (PMID 18990722). Among those pathways significantly altered when comparing wild-type versus c91a mt BAP1, was that of cell death pathways (see FIG. 6A). In particular, there was decreased expression of members of the IAP family in H226 cells stably transduced with the catalytically dead C91A mutant (see FIG. 6B). The largest effects were seen in CIAP2, and this was confirmed by western blot (see FIG. 6C).

Example 4—Combination Drug Screen Demonstrates Synergy Between SMAC Mimetic LCL161 and rTRAIL in BAP1 Competent Cell Lines rTRAIL was used as an anchor drug in combination with the library of 94 single agent compounds described above. Synergy was described using delta AUC metric (ref Wessles et al) and this was correlated with the previously described genomic subgroups. The inventors have shown that drugs such as SMAC mimetic LCL161, DNA helicase inhibitor YK-4279 and the tyrosine kinase inhibitor sorafenib to increase the efficacy of DRL-induced apoptosis in otherwise resistant cells. One of the most synergistic findings of this screen was the association of sensitivity to the SMAC mimetic LCL161 and rTRAIL in BAP1 wild-type MPM (see FIG. 7 A). This was validated by treating TRAIL resistant wild-type BAP1 expressing cells with combination of LCL161 and TRAIL. Further validation was also performed in the H226 cell lines stably expressing wild-type BAP1 that was previously demonstrated to be resistant to TRAIL alone (see FIGS. 5 and 7B-D). The combination of the IAP inhibitor, LCL161, and TRAIL showed a synergistic increase in cell death in the both mutant and wild-type line indicating that DRL induced cell death in BAP1 mutant and wild-type cells can be enhanced by combining with other agents (see FIG. 7B-D). FIG. 7D in particular shows that both BAP1 mutant and wild-type cells undergo cell death in response to treatment with the combination of TRAIL and LCL161. Endogenous SMAC/Diablo is a specific natural inhibitor of IAP's (14). This data suggests that in the BAP1 competent state, BAP1 loss can be phenocopied by specifically mimicking this inhibitory effect on IAPs resulting in a net inactivation of IAP's and sensitivity to rTRAIL. This would lend further support to the idea that the BAP1/extrinsic apoptotic pathway perturbation seen is related to a specific dysregulation of net activity of IAP's.

Example 5—Extension of BAP1/TRAIL Effect to Other Tissues Harboring BAP1 Loss of Function Mutations The deubiquitinase BAP1 is frequently mutated in pleural mesothelioma (36%), uveal melanoma (47%) and intrahepatic cholangiocarcinomas (25%) as previously noted. To determine whether additional BAP1 mutant tumours occur that may also be amenable to this therapeutic approach, the inventors extended this analysis to a cohort of 5180 tumour samples in 20 cancer types using variant data from The Cancer Genome Atlas (TCGA). Truncating BAP1 mutations were also observed in a diverse range of cancer types, with frequencies of up to 6% (see FIGS. 1*b*, and *c*) Carbone, M. et al, *Nature Reviews Cancer* 13, 153-159 (March 2013). When the inventors extended their analysis to a panel of 1001 cancer cell lines that had previously been submitted for whole exome and copy number analysis, they identified 17 cell lines harbouring truncating mutations in BAP1. These included clear cell kidney cancer, bladder cancer and breast cancer cell lines. Treatment of these cell lines with TRAIL resulted in a marked viability effect compared to BAP1 wild-type cell lines from the same cancer type (see FIG. 8A). The inventors also inactivated BAP1 using a lentiviral shRNA in the breast cancer cell line, MDA-MB231, and observed an exaggerated apoptotic response to rTRAIL (see FIG. 8B). This suggests that TRAIL therapy may be efficacious in other forms of cancer (in addition to mesothelioma), and that inhibition of BAP1 or by targeting the pathway which BAP1 induces TRAIL resistance it is possible to sensitise cancer cells to TRAIL.

The inventors demonstrated the efficacy of targeting BAP1 mutant cells with TRAIL in vivo by mice xenograft models. Mutant and wild-type BAP1 cells were injected subcutaneously into left and right flanks of mice. The mice were treated with either rTRAIL or vehicle (see FIG. 9A). The tumours were weighed at the end of the experiment and the weights of mutated BAP1 tumours in mice that received TRAIL was significantly less than wild-type BAP1 tumours with TRAIL treatment or mutant and wild-type tumours of mice with vehicle treatment (see FIG. 9B). The tumour burden was tracked in real time over a period of 4 weeks. The tumour burden of mutated BAP1 xenografts in mice that received TRAIL was significantly less than wild-type BAP1 xenografts with TRAIL treatment or mutant and wild-type xenografts of mice with vehicle treatment (see FIG. 9C).

Example 6—Role of ASXL Binding Site on of BAP1 Function

The inventors have also demonstrated that a mutation in the ASXL protein binding site of the BAP1 gene impairs BAP1-induced TRAIL resistance (see FIG. 1*i*). BAP1 has been shown to form a complex with proteins ASXL1, ASXL2 or ASXL3. Mutation of the binding site for ASXL protein inhibits formation of BAP1-ASXL complexes. The BAP1-ASXL complex has been shown to deubiquitinate Histone 2A, and other substrates, and both BAP1 and ASXL1, ASXL2, or ASXL3 are required for this deubiquitination function. This complex is an important regulator of the Polycomb Respressor Complex and gene transcription. The inventors have shown that the BAP1 wild-type and ASXL3 mutant (truncating mutation) cell line H513 is TRAIL sensitive. Hence loss of function of ASXL1, ASXL2 or ASXL3 increases the sensitivity of cells to DRL induced cell death. Mutations of ASXL1, ASXL2 or ASXL3 also predict sensitivity to DLR and hence can be used as a biomarker for cell death independent of BAP1 mutational status.

Example 7—Extension of BAP1/TRAIL Effect to Other Extrinsic Death Pathways

Although the data in this application focus on rTRAIL, a recombinant protein that activates the TRAIL pathway by binding to DR 4 and DR 5 receptors, the observed BAP1 mutation-sensitisation extends to other extrinsic apoptotic pathways including the FAS ligand pathway and the TNFalpha pathway (see FIG. 10).

SUMMARY

The inventors have found that BAP1 is an important regulator of whether a cell will undergo cell death in response to the activation of a death receptor by a death receptor ligand, such as TRAIL, TNF alpha (TNFα) and FAS ligand (FASL). Specifically, non-functional or low expression of wild-type BAP1 causes cells to become sensitive to death receptor ligand-induced cell death. Consequently, it has been discovered that a mutant BAP1 gene or a mutant BAP1 protein, or a cancer cell with low expression of a wild-type BAP1 protein may be used as a biomarker of sensitivity to DRL-induced cell death.

Thus, the invention also encompasses an advantageous:

method of determining if an individual's cancer cell is sensitive to death receptor ligand (DRL)-induced cell death;

kit for determining if an individual's cancer cell is sensitive to DRL-induced cell death;

method of selectively inducing death receptor ligand induced cell death in an individual suffering from a cancer that is insensitive to death receptor ligand induced cell death;

a method of sensitising to DRL-induced cell death, an individual suffering from a cancer that is insensitive to DRL-induced cell death;

a composition comprising a BAP1 inhibitor and a death receptor ligand; and a method of treating, preventing or ameliorating an individual suffering from a cancer, which is insensitive to DRL-induced cell death.

REFERENCES

1. Lanphear B P, Buncher C R. Latent period for malignant mesothelioma of occupational origin. Journal of occupational medicine: official publication of the Industrial Medical Association. 1992; 34(7):718-21. Epub 1992/07/01.
2. Lemen R A, Dement J M, Wagoner J K. Epidemiology of asbestos-related diseases. Environmental health perspectives. 1980; 34:1-11. Epub 1980/02/01.
3. Algranti E, Saito C A, Carneiro A P, Moreira B, Mendonca E M, Bussacos M A. The next mesothelioma wave: Mortality trends and forecast to 2030 in Brazil. Cancer epidemiology. 2015. Epub 2015/09/01.
4. Treasure T, Waller D, Tan C, Entwisle J, O'Brien M, O'Byrne K, et al. The Mesothelioma and Radical surgery randomized controlled trial: the Mars feasibility study. Journal of thoracic oncology: official publication of the International Association for the Study of Lung Cancer. 2009; 4(10):1254-8. Epub 2009/08/08.
5. Vogelzang N J, Rusthoven J J, Symanowski J, Denham C, Kaukel E, Ruffle P, et al. Phase III study of pemetrexed in combination with cisplatin versus cisplatin alone in patients with malignant pleural mesothelioma. Journal of clinical oncology: official journal of the American Society of Clinical Oncology. 2003; 21(14):2636-44. Epub 2003/07/16.
6. Guo G, Chmielecki J, Goparaju C, Heguy A, Dolgalev I, Carbone M, et al. Whole-exome sequencing reveals frequent genetic alterations in BAP1, NF2, CDKN2A, and CUL1 in malignant pleural mesothelioma. Cancer research. 2015; 75(2):264-9. Epub 2014/12/10.
7. Bott M, Brevet M, Taylor B S, Shimizu S, Ito T, Wang L, et al. The nuclear deubiquitinase BAP1 is commonly inactivated by somatic mutations and 3p21.1 losses in malignant pleural mesothelioma. Nature genetics. 2011; 43(7):668-72. Epub 2011/06/07.
8. Martin M, Masshofer L, Temming P, Rahmann S, Metz C, Bornfeld N, et al. Exome sequencing identifies recurrent somatic mutations in EIF1AX and SF 3B1 in uveal melanoma with disomy 3. Nature genetics. 2013; 45(8):933-6. Epub 2013/06/26.
9. Gerlinger M, Horswell S, Larkin J, Rowan A J, Salm M P, Varela I, et al. Genomic architecture and evolution of clear cell renal cell carcinomas defined by multiregion sequencing. Nature genetics. 2014; 46(3):225-33. Epub 2014/02/04.
10. Chan-On W, Nairismagi M L, Ong C K, Lim W K, Dima S, Pairojkul C, et al. Exome sequencing identifies distinct mutational patterns in liver fluke-related and non-infection-related bile duct cancers. Nature genetics. 2013; 45(12):1474-8. Epub 2013/11/05.
11. Narasimhan S R, Yang L, Gerwin B I, Broaddus V C. Resistance of pleural mesothelioma cell lines to apoptosis: relation to expression of Bcl-2 and Bax. The American journal of physiology. 1998; 275(1 Pt 1):L165-71. Epub 1998/08/05.
12. Hinds M G, Norton R S, Vaux D L, Day C L. Solution structure of a baculoviral inhibitor of apoptosis (IAP) repeat. Nature structural biology. 1999; 6(7):648-51. Epub 1999/07/15.
13. de Almagro M C, Vucic D. The inhibitor of apoptosis (IAP) proteins are critical regulators of signaling pathways and targets for anti-cancer therapy. Experimental oncology. 2012; 34(3):200-11. Epub 2012/10/17.
14. Yu J, Wang P, Ming L, Wood M A, Zhang L. SMAC/Diablo mediates the proapoptotic function of PUMA by regulating PUMA-induced mitochondrial events. Oncogene. 2007; 26(29):4189-98. Epub 2007/01/24.

15. Behjati S et al. Recurrent PTPRB and PLCG1 mutations in angiosarcoma. Nat Genet, 2014 April; 46(4):376-9. doi: 10.1038/ng.2921.

16. Tarpey P S et al Frequent mutation of the major cartilage collagen gene COL2A1 in Chondrosarcoma. *Nat Genet.* 2013, August; 45(8): 923-926.

17. Li, H and Durbin, R Fast and accurate short read alignment with Burrows-Wheeler transform. Bioinformatics, 2009. 25(14): p 1754-60.

18. Garnett, M. J., et al., Systemic identification of genomic markers of drug sensitivity in cancer cells. Nature, 2012. 483 (7391): p. 473-81.

19. Behjati, S. et al., Mobile DNA in cancer. Extensive transduction of nonrepetitive DNA mediated by Li retrotransposition in cancer genome. Science, 2014. 345 (6196): p. 1251343.

20. Ganten T, Koschny R, Sykora J, Schulze-Bergkamen H, Buchler P, Haas T, et al. Preclinical differentiation between apparently safe and potentially hepatotoxic applications of TRAIL either alone or in combination with chemotherapeutic drugs. Clin Cancer Res. 2006; 12:2640-6

The invention claimed is:

1. A method of treating an individual suffering from cancer, wherein the cancer is selected from mesothelioma, renal cell carcinoma or cholangiocarcinoma, and wherein the cancer is sensitive to death receptor ligand (DRL)-induced cell death, the method comprising:

(i) detecting for the presence of a mutant BAP1 gene or mutant BAP1 protein, or for a reduced level of expression of a wild-type BAP1 gene or a lower wild-type BAP1 protein concentration compared to the level of expression or protein concentration in a reference cell that is a BAP1 wild-type cell that is resistant to DRL-induced cell death, or for reduced or non-binding of an ASXL protein to a wild-type BAP1 protein compared to the level of binding in a reference cell that is a BAP1 wild-type cell, which is resistant to DRL-induced cell death; and (ii) administering, or having administered, a therapeutically effective amount of a death receptor ligand to the individual.

2. The method according to claim 1, wherein the mutant BAP1 gene is a gene that encodes a non-functional or enzymatically inactive BAP1 protein, or a BAP1 protein that exhibits reduced binding to an ASXL protein compared to the level of binding in a reference cell, which is resistant to DRL-induced cell death.

3. The method according to claim 1, wherein the reduced level of expression is at least a 10%, 15%, 25%, 35%, 45%, 50%, 55%, 60%, 65%, 70%, 75%, 80%, 85%, 90%, 95% or a 100% reduction compared to the reference cell.

4. The method according to claim 1, wherein the nucleotide sequence of the mutant BAP1 gene is SEQ ID NO. 5 or a fragment or variant thereof.

5. A method according to claim 1, wherein the death receptor ligand is selected from a group consisting of: TRAIL, TNF alpha; FAS ligand (FASL); recombinant TRAIL comprising dulanermin; antibody to a death receptor; mapatumuab; drozitumumab; conatumumab; lexatumumab; tigatuzumab; Medi-3038; Medi-3039; and LBY-135; or a combination thereof.

* * * * *